US008790642B2

(12) United States Patent
Chen et al.

(10) Patent No.: US 8,790,642 B2
(45) Date of Patent: Jul. 29, 2014

(54) CROSS-REACTIVE AND BISPECIFIC ANTI-IL-17A/F ANTIBODIES

(75) Inventors: Yongmei Chen, San Francisco, CA (US); Yan (Helen) Hu, Foster City, CA (US); Wenjun Ouyang, Foster City, CA (US); Scott Stawicki, San Francisco, CA (US); Yan Wu, Foster City, CA (US)

(73) Assignee: Genentech, Inc., South San Francisco, CA (US)

( * ) Notice: Subject to any disclaimer, the term of this patent is extended or adjusted under 35 U.S.C. 154(b) by 450 days.

(21) Appl. No.: 12/547,728

(22) Filed: Aug. 26, 2009

(65) Prior Publication Data

US 2010/0055103 A1 Mar. 4, 2010

Related U.S. Application Data

(60) Provisional application No. 61/164,709, filed on Mar. 30, 2009, provisional application No. 61/112,644, filed on Nov. 7, 2008, provisional application No. 61/093,212, filed on Aug. 29, 2008.

(51) Int. Cl.
*A61K 39/395* (2006.01)

(52) U.S. Cl.
USPC ............... 424/133.1; 424/145.1; 424/141.1; 530/388.23; 530/388.1; 530/387.3; 530/351

(58) Field of Classification Search
None
See application file for complete search history.

(56) References Cited

U.S. PATENT DOCUMENTS

| 7,790,163 B2 * | 9/2010 | Jaspers et al. ............... 424/141.1 |
| 2002/0177188 A1 | 11/2002 | Chen et al. |
| 2006/0270003 A1 | 11/2006 | Arnott et al. |
| 2007/0160576 A1 | 7/2007 | Arnott et al. |

FOREIGN PATENT DOCUMENTS

| WO | WO 01/146420 | 6/2001 |
| WO | WO 2007/056470 A2 | 5/2007 |
| WO | WO 2007/106769 A2 | 9/2007 |
| WO | WO 2008/047134 A2 | 4/2008 |
| WO | WO 2009/136286 A2 | 11/2009 |

OTHER PUBLICATIONS

Paul, Fundamental Immunology, 3rd Edition, 1993, pp. 292-295, under the heading "Fv Structure and Diversity in Three Dimensions".*
Pascalis et al. Grafting of "abbreviated" complementarity-determining regions containing specificity-determining residues essential for ligand contact to engineer a less immunogenic humanized monoclonal antibody. J. Immunol. 2002, 169:3076-3084.*
Wark, et al., "Latest technologies for the enhancement of antibody affinity", Advanced drug delivery reviews, vol. 58, pp. 657-670, (2006).
Aggarwal, et al., "IL-17: prototype member of an emerging cytokine family", Journal of Leukocyte Biology, vol. 71, pp. 1-8, (2002).
Aggarwal, et al., "Interleukin-23 promotes a distinct CD4 T cell activation state characterized by the production of Interleukin-17", The Journal of Biological Chemistry, vol. 278, No. 3, pp. 1910-1914, (2003).
Albanesi, et al., Interleukin-17 is produced by both Th1 and Th2 lymphocytes, and modulates interferon-γ- and Interleukin-4- induced activation of human Keratinocytes, The Journal of Investigative Dermatology, vol. 115, No. 1, pp. 81-87, (2000).
Cai, et al., "Regulation of granulocyte colony-stimulating factor gene expression by interleukin-17", Immunology Letters, vol. 62, pp. 51-58, (1998).
Chabaud, et al., "A T cell-derived proinflammatory cytokine produced by the rheumatoid synovium", Arthritis & Rheumatism, vol. 42, No. 5, pp. 963-970, (1999).
Chabaud, et al., "Enhancing effect of IL-17 on IL-1-induced IL-16 and leukemia inhibitory factor production by rheumatoid arthritis synoviocytes and its regulation by Th2 cytokines", The Journal of Immunology, pp. 409-414, (1998).
Chang, et al., "A novel heterodimeric cytokine consisting of IL-17 and IL-17F regulates inflammatory responses", Cell Research, vol. 17, pp. 435-440, (2007).
Fossiez, et al., "T Cell interleukin-17 induces stromal cells to produce proinflammatory and hematopoietic cytokines", J. Exp. Med., vol. 183, pp. 2593-2603, (1996).
Homey, et al., Up-Regulation of macrophage inflammatory protein-3α/CCL20 and CC Chemokine receptor 6 in psoriasis[1], The Journal of Immunology, vol. 164, pp. 6621-6632, (2000).
Hymowitz, et al., "IL-17s adopt a cystine knot fold: structure and activity of a novel cytokine, IL-17F and implications for receptor binding", The EMBO Journal, vol. 20, No. 19, pp. 5332-5341, (2001).
Jovanovic, et al., "IL-17 stimulates the production and expression of proinflammatory cytokines, IL-β and TNF-α by human macrophages", The Journal of Immunology, vol. 160, pp. 3513-3521, (1998).
Kennedy, et al., "Mouse IL-17: A cytokine preferentially expressed by αβTCR + CD4—CD8—T cells", Journal of Interferon and Cytokine Research, vol. 16, pp. 611-617, (1996).
Kotake, et al., "IL-17 in synovial fluids from patients with rheumatoid arthritis is a potent stimulator of osteoclatogenesis", The Journal of Clinical Investigation, vol. 103, No. 9, pp. 1345-1352, (1999).
Kurasawa, et al., "Increased interleukin-17 production in patients with systemic sclerosis", Arthritis & Rheumatism, vol. 43, No. 11, pp. 2455-2463, (2000).
Laan, et al., "Neutrophil recruitment by human IL-17 via C-X-C chemokine release in the airways[1]", The Journal of Immunology, vol. 162, pp. 2347-2352, (1999).
Liang, et al., "An IL-17F/A heterodimer protein is produced by mouse Th17 cells and induces airway neutrophil recruitment", The journal of Immunology, vol. 179, pp. 7791-7799, (2007).

(Continued)

*Primary Examiner* — Dong Jiang
(74) *Attorney, Agent, or Firm* — Y. Elanie Chang; Ginger R. Dreger; Arnold & Porter LLP

(57) ABSTRACT

The present invention relates generally to antibodies cross-reactive with IL-17A and IL-17F, and bispecific anti-IL-17A/F and their uses.

11 Claims, 21 Drawing Sheets

(56) References Cited

OTHER PUBLICATIONS

Linden, et al., "Airway neutrophils and interleukin-17", Eur. Respir., vol. 15, pp. 973-977, (2000).

Matusevicius, et al., "Interleukin-17 mRNA expression in blood and CSF mononuclear cells is augmented in multiple sclerosis", Multiple Aclerosis, vol. 5, pp. 101-104, (1999).

Shalom-Barak, et al., "Interleukin-17-induced gene expression in articular chonrocytes is associated with activation of mitogen-activated protein kinases and NF-κB*", The Journal of Biological Chemistry, vol. 273, No. 42, pp. 27467-27473, (1998).

Starnes, et al., "Cutting Edge: IL-17F, a novel cytokine selectively expressed in activated T cells and monocytes, regulates angiogenesis and endothelial cell cytokine production", The Journal of Immunology, vol. 167, pp. 4137-4140, (2001).

Teunissen, et al., "Interleukin-17 and interferon-γ synergize in the enhancement of proinflammatory cytokine production by human keratinocytes", The Journal of Investigative Dermatology, vol. 111, pp. 645-649, (1998).

Van Bezooijen, et al., "Interleukin-17: A new bone acting cytokine in vitro*", Journal of Bone and Mineral Research, vol. 14, No. 9, pp. 1513-1521, (1999).

Wright, et al., "The human IL-17F/IL-17A heterodimeric cytokine signals through the IL-17RA/IL-17RC receptor complex", The Journal of Immunology, vol. 181, pp. 2799-2805, (2008).

Yao, et al., "Herpesvirus saimiri encodes a new cytokine, IL-17 which binds to a novel cytokine receptor", Immunity, vol. 3, pp. 811-821, (1995).

Yao, et al., "Human IL-17: A novel cytokine derived from T cells", The Journal of Immunology, vol. 155, pp. 5483-5486, (1995).

Yao, et al., "Molecular characterization of the human interleukin (IL)-17 receptor", Cytokine, vol. 9, No. 11, pp. 794-800, (1997).

* cited by examiner

Human IL17A cDNA:

ATGACTCCTGGGAAGACCTCATTGGTGTCACTGCTACTGCTGCTGAG
CCTGGAGGCCATAGTGAAGGCAGGAATCACAATCCCACGAAATCCAG
GATGCCCAAATTCTGAGGACAAGAACTTCCCCCGGACTGTGATGGTC
AACCTGAACATCCATAACCGGAATACCAATACCAATCCCAAAAGGTC
CTCAGATTACTACAACCGATCCACCTCACCTTGGAATCTCCACCGCA
ATGAGGACCCTGAGAGATATCCTCTGTGATCTGGGAGGCAAAGTGC
CGCCACTTGGGCTGCATCAACGCTGATGGAACGTGGACTACCACAT
GAACTCTGTCCCCATCCAGCAAGAGATCCTGGTCCTGCGCAGGGAGC
CTCCACACTGCCCCAACTCCTTCCGGCTGGAGAAGATACTGGTGTCC
GTGGGCTGCACCTGTGTCACCCCGATTGTCCACCATGTGGCCTAA (SEQ ID NO: 1)

FIG. 1

MTPGKTSLVSLLLLLSLEAIVKAGITIPRNPGCPNSEDKNFPRTVMV
NLNIHNRNTNTNPKRSSDYYNRSTSPWNLHRNEDPERYPSVIWEAKC
RHLGCINADGNVDYHMNSVPIQQEILVLRREPPHCPNSFRLEKILVS
VGCTCVTPIVHHVA (SEQ ID NO: 2)

FIG. 2

Human IL17F cDNA:

ATGACAGTGAAGACCCTGCATGGCCCAGCCATGGTCAAGTACTTGCT
GCTGTCGATATTGGGGCTTGCCTTTCTGAGTGAGGCGGCAGCTCGGA
AAATCCCCAAAGTAGGACATACTTTTTTCCAAAAGCCTGAGAGTTGC
CCGCCTGTGCCAGGAGGTAGTATGAAGCTTGACATTGGCATCATCAA
TGAAAACCAGCGCGTTTCCATGTCACGTAACATCGAGAGCCGCTCCA
CCTCCCCCTGGAATTACACTGTCACTTGGGACCCCAACCGGTACCCC
TCGGAAGTTGTACAGGCCCAGTGTAGGAACTTGGGCTGCATCAATGC
TCAAGGAAAGGAAGACATCTCCATGAATTCCGTTCCCATCCAGCAAG
AGACCCTGGTCGTCCGGAGGAAGCACCAAGGCTGCTCTGTTTCTTTC
CAGTTGGAGAAGGTGCTGGTGACTGTTGGCTGCACCTGCGTCACCCC
TGTCATCCACCATGTGCAGTAA (SEQ ID NO: 3)

FIG. 3

MTVKTLHGPAMVKYLLLSILGLAFLSEAAARKIPKVGHTFFQKPESC
PPVPGGSMKLDIGIINENQRVSMSRNIESRSTSPWNYTVTWDPNRYP
SEVVQAQCRNLGCINAQGKEDISMNSVPIQQETLVVRRKHQGCSVSF
QLEKVLVTVGCTCVTPVIHHVQ (SEQ ID NO: 4)

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | A | B | C | D | E | F | 28 | 29 | 30 | 31 | 32 | 33 | 34 | 35 | 36 | 37 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | | | | | | | | | | Kabat - CDR L1 | | | | | | | | | |
| | | | | | | | | | | | | | | | | | | | | | | | | | | | | | | | | | | | | Chothia - CDR L1 | | | | | | |
| | | | | | | | | | | | | | | | | | | | | | | | | | | | | | | | | | | | | | | Contact - CDR L1 | | | | |
| 278.15.7 | D | I | Q | M | T | Q | S | P | S | S | L | S | A | S | V | G | D | R | V | T | I | T | C | R | A | S | Q | | | | | | | D | V | S | T | A | V | A | W | Y | Q |
| 278.15.8 | D | I | Q | M | T | Q | S | P | S | S | L | S | A | S | V | G | D | R | V | T | I | T | C | R | A | S | Q | | | | | | | D | V | S | T | A | V | A | W | Y | Q |
| 278.15.9 | D | I | Q | M | T | Q | S | P | S | S | L | S | A | S | V | G | D | R | V | T | I | T | C | R | A | S | Q | | | | | | | D | V | S | T | A | V | A | W | Y | Q |
| 279.1.20 | D | I | Q | M | T | Q | S | P | S | S | L | S | A | S | V | G | D | R | V | T | I | T | C | R | A | S | Q | | | | | | | R | I | K | R | Y | L | A | W | Y | Q |
| 279.1.21 | D | I | Q | M | T | Q | S | P | S | S | L | S | A | S | V | G | D | R | V | T | I | T | C | R | A | S | Q | | | | | | | | S | I | S | S | Y | L | A | W | Y | Q |
| 279.1.22 | D | I | Q | M | T | Q | S | P | S | S | L | S | A | S | V | G | D | R | V | T | I | T | C | R | A | S | Q | | | | | | | | S | I | S | S | Y | L | A | W | Y | Q |

| Kabat# | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | Kabat - CDR L2 | | | | | | | | | | | | | | | | | | | | | | | | | | | | | | |
| | | | | | | | | | | | | | | Chothia - CDR L2 | | | | | | | | | | | | | | | | | | | | | | | | | | | | | |
| | | | | | | | | | | Contact - CDR L2 | | | | | | | | | | | | | | | | | | | | | | | | | | | | | | | | | |
| 278.15.7 | Q | K | P | G | K | A | P | K | L | L | I | Y | S | A | S | F | L | Y | S | G | V | P | S | R | F | S | G | S | G | S | G | T | D | F | T | L | T | I | S | S | L | Q | P |
| 278.15.8 | Q | K | P | G | K | A | P | K | L | L | I | Y | S | A | S | F | L | Y | S | G | V | P | S | R | F | S | G | S | G | S | G | T | D | F | T | L | T | I | S | S | L | Q | P |
| 278.15.9 | Q | K | P | G | K | A | P | K | L | L | I | Y | S | A | S | F | L | Y | S | G | V | P | S | R | F | S | G | S | G | S | G | T | D | F | T | L | T | I | S | S | L | Q | P |
| 279.1.20 | Q | K | P | G | K | A | P | K | L | L | I | Y | G | A | S | S | R | A | S | G | V | P | S | R | F | S | G | S | G | S | G | T | D | F | T | L | T | I | S | S | L | Q | P |
| 279.1.21 | Q | K | P | G | K | A | P | K | L | L | I | Y | G | A | S | S | R | A | S | G | V | P | S | R | F | S | G | S | G | S | G | T | D | F | T | L | T | I | S | S | L | Q | P |
| 279.1.22 | Q | K | P | G | K | A | P | K | L | L | I | Y | G | A | S | S | R | A | S | G | V | P | S | R | F | S | G | S | G | S | G | T | D | F | T | L | T | I | S | S | L | Q | P |

| Kabat# | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | 108 |
|---|---|---|---|---|---|---|---|---|---|---|---|---|---|---|---|---|---|---|---|---|---|---|---|---|---|---|---|---|
| | | | | | | | | | | | Kabat - CDR L3 | | | | | | | | | | | | | | | | | |
| | | | | | | | | | | | | Chothia - CDR L3 | | | | | | | | | | | | | | | | |
| | | | | | | | | | | Contact - CDR L3 | | | | | | | | | | | | | | | | | | |
| 278.15.7 | E | D | F | A | T | Y | Y | C | Q | Q | S | Y | T | P | R | S | T | F | G | Q | G | T | K | V | E | I | K | R |
| 278.15.8 | E | D | F | A | T | Y | Y | C | Q | Q | Y | Y | S | T | T | Q | T | F | G | Q | G | T | K | V | E | I | K | R |
| 278.15.9 | E | D | F | A | T | Y | Y | C | Q | Q | S | Q | N | P | Q | H | H | F | G | Q | G | T | K | V | E | I | K | R |
| 279.1.20 | E | D | F | A | T | Y | Y | C | Q | Q | R | F | S | Q | H | W | T | F | G | Q | G | T | K | V | E | I | K | R |
| 279.1.21 | E | D | F | A | T | Y | Y | C | Q | Q | R | Y | S | T | T | L | P | F | G | Q | G | T | K | V | E | I | K | R |
| 279.1.22 | E | D | F | A | T | Y | Y | C | Q | Q | R | Y | S | T | T | L | P | T | G | Q | G | T | K | V | E | I | K | R |

```
Kabat#    1  2  3  4  5  6  7  8  9 10 11 12 13 14 15 16 17 18 19 20 21 22 23 24 25 26 27 28 29 30 31 32 33 34 35 36 37 38 39 40
                                                                                              |—Chothia-CDR H1—|  |—Kabat-CDR H1—|
                                                                                              |————Contact-CDR H1————|
278.15.7  E  V  Q  L  V  E  S  G  G  G  L  V  Q  P  G  G  S  L  R  L  S  C  A  A  S  G  F  T  F  T  D  Y  D  I  S  W  V  R  Q  A
278.15.8  E  V  Q  L  V  E  S  G  G  G  L  V  Q  P  G  G  S  L  R  L  S  C  A  A  S  G  F  T  F  T  D  Y  D  I  S  W  V  R  Q  A
278.15.9  E  V  Q  L  V  E  S  G  G  G  L  V  Q  P  G  G  S  L  R  L  S  C  A  A  S  G  F  T  F  T  D  Y  D  I  S  W  V  R  Q  A
279.1.20  E  V  Q  L  V  E  S  G  G  G  L  V  Q  P  G  G  S  L  R  L  S  C  A  A  S  G  F  T  F  S  Y  M  M  S  W  V  R  Q  A
279.1.21  E  V  Q  L  V  E  S  G  G  G  L  V  Q  P  G  G  S  L  R  L  S  C  A  A  S  G  F  T  F  S  Y  M  M  S  W  V  R  Q  A
279.1.22  E  V  Q  L  V  E  S  G  G  G  L  V  Q  P  G  G  S  L  R  L  S  C  A  A  S  G  F  S  F [P] S  Y [F][I] S  W  V  R  Q  A Kabat#   41 42 43 44 45 46 47 48 49 50 51 52  A  B  C 53 54 55 56 57 58 59 60 61 62 63 64 65 66 67 68 69 70 71 72 73 74 75 76 77 78
                                  |—————Kabat-CDR H2—————|
                            |—Chothia-CDR H2—|
                      |————Contact-CDR H2————|
278.15.7  P  G  K  G  L  E  W  V  A  S  I  S  P           Y  D  G  Y  A  Y  Y  A  D  S  V  K  G  R  F  T  I  S  A  D  T  S  K  N  T  A
278.15.8  P  G  K  G  L  E  W  V  A  S  I  S  P           L  D  G  Y  S  Y  Y  A  D  S  V  K  G  R  F  T  I  S  A  D  T  S  K  N  T  A
278.15.9  P  G  K  G  L  E  W  V  A  S  I  D  P           Y  E  G  Y  T  Y  Y  A  D  S  V  K  G  R  F  T  I  S  A  D  T  S  K  N  T  A
279.1.20  P  G  K  G  L  E  W  V  S  T  I  Y  P           E  S  G  A  T  D  Y  A  D  S  V  K  G  R  F  T  I  S  A  D  T  S  K  N  T  A
279.1.21  P  G  K  G  L  E  W  V [M] I  Y  P              E  S  G  A  T  V  Y  A  D  S  V  K  G  R  F  T  I  S  A  D  T  S  K  N  T  A
279.1.22  P  G  K  G  L  E  W  V  S  I  Y  P             [V] S  G  A  T  V  Y  A  D  S  V  K  G  R  F  T  I  S  A  D  T  S  K  N  T  A Kabat#   79 80 81 82  A  B  C 83 84 85 86 87 88 89 90 91 92 93 94 95 96 97 98 99 100  A  B  C
                                                                              |—Kabat-CDR H3—
                                                                              |—Chothia-CDR H3—
                                                                              |—Contact-CDR H3—
278.15.7  Y  L  Q  M  N  S  L  R  A  E  D  T  A  V  Y  Y  C  A  R  Y  L  Y  W  S  Y  Y
278.15.8  Y  L  Q  M  N  S  L  R  A  E  D  T  A  V  Y  Y  C  A  R  Y  L  Y  W  S  Y  Y
278.15.9  Y  L  Q  M  N  S  L  R  A  E  D  T  A  V  Y  Y  C  A  R  Y  L  Y  W  S  Y  Y
279.1.20  Y  L  Q  M  N  S  L  R  A  E  D  T  A  V  Y  Y  C  A  R  E  G  Y  Y  Y  S  T  S  I  K  Y  Y  P
279.1.21  Y  L  Q  M  N  S  L  R  A  E  D  T  A  V  Y  Y  C  A  R  E  G  Y  Y  Y  S  T  S  I  K  Y  Y  P
279.1.22  Y  L  Q  M  N  S  L  R  A  E  D  T  A  V  Y  Y  C  A  R  E  G  Y  Y  Y  S  T  S  I  K  Y  Y  P Kabat#   101 102 103 104 105 106  #  # 108 109 110 111 112 113
278.15.7   M   D   Y                W  G  Q   G   T   L   V   T   V   S   S
278.15.8   M   D   Y                W  G  Q   G   T   L   V   T   V   S   S
278.15.9   M   D   Y                W  G  Q   G   T   L   V   T   V   S   S
279.1.20   W   F   D   Y            W  G  Q   G   T   L   V   T   V   S   S
279.1.21   W   F   D   Y            W  G  Q   G   T   L   V   T   V   S   S
279.1.22   W   F   D   Y            W  G  Q   G   T   L   V   T   V   S   S
```

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | A | B | C | D | E | F | 28 | 29 | 30 | 31 | 32 | 33 | 34 | 35 | 36 | 37 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | | | | | | | | | | | | | | | | | | | |
| | | | | | | | | | | | | | | | | | | | | | | | | | | | | | | | | | | Kabat - CDR L1 | | | | | | | | |
| | | | | | | | | | | | | | | | | | | | | | | | | | | | | | | | | | | Chothia - CDR L1 | | | | | | | | |
| | | | | | | | | | | | | | | | | | | | | | | | | | | | | | | | | | | | | Contact - CDR L1 | | | | | | |
| 278.15    | D | I | Q | M | T | Q | S | P | S | S | L | S | A | S | V | G | D | R | V | T | I | T | C | R | A | S | Q | | | | | | | D | V | S | T | A | V | A | W | Y | Q |
| 278.15.18 | D | I | Q | M | T | Q | S | P | S | S | L | S | A | S | V | G | D | R | V | T | I | T | C | R | A | S | Q | | | | | | | D | V | S | T | A | V | A | W | Y | Q |
| 278.15.2  | D | I | Q | M | T | Q | S | P | S | S | L | S | A | S | V | G | D | R | V | T | I | T | C | R | A | S | Q | | | | | | | D | V | S | T | A | V | A | W | Y | Q |
| 278.15.3  | D | I | Q | M | T | Q | S | P | S | S | L | S | A | S | V | G | D | R | V | T | I | T | C | R | A | S | Q | | | | | | | V | I | S | S | S | L | A | W | Y | Q |

| Kabat# | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | Kabat - CDR L2 | | | | | | | | | | | | | | | | | | | | | | | | | | | | | | |
| | | | | | | | | | | | | Chothia - CDR L2 | | | | | | | | | | | | | | | | | | | | | | | | | | | | | | |
| | | | | | | | | | Contact - CDR L2 | | | | | | | | | | | | | | | | | | | | | | | | | | | | | | | | | |
| 278.15    | Q | K | P | G | K | A | P | K | L | L | I | Y | S | A | S | F | L | Y | S | G | V | P | S | R | F | S | G | S | G | S | G | T | D | F | T | L | T | I | S | S | L | Q | P |
| 278.15.18 | Q | K | P | G | K | A | P | K | L | L | I | Y | S | A | S | F | L | Y | S | G | V | P | S | R | F | S | G | S | G | S | G | T | D | F | T | L | T | I | S | S | L | Q | P |
| 278.15.2  | Q | K | P | G | K | A | P | K | L | L | I | Y | S | A | S | F | F | Y | S | G | V | P | S | R | F | S | G | S | G | S | G | T | D | F | T | L | T | I | S | S | L | Q | P |
| 278.15.3  | Q | K | P | G | K | A | P | K | L | L | I | Y | G | A | S | F | F | Y | S | G | V | P | S | R | F | S | G | S | G | S | G | T | D | F | T | L | T | I | S | S | L | Q | P |

| Kabat# | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | 108 |
|---|---|---|---|---|---|---|---|---|---|---|---|---|---|---|---|---|---|---|---|---|---|---|---|---|---|---|---|---|
| | | | | | | | | | | Kabat - CDR L3 | | | | | | | | | | | | | | | | | | |
| | | | | | | | | | | Chothia - CDR L3 | | | | | | | | | | | | | | | | | | |
| | | | | | | | | | | Contact - CDR L3 | | | | | | | | | | | | | | | | | | |
| 278.15    | E | D | F | A | T | Y | Y | C | Q | Q | S | Y | T | T | R | P | T | F | G | Q | G | T | K | V | E | I | K | R |
| 278.15.18 | E | D | F | A | T | Y | Y | C | Q | Q | S | Y | T | A | K | L | T | F | G | Q | G | T | K | V | E | I | K | R |
| 278.15.2  | E | D | F | A | T | Y | Y | C | Q | Q | Y | Y | I | Y | P | A | T | F | G | Q | G | T | K | V | E | I | K | R |
| 278.15.3  | E | D | F | A | T | Y | Y | C | Q | Q | H | N | D | L | P | L | T | F | G | Q | G | T | K | V | E | I | K | R |

```
Kabat#           1  2  3  4  5  6  7  8  9 10 11 12 13 14 15 16 17 18 19 20 21 22 23 24 25 26 27 28 29 30 31 32 33 34 35 36 37 38 39 40
                                                                                                    |___Chothia-CDR H1___|
                                                                                                          |_Kabat-CDR H1_|
                                                                                                       |_Contact-CDR H1_|
278.15           E  V  Q  L  V  E  S  G  G  G  L  V  Q  P  G  G  S  L  R  L  S  C  A  A  S  G  F  T  F  T  D  Y  D  I  S  W  V  R  Q  A
278.15.18        E  V  Q  L  V  E  S  G  G  G  L  V  Q  P  G  G  S  L  R  L  S  C  A  A  S  G  F  T  F  T  D  Y  D  I  S  W  V  R  Q  A
278.15.18.C55A   E  V  Q  L  V  E  S  G  G  G  L  V  Q  P  G  G  S  L  R  L  S  C  A  A  S  G  F  T  F  T  D  Y  D  I  S  W  V  R  Q  A
278.15.18.C55S   E  V  Q  L  V  E  S  G  G  G  L  V  Q  P  G  G  S  L  R  L  S  C  A  A  S  G  F  T  F  T  D  Y  D  I  S  W  V  R  Q  A
278.15.2         E  V  Q  L  V  E  S  G  G  G  L  V  Q  P  G  G  S  L  R  L  S  C  A  A  S  G  F  S  F  I  D  Y  D  I  S  W  V  R  Q  A
278.15.2.D54E    E  V  Q  L  V  E  S  G  G  G  L  V  Q  P  G  G  S  L  R  L  S  C  A  A  S  G  F  S  F  I  D  Y  D  I  S  W  V  R  Q  A
278.15.3         E  V  Q  L  V  E  S  G  G  G  L  V  Q  P  G  G  S  L  R  L  S  C  A  A  S  G  F  T  F  T  D  Y  D  I  S  W  V  R  Q  A Kabat#          41 42 43 44 45 46 47 48 49 50 51 52  A  B  C 53 54 55 56 57 58 59 60 61 62 63 64 65 66 67 68 69 70 71 72 73 74 75 76 77 78
                                                  |___Chothia-CDR H2___|
                                                     |_____Kabat-CDR H2_____|
                                                  |_____Contact-CDR H2_____|
278.15           P  G  K  G  L  E  W  V  A  S  I  S  P           S  D  G  Y  T  Y  Y  A  D  S  V  K  G  R  F  T  I  S  A  D  T  S  K  N  T  A
278.15.18        P  G  K  G  L  E  W  V  A  S  I  S  P           P  D  C  Y  Y  Y  Y  A  D  S  V  K  G  R  F  T  I  S  A  D  T  S  K  N  T  A
278.15.18.C55A   P  G  K  G  L  E  W  V  A  S  I  S  P           P  D  A  Y  Y  Y  Y  A  D  S  V  K  G  R  F  T  I  S  A  D  T  S  K  N  T  A
278.15.18.C55S   P  G  K  G  L  E  W  V  A  S  I  S  P           P  D  S  Y  Y  Y  Y  A  D  S  V  K  G  R  F  T  I  S  A  D  T  S  K  N  T  A
278.15.2         P  G  K  G  L  E  W  V  A  S  I  H  S  P        Y  D  G  Y  T  Y  Y  A  D  S  V  K  G  R  F  T  I  S  A  D  T  S  K  N  T  A
278.15.2.D54E    P  G  K  G  L  E  W  V  A  S  I  H  S  P        Y  E  G  Y  T  Y  Y  A  D  S  V  K  G  R  F  T  I  S  A  D  T  S  K  N  T  A
278.15.3         P  G  K  G  L  E  W  V  A  S  I  S  P           S  D  G  Y  T  Y  Y  A  D  S  V  K  G  R  F  T  I  S  A  D  T  S  K  N  T  A Kabat#          79 80 81 82  A  B  C 83 84 85 86 87 88 89 90 91 92 93 94 95 96 97 98 99 100  A  B  C 101 102 103 104 105 106 107 108 109 110 111 112 113
                                                                                        |_____Kabat-CDR H3_____|
                                                                                      |_____Chothia-CDR H3_____|
                                                                                      |_____Contact-CDR H3_____|
278.15           Y  L  Q  M  N  S  L  R  A  E  D  T  A  V  Y  Y  Y  C  A  R  Y  L  Y  W  S  Y  V           M  D  Y  W  G  Q  G  T  L  V  T  V  S  S
278.15.18        Y  L  Q  M  N  S  L  R  A  E  D  T  A  V  Y  Y  Y  C  A  R  Y  L  Y  W  S  Y  V           M  D  Y  W  G  Q  G  T  L  V  T  V  S  S
278.15.18.C55A   Y  L  Q  M  N  S  L  R  A  E  D  T  A  V  Y  Y  Y  C  A  R  Y  L  Y  W  S  Y  V           M  D  Y  W  G  Q  G  T  L  V  T  V  S  S
278.15.18.C55S   Y  L  Q  M  N  S  L  R  A  E  D  T  A  V  Y  Y  Y  C  A  R  Y  L  Y  W  S  Y  V           M  D  Y  W  G  Q  G  T  L  V  T  V  S  S
278.15.2         Y  L  Q  M  N  S  L  R  A  E  D  T  A  V  Y  Y  Y  C  A  R  Y  L  Y  W  S  Y  V           M  D  Y  W  G  Q  G  T  L  V  T  V  S  S
278.15.2.D54E    Y  L  Q  M  N  S  L  R  A  E  D  T  A  V  Y  Y  Y  C  A  R  Y  L  Y  W  S  Y  V           M  D  Y  W  G  Q  G  T  L  V  T  V  S  S
278.15.3         Y  L  Q  M  N  S  L  R  A  E  D  T  A  V  Y  Y  Y  C  A  R  Y  L  Y  W  S  Y  V           M  D  Y  W  G  Q  G  T  L  V  T  V  S  S
```

| Clone (Captured IgG) | rhIL17A (R&D) in Solution | | |
|---|---|---|---|
| | kon/(1/Ms) | koff/(1/s) | KD(M) |
| YW278.15.2 | *3.50E+07 | 3.90E-04 | 1.11E-11 |
| YW278.15.18 | *1.90E+07 | 2.60E-04 | 1.37E-11 |
| YW278.15.3 | *2.30E+07 | 3.50E-04 | 1.52E-11 |

| Clone (Captured IgG) | rhIL17F (R&D) in Solution | | |
|---|---|---|---|
| | ka1/(1/Ms) | kd1/(1/s) | KD(M) |
| YW278.15.2 | *2.00E+07 | 6.30E-04 | 3.15E-11 |
| YW278.15.18 | *2.60E+07 | 3.50E-04 | 1.35E-11 |
| YW278.15.3 | *1.20E+07 | 3.40E-04 | 2.83E-11 |

| Clone (Captured IgG) | cyno IL17F in Solution | | |
|---|---|---|---|
| | ka1/(1/Ms) | kd1/(1/s) | KD(M) |
| YW278.15.2 | *1.10E+07 | 2.30E-03 | 2.09E-10 |
| YW278.15.18 | *3.80E+06 | 2.40E-04 | 6.32E-11 |
| YW278.15.3 | *2.60E+06 | 2.00E-03 | 7.69E-10 |

| Clone (Captured IgG) | hIL17A/F in Solution | | |
|---|---|---|---|
| | ka1/(1/Ms) | kd1/(1/s) | KD(M) |
| YW278.15.2 | *2.60E+07 | 2.70E-04 | 1.04E-11 |
| YW278.15.18 | *1.50E+07 | 2.10E-04 | 1.40E-11 |
| YW278.15.3 | *2.40E+07 | 4.00E-04 | 1.67E-11 |

*close or above Biacore detection limit

FIG. 8A

| Clone (Captured IgG) | rhIL17A (R&D) in Solution | | |
|---|---|---|---|
| | kon/(1/Ms) | koff/(1/s) | KD(M) |
| YW278.15.2.D54E | *1.55E+07 | 2.86E-04 | 1.85E-11 |
| YW278.15.3 | *1.83E+07 | 4.42E-04 | 2.42E-11 |
| YW278.15.9 | *1.87E+07 | 2.89E-04 | 1.55E-11 |
| YW279.1.20 | | | NA |
| YW279.1.21 | *4.77E+05 | 2.43E-03 | 5.09E-09 |
| YW279.1.22 | *3.14E+06 | 3.70E-04 | 1.18E-10 |

| Clone (Captured IgG) | rhIL17F (R&D) in Solution | | |
|---|---|---|---|
| | ka1/(1/Ms) | kd1/(1/s) | KD(M) |
| YW278.15.2.D54E | *1.61E+07 | 1.94E-04 | 1.20E-11 |
| YW278.15.3 | *3.51E+06 | 4.05E-04 | 1.15E-10 |
| YW278.15.9 | *1.50E+07 | 2.72E-04 | 1.81E-11 |
| YW279.1.20 | *1.60E+06 | 2.55E-03 | 1.59E-09 |
| YW279.1.21 | *4.24E+06 | 3.49E-04 | 8.23E-11 |
| YW279.1.22 | *2.27E+06 | 4.00E-03 | 1.76E-09 |

| Clone (Captured IgG) | cyno IL17A in Solution | | |
|---|---|---|---|
| | ka1/(1/Ms) | kd1/(1/s) | KD(M) |
| YW278.15.2.D54E | *8.91E+06 | 2.69E-04 | 3.02E-11 |
| YW278.15.3 | *6.51E+06 | 4.91E-04 | 7.54E-11 |
| YW278.15.9 | *4.82E+06 | 2.41E-04 | 5.00E-11 |
| YW279.1.20 | 8.88E+05 | 2.20E-03 | 2.48E-09 |
| YW279.1.21 | 8.35E+05 | 1.51E-03 | 1.81E-09 |
| YW279.1.22 | *1.88E+06 | 4.50E-04 | 2.39E-10 |

| Clone (Captured IgG) | cyno IL17F in Solution | | |
|---|---|---|---|
| | ka1/(1/Ms) | kd1/(1/s) | KD(M) |
| YW278.15.2.D54E | 6.88E+06 | 1.40E-03 | 2.03E-10 |
| YW278.15.3 | 1.15E+06 | 2.00E-03 | 1.74E-09 |
| YW278.15.9 | 6.83E+06 | 6.11E-04 | 8.95E-11 |
| YW279.1.20 | | | NA |
| YW279.1.21 | 8.80E+05 | 2.96E-03 | 3.36E-09 |
| YW279.1.22 | 3.20E+05 | 2.84E-03 | 8.88E-09 |

| Clone (Captured IgG) | hIL17A/F in Solution | | |
|---|---|---|---|
| | ka1/(1/Ms) | kd1/(1/s) | KD(M) |
| YW278.15.2.D54E | 1.19E+07 | 6.41E-04 | 5.39E-11 |
| YW278.15.3 | 7.33E+06 | 6.85E-04 | 9.35E-11 |
| YW278.15.9 | 7.04E+06 | 1.61E-04 | 2.29E-11 |
| YW279.1.20 | | | NA |
| YW279.1.21 | 3.06E+05 | 3.60E-03 | 1.18E-08 |
| YW279.1.22 | 2.48E+06 | 1.71E-03 | 6.90E-10 |

*close or above Biacore detection limit

FIG. 8B

| Clone (Captured IgG) | rhIL17A (R&D) in Solution | | |
|---|---|---|---|
| | kon/(1/Ms) | koff/(1/s) | KD(M) |
| YW278.15.18.C55A | *2.00E+07 | 4.00E-04 | 2.00E-11 |
| YW278.15.18.C55S | *1.60E+07 | 3.70E-04 | 2.31E-11 |
| YW278.15.18 | *1.80E+07 | 3.40E-04 | 1.89E-11 |

| Clone (Captured IgG) | rhIL17F (R&D) in Solution | | |
|---|---|---|---|
| | ka1/(1/Ms) | kd1/(1/s) | KD(M) |
| YW278.15.18.C55A | *2.20E+07 | 4.10E-04 | 1.86E-11 |
| YW278.15.18.C55S | *2.10E+07 | 4.00E-04 | 1.90E-11 |
| YW278.15.18 | *1.10E+07 | 3.20E-04 | 2.91E-11 |

| Clone (Captured IgG) | cyno IL17F in Solution | | |
|---|---|---|---|
| | ka1/(1/Ms) | kd1/(1/s) | KD(M) |
| YW278.15.18.C55A | *5.20E+06 | 4.10E-04 | 7.88E-11 |
| YW278.15.18.C55S | *5.10E+06 | 3.40E-04 | 6.67E-11 |
| YW278.15.18 | *3.60E+06 | 3.10E-04 | 8.61E-11 |

| Clone (Captured IgG) | hIL17A/F in Solution | | |
|---|---|---|---|
| | ka1/(1/Ms) | kd1/(1/s) | KD(M) |
| YW278.15.18.C55A | 9.60E+06 | 2.70E-04 | 2.81E-11 |
| YW278.15.18.C55S | 1.20E+07 | 3.20E-04 | 2.67E-11 |
| YW278.15.18 | 1.20E+07 | 2.70E-04 | 2.25E-11 |

*close or above Biacore detection limit

FIG. 9

| Clone (Captured IgG) | rhesus IL17A (PUR17200) in Solution | | |
|---|---|---|---|
| | kon/(1/Ms) | koff/(1/s) | KD(M) |
| YW278.15.18.C55A | *9.00E+06 | 2.80E-04 | 3.11E-11 |
| YW278.15.18.C55S | *7.80E+06 | 4.50E-04 | 5.77E-11 |
| YW278.15.18 | *8.40E+06 | 3.20E-04 | 3.81E-11 |

*close or above Biacore detection limit

FIG. 10

| Kabat# | 1 2 3 4 5 6 7 8 9 10 11 12 13 14 15 16 17 18 19 20 21 22 23 24 25 26 27 A B C D E F 28 29 30 31 32 33 34 35 36 37 |
|---|---|
| | Kabat - CDR L1 |
| | Chothia - CDR L1 |
| | Contact - CDR L1 |
| YW264.21 | D I Q M T Q S P S S L S A S V G D R V T I T C R A S Q       S I S S Y L A W Y Q |
| YW265.01 | D I Q M T Q S P S S L S A S V G D R V T I T C R A S Q       S I S S Y L A W Y Q |

| Kabat# | 38 39 40 41 42 43 44 45 46 47 48 49 50 51 52 53 54 55 56 57 58 59 60 61 62 63 64 65 66 67 68 69 70 71 72 73 74 75 76 77 78 79 80 |
|---|---|
| | Kabat - CDR L2 |
| | Chothia - CDR L2 |
| | Contact - CDR L2 |
| YW264.21 | Q K P G K A P K L L I Y G A S S R A S G V P S R F S G S G S G T D F T L T I S S L Q P |
| YW265.01 | Q K P G K A P K L L I Y G A S S R A S G V P S R F S G S G S G T D F T L T I S S L Q P |

| Kabat# | 81 82 83 84 85 86 87 88 89 90 91 92 93 94 95 96 97 98 99 100 101 102 103 104 105 106 107 108 |
|---|---|
| | Kabat - CDR L3 |
| | Chothia - CDR L3 |
| | Contact - CDR L3 |
| YW264.21 | E D F A T Y Y C Q Q Y Y S S P L T F G Q G T K V E I K R |
| YW265.01 | E D F A T Y Y C Q Q Y Y S S P L T F G Q G T K V E I K R |

FIG. 11

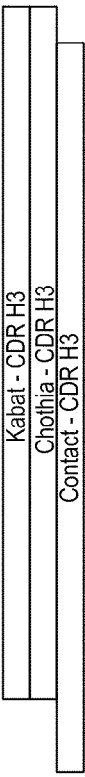
FIG. 12

IL17A: 5ng/ml or 0.16nm homodimer
IL17F: 50ng/ml or 1.7nm homodimer
IL17A/F: 25ng/ml or 0.78nm heterodimer
molar ratio means antibody to cytokine ratio

"--" DENOTES THAT AT THE CONCENTRATIONS USED THE ANTIBODIES DID NOT FULLY BLOCK.

| Antibody | IL17A | | | | IL17F | | | |
|---|---|---|---|---|---|---|---|---|
| | IC50 | | IC90 | | IC50 | | IC90 | |
| | nmol | molar ratio | nmol | molar ratio | nmol | molar ratio | nmol | molar ratio |
| 278.15.2 | 0.168 | 1.048 | 0.697 | 4.356 | 2.407 | 1.416 | 19.670 | 11.571 |
| 278.15.3 | 0.116 | 0.724 | 0.501 | 3.131 | 11.100 | 6.529 | 134.900 | 79.359 |
| 278.15.7 | 0.445 | 2.779 | 3.677 | 22.981 | 15.930 | 9.371 | 406.100 | 238.882 |
| 278.15.8 | 2.920 | 18.250 | 30.860 | 192.875 | 2.545 | 1.497 | 38.260 | 22.506 |
| 278.15.9 | 0.086 | 0.538 | 0.273 | 1.706 | 4.152 | 2.442 | 33.720 | 19.835 |
| 278.15.18 | 0.129 | 0.805 | 0.358 | 2.238 | 0.695 | 0.409 | 2.767 | 1.628 |
| 278.1.20 | 13.430 | 83.938 | 169.600 | 1060.000 | 1.842 | 1.084 | 7.630 | 4.488 |
| 278.1.21 | -- | -- | -- | -- | 42.570 | 25.041 | 784.600 | 461.529 |
| 278.1.22 | 0.776 | 4.850 | 6.606 | 41.288 | -- | -- | -- | -- |

| Antibody | IL17F | | | | IL17A/F | | | |
|---|---|---|---|---|---|---|---|---|
| | IC50 | | IC90 | | IC50 | | IC90 | |
| | nmol | molar ratio | nmol | molar ratio | nmol | molar ratio | nmol | molar ratio |
| 278.15.2 | 2.014 | 1.185 | 24.330 | 14.312 | 0.646 | 0.828 | 6.440 | 8.256 |
| 278.15.9 | 2.043 | 1.202 | 15.400 | 9.059 | | | | |
| 278.15.18 | 0.750 | 0.441 | 4.064 | 2.391 | 0.843 | 1.080 | 5.869 | 7.524 |

| Antibody | IL17A | | | | IL17F | | | | IL17A/F | | | |
|---|---|---|---|---|---|---|---|---|---|---|---|---|
| | IC50 | | IC90 | | IC50 | | IC90 | | IC50 | | IC90 | |
| | nmol | molar ratio | nmol | molar ratio | nmol | molar ratio | nmol | molar ratio | nmol | molar ratio | nmol | molar ratio |
| 278.15.2 | 0.092 | 0.575 | 0.679 | 4.244 | 1.880 | 1.106 | 9.550 | 5.618 | 1.110 | 1.423 | 5.960 | 7.641 |
| 278.15.2DJ4E | 0.243 | 1.519 | 1.413 | 8.831 | | | | | 1.280 | 1.641 | 9.140 | 11.718 |
| 278.15.18 | 0.074 | 0.463 | 0.246 | 1.538 | | | | | 1.240 | 1.590 | 7.160 | 9.179 |
| 278.15.18C55A | 0.046 | 0.288 | 0.313 | 1.956 | 0.770 | 0.453 | 3.360 | 1.976 | 0.890 | 1.141 | 5.840 | 7.487 |
| 278.15.18C55S | 0.051 | 0.319 | 0.186 | 1.163 | 0.540 | 0.318 | 2.380 | 1.400 | 1.140 | 1.462 | 7.970 | 10.218 |

FIG. 13A

|          |       | IL17F        |        |             |
|----------|-------|--------------|--------|-------------|
|          | IC50  |              | IC90   |             |
| Antibody | nmol  | molar ratio  | nmol   | molar ratio |
| 278.15.2 | 1.550 | 0.912        | 25.230 | 14.841      |
| 278.15.2DJ4E | 2.050 | 1.206    | 16.720 | 9.835       |
| 278.15.18 | 0.430 | 0.253       | 2.940  | 1.729       |
| 278.15.18C55A | 0.530 | 0.312   | 3.770  | 2.218       |
| 278.15.18C55S | 0.470 | 0.276   | 1.520  | 0.894       |

|          | IL17F |             |       |             | IL17A/F |             |       |             |
|----------|-------|-------------|-------|-------------|---------|-------------|-------|-------------|
|          | IC50  |             | IC90  |             | IC50    |             | IC90  |             |
| Antibody | nmol  | molar ratio | nmol  | molar ratio | nmol    | molar ratio | nmol  | molar ratio |
| 278.15.3 | 6.25  | 3.676       | 156.6 | 92.1        | 0.420   | 0.538       | 7.100 | 9.103       |

|          | IL17F |             |       |             |
|----------|-------|-------------|-------|-------------|
|          | IC50  |             | IC90  |             |
| Antibody | nmol  | molar ratio | nmol  | molar ratio |
| 278.15.3 | 0.063 | 0.396       | 0.358 | 2.238       |

FIG. 13B

| IL17A | ka (1/Ms) | kd (1/s) | KD (M) |
|---|---|---|---|
| YW264.21 | 2.70E+06 | 5.40E-04 | 2.00E-10 |
| Bi-specific | 1.60E+06 | 1.80E-04 | 1.10E-10 |

| IL17F | ka (1/Ms) | kd (1/s) | KD (M) |
|---|---|---|---|
| YW265.01 | 5.10E+05 | 3.20E-04 | 6.20E-10 |
| Bi-specific | 4.60E+05 | 3.30E-04 | 7.10E-10 |

FIG. 14

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | A | B | C | D | E | F | 28 | 29 | 30 | 31 | 32 | 33 | 34 | 35 | 36 | 37 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | | | | | | | | | | | | | | | | | | | |
| YW264.03 | D | I | Q | M | T | Q | S | P | S | S | L | S | A | S | V | G | D | R | V | T | I | T | C | R | A | S | Q | | | | | | | S | I | S | S | Y | L | A | W | Y | Q |
| YW264.21 | D | I | Q | M | T | Q | S | P | S | S | L | S | A | S | V | G | D | R | V | T | I | T | C | R | A | S | Q | | | | | | | S | I | S | S | Y | L | A | W | Y | Q |
| YW265.01 | D | I | Q | M | T | Q | S | P | S | S | L | S | A | S | V | G | D | R | V | T | I | T | C | R | A | S | Q | | | | | | | S | I | S | S | Y | L | A | W | Y | Q |

| Kabat# | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| YW264.03 | Q | K | P | G | K | A | P | K | L | L | I | Y | G | A | S | S | R | A | S | G | V | P | S | R | F | S | G | S | G | S | G | T | D | F | T | L | T | I | S | S | L | Q | P |
| YW264.21 | Q | K | P | G | K | A | P | K | L | L | I | Y | G | A | S | S | R | A | S | G | V | P | S | R | F | S | G | S | G | S | G | T | D | F | T | L | T | I | S | S | L | Q | P |
| YW265.01 | Q | K | P | G | K | A | P | K | L | L | I | Y | G | A | S | S | R | A | S | G | V | P | S | R | F | S | G | S | G | S | G | T | D | F | T | L | T | I | S | S | L | Q | P |

| Kabat# | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | 108 |
|---|---|---|---|---|---|---|---|---|---|---|---|---|---|---|---|---|---|---|---|---|---|---|---|---|---|---|---|---|
| YW264.03 | E | D | F | A | T | Y | Y | C | Q | Q | S | Y | S | S | P | L | T | F | G | Q | G | T | K | V | E | I | K | R |
| YW264.21 | E | D | F | A | T | Y | Y | C | Q | Q | Y | Y | S | S | P | L | T | F | G | Q | G | T | K | V | E | I | K | R |
| YW265.01 | E | D | F | A | T | Y | Y | C | Q | Q | Y | Y | S | S | P | L | T | F | G | Q | G | T | K | V | E | I | K | R |

```
Kabat#    1  2  3  4  5  6  7  8  9  10 11 12 13 14 15 16 17 18 19 20 21 22 23 24 25 26 27 28 29 30 31 32 33 34 35 36 37 38 39 40
                                                                                                    Chothia-CDR H1        Kabat-CDR H1
                                                                                                       Contact-CDR H1
YW264.03  E  V  Q  L  V  E  S  G  G  G  L  V  Q  P  G  G  S  L  R  L  S  C  A  A  S  G  F  S  F  S  S  Y  E  I  S  W  V  R  Q  A
YW264.21  E  V  Q  L  V  E  S  G  G  G  L  V  Q  P  G  G  S  L  R  L  S  C  A  A  S  G  F  S  F  T  S  Y  E  I  S  W  V  R  Q  A
YW265.01  E  V  Q  L  V  E  S  G  G  G  L  V  Q  P  G  G  S  L  R  L  S  C  A  A  S  G  Y  S  F  T  S  P  Y  I  S  W  V  R  Q  A Kabat#   41 42 43 44 45 46 47 48 49 50 51 52  A  B  C 53 54 55 56 57 58 59 60 61 62 63 64 65 66 67 68 69 70 71 72 73 74 75 76 77 78
                                                                Kabat-CDR H2
                                                       Chothia-CDR H2
                                        Contact-CDR H2
YW264.03  P  G  K  G  L  E  W  V  S  S  I  Y  A           Y  G  G  S  T  Y  Y  A  D  S  V  K  G  R  F  T  I  S  A  D  T  S  K  N  T  A
YW264.21  P  G  K  G  L  E  W  V  G  S  I  Y  L           W  G  G  S  T  Y  Y  A  D  S  V  K  G  R  F  T  I  S  A  D  T  S  K  N  T  A
YW265.01  P  G  K  G  L  E  W  V  A  S  I  F  Y           Y  S  G  A  T  D  Y  A  D  S  V  K  G  R  F  T  I  S  A  D  T  S  K  N  T  A Kabat#   79 80 81 82  A  B  C 83 84 85 86 87 88 89 90 91 92 93 94 95 96 97 98 99 100  A  B  C 101 102 103 104 105
                                                                                              Kabat-CDR H3
                                                                                           Chothia-CDR H3
                                                                                 Contact-CDR H3
YW264.03  Y  L  Q  M  N  S  L  R  A  E  D  T  A  V  Y  Y  Y  C  A  R  F  G  M  Y  S  R  W  K  T  Q  P  A                M  D  V  W  G  Q
YW264.21  Y  L  Q  M  N  S  L  R  A  E  D  T  A  V  Y  Y  Y  C  A  R  F  G  Q  R  Y  A                                  M  D  V  W  G  Q
YW265.01  Y  L  Q  M  N  S  L  R  A  E  D  T  A  V  Y  Y  Y  C  A  R  G  G  Y  N  Q  W  F  Y  S  I  Y  Q  S  Y  F  D  Y  W  G  Q
```

CROSS-REACTIVE AND BISPECIFIC ANTI-IL-17A/F ANTIBODIES

RELATED APPLICATIONS

The present application claims priority under 35 U.S.C. §119(e) to U.S. Provisional Application 61/164,709 filed Mar. 30, 2009, U.S. Provisional Application 61/112,644 filed Nov. 7, 2008, and U.S. Provisional Application 61/093,212 filed Aug. 29, 2008, each of which is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Jan. 6, 2012, is named GNE-0341 Seq_Listing.txt and is 69,681 bytes in size.

FIELD OF THE INVENTION

The present invention relates generally to antibodies cross-reactive with IL-17A and IL-17F, and bispecific anti-IL-17A/F antibodies, and their uses.

BACKGROUND OF THE INVENTION

Interleukin-17 (IL-17) is a T-cell derived pro-inflammatory molecule that stimulates epithelial, endothelial and fibroblastic cells to produce other inflammatory cytokines and chemokines including IL-6, IL-8, G-CSF, and MCP-1 [see, Yao, Z. et al., J. Immunol., 122(12):5483-5486 (1995); Yao, Z. et al, Immunity, 3(6):811-821 (1995); Fossiez, F., et al., J. Exp. Med., 183(6): 2593-2603 (1996); Kennedy, J., et al., *J. Interferon Cytokine Res.*, 16(8):611-7 (1996); Cai, X. Y., et al., *Immunol. Lett*, 62(1):51-8 (1998); Jovanovic, D. V., et al., *J. Immunol.*, 160(7):3513-21 (1998); Laan, M., et al., *J. Immunol.*, 162(4):2347-52 (1999); Linden, A., et al., *Eur Respir J*, 15(5):973-7 (2000); and Aggarwal, S. and Gurney, A. L., *J Leukoc Biol.* 71(1):1-8 (2002)]. IL-17 also synergizes with other cytokines including TNF-α and IL-1β to further induce chemokine expression (Chabaud, M., et al., *J. Immunol.* 161(1):409-14 (1998)). Interleukin 17 (IL-17) exhibits pleitropic biological activities on various types of cells. IL-17 also has the ability to induce ICAM-1 surface expression, proliferation of T cells, and growth and differentiation of CD34$^+$ human progenitors into neutrophils. IL-17 has also been implicated in bone metabolism, and has been suggested to play an important role in pathological conditions characterized by the presence of activated T cells and TNF-α production such as rheumatoid arthritis and loosening of bone implants (Van Bezooijen et al., *J. Bone Miner. Res.*, 14: 1513-1521 [1999]). Activated T cells of synovial tissue derived from rheumatoid arthritis patients were found to secrete higher amounts of IL-17 than those derived from normal individuals or osteoarthritis patients (Chabaud et al., *Arthritis Rheum.*, 42: 963-970 [1999]). It was suggested that this proinflammatory cytokine actively contributes to synovial inflammation in rheumatoid arthritis. Apart from its proinflammatory role, IL-17 seems to contribute to the pathology of rheumatoid arthritis by yet another mechanism. For example, IL-17 has been shown to induce the expression of osteoclast differentiation factor (ODF) mRNA in osteoblasts (Kotake et al., *J. Clin. Invest.*, 103: 1345-1352 [1999]). ODF stimulates differentiation of progenitor cells into osteoclasts, the cells involved in bone resorption. Since the level of IL-17 is significantly increased in synovial fluid of rheumatoid arthritis patients, it appears that IL-17 induced osteoclast formation plays a crucial role in bone resorption in rheumatoid arthritis. IL-17 is also believed to play a key role in certain other autoimmune disorders such as multiple sclerosis (Matusevicius et al., *Mult. Scler.*, 5: 101-104 (1999); Kurasawa, K., et al., *Arthritis Rheu* 43(11):2455-63 (2000)) and psoriasis (Teunissen, M. B., et al., *J Invest Dermatol* 111(4):645-9 (1998); Albanesi, C., et al., *J Invest Dermatol* 115(1):81-7 (2000); and Homey, B., et al., J. Immunol. 164(12:6621-32 (2000)).

IL-17 has further been shown, by intracellular signalling, to stimulate Ca$^{2+}$ influx and a reduction in [cAMP]$_i$ in human macrophages (Jovanovic et al, *J. Immunol.*, 160:3513 [1998]). Fibroblasts treated with IL-17 induce the activation of NF-κB, [Yao et al., *Immunity*, 3:811 (1995), Jovanovic et al., supra], while macrophages treated with it activate NF-κB and mitogen-activated protein kinases (Shalom-Barek et al, *J. Biol. Chem.*, 273:27467 [1998]). Additionally, IL-17 also shares sequence similarity with mammalian cytokine-like factor 7 that is involved in bone and cartilage growth. Other proteins with which IL-17 polypeptides share sequence similarity are human embryo-derived interleukin-related factor (EDIRF) and interleukin-20.

Consistent with IL-17's wide-range of effects, the cell surface receptor for IL-17 has been found to be widely expressed in many tissues and cell types (Yao et al., *Cytokine*, 2:794 [1997]). While the amino acid sequence of the human IL-17 receptor (IL-R) (866 amino acids) predicts a protein with a single transmembrane domain and a long, 525 amino acid intracellular domain, the receptor sequence is unique and is not similar to that of any of the receptors from the cytokine/growth factor receptor family. This coupled with the lack of similarity of IL-17 itself to other known proteins indicates that IL-17 and its receptor may be part of a novel family of signaling proteins and receptors. It has been demonstrated that IL-17 activity is mediated through binding to its unique cell surface receptor (designated herein as human IL-17R), wherein previous studies have shown that contacting T cells with a soluble form of the IL-17 receptor polypeptide inhibited T cell proliferation and IL-2 production induced by PHA, concanavalin A and anti-TCR monoclonal antibody (Yao et al., *J. Immunol.*, 155:5483-5486 [1995]). As such, there is significant interest in identifying and characterizing novel polypeptides having homology to the known cytokine receptors, specifically IL-17 receptors.

Interleukin 17 is now recognized as the prototype member of an emerging family of cytokines. The large scale sequencing of the human and other vertebrate genomes has revealed the presence of additional genes encoding proteins clearly related to IL-17, thus defining a new family of cytokines. There are at least 6 members of the IL-17 family in humans and mice including IL-17B, IL-17C, IL-17D, IL-17E and IL-17F as well as novel receptors IL-17RH1, IL-17RH2, IL-17RH3 and IL-17RH4 (see WO 01/46420 published Jun. 28, 2001). One such IL-17 member (designated as IL-17F) has been demonstrated to bind to the human IL-17 receptor (IL-17R) (Yao et al., *Cytokine*, 9(11):794-800 (1997)). Initial characterization suggests that, like IL-17, several of these newly identified molecules have the ability to modulate immune function. The potent inflammatory actions that have been identified for several of these factors and the emerging associations with major human diseases suggest that these proteins may have significant roles in inflammatory processes and may offer opportunities for therapeutic intervention.

The gene encoding human IL-17F is located adjacent to IL-17 (Hymowitz, S. G., et al., *Embo J*, 20(19):5332-41

(2001)). IL-17 and IL-17F share 44% amino acid identity whereas the other members of the IL-17 family share a more limited 15-27% amino acid identity suggesting that IL-17 and IL-17F form a distinct subgroup within the IL-17 family (Starnes, T., et al., *J Immunol.* 167(8):4137-40 (2001); Aggarwal, S. and Gurney, A. L., *J. Leukoc Biol,* 71(1):1-8 (2002)). IL-17F appears to have similar biological actions as IL-17, and is able to promote the production of IL-6, IL-8, and G-CSF from a wide variety of cells. Similar to IL-17, it is able to induce cartilage matrix release and inhibit new cartilage matrix synthesis (see U.S.-2002-0177188-A1 published Nov. 28, 2002). Thus, like IL-17, IL-17F may potentially contribute to the pathology of inflammatory disorders. Recently, these authors have observed that both IL-17 and IL-17F are induced in T cells by the action of interleukin 23 (IL-23) (Aggarwal, S., et al., *J. Biol. Chem.,* 278(3):1910-4 (2003)). The observation that IL-17 and IL-17F share similar chromosomal localization and significant sequence similarity sd well as the observation that IL-17 and IL-17F appear to be induced with the same cell population in response to a specific stimuli has lead to the identification of a new human cytokine that is comprised of a covalent heterodimer of IL-17 and IL-17F (herein designated IL-17A/F).

IL-17A and IL-17F are now recognized as major proinflammatory cytokines secreted by Th17T cell subset. They target almost all cell types in body and induce inflammation and tissue damage.

Human IL-17A/F is a distinctly new cytokine, distinguishable from human IL-17 and IL-17F in both protein structure and in cell-based activity assays. Through the use of purified recombinant human IL-17A/F as a standard, a human IL-17A/F-specific ELISA has been developed. Through the use of this specific ELISA, the induced expression of human IL-17A/F was detected, confirming that IL-17A/F is naturally produced from activated human T cells in culture. Hence, IL-17A/F is a distinctly new cytokine, detectable as a natural product of isolated activated human T cells, whose recombinant form has been characterized, in both protein structure and cell-based assays, as to be different and distinguishable from related cytokines.

IL-17A/F is disclosed in U.S. Application Publication Nos. 20060270003, published Nov. 30, 2006, and 20070160576, published Jul. 12, 2007. IL-17A/F has been described to as a target for treating various immune-mediated diseases (Chang and Dong, *Cell Res.* 17(5):435-40 (2007)); an IL-17A/F protein produced by mouse Th17 cells has been shown to induce airway neutrophil recruitment and thus having an in vivo function in airway neutrophilia (Liang et al., *J Immunol* 179 (11):7791-9 (2007)); and the human IL-17A/F heterodimeric cytokine has been reported to signal through the IL-17RA/IL-17RC receptor complex (Wright et al., *J Immunol* 181(4): 2799-805 (2008)).

In view of the proinflammatory properties of both IL-17A and IL-17F, it would be desirable to generate cross-reactive and bispecific antibodies that can block both IL-17A and IL-17F with high potency. Such cross-reactive and bispecific antibodies provide new therapeutic opportunities in the treatment of inflammatory and immune-related diseases, including autoimmune diseases, and in the treatment of cancer.

SUMMARY OF THE INVENTION

The present invention is based, at least in part, on the production and characterization of antibodies cross-reactive with both IL-17A and IL-17F. The invention further concerns bispecific antibodies binding both to IL-17A and IL-17F.

In one aspect, the invention concerns an antibody comprising an antigen-binding domain that binds to IL-17A and IL-17F and inhibits a biological function of both IL-17A and IL-17F, or a functional fragment thereof, where the biological function can, for example, be proinflammatory activity.

In one embodiment, the antibody comprises a light chain variable domain comprising CDRL1, CDRL2, and CDRL3 regions, wherein at least one of the CDRL1, CDRL2, and CDRL3 regions is selected from the group consisting of:

(a) CDRL1 comprising the sequence DVSTAVA (SEQ ID NO: 24) or SISSYLA (SEQ ID NO: 25), (b) CDRL2 comprising the sequence SASFLYS (SEQ ID NO: 26) or GASSRAS (SEQ ID NO: 27), and (c) CDRL3 comprising the sequence SYTTPPT (SEQ ID NO: 28) or RYSQPIT (SEQ ID NO: 29), or an affinity matured variant thereof, or a functional fragment of the antibody or the affinity matured variant.

In another embodiment, each of the CDRL1, CDRL2, and CDRL3 regions is selected from the group consisting of:

(a) CDRL1 comprising the sequence DVSTAVA (SEQ ID NO: 24) or SISSYLA (SEQ ID NO: 25), (b) CDRL2 comprising the sequence SASFLYS (SEQ ID NO: 26) or GASSRAS (SEQ ID NO: 27), and (c) CDRL3 comprising the sequence SYTTPPT (SEQ ID NO: 28) or RYSQPIT (SEQ ID NO: 29).

In another embodiment, (a) CDRL1 comprises the sequence DVSTAVA (SEQ ID NO: 24), (b) CDRL2 comprises the sequence SASFLYS (SEQ ID NO: 26), and (c) CDRL3 comprises the sequence SYTTPPT (SEQ ID NO: 28).

In yet another embodiment, (a) CDRL1 comprises the sequence SISSYLA (SEQ ID NO: 25), (b) CDRL2 comprises the sequence GASSRAS (SEQ ID NO 27), and (c) CDRL3 comprises the sequence RYSQPIT (SEQ ID NO: 29).

In a further embodiment, in the affinity matured variant CDRL3 comprises the sequence SYTAKLT (SEQ ID NO: 30).

In a still further embodiment, in the affinity matured variant (a) CDRL1 comprises the sequence DVSTAVA (SEQ ID NO: 24), and (b) CDRL2 comprises the sequence SASFLYS (SEQ ID NO: 26, and CDRL3 may comprise the sequence YYIYPAT (SEQ ID NO: 31), or a functional fragment thereof.

In yet another embodiment, in the affinity matured variant (a) CDRL1 comprises the sequence DVSTAVA (SEQ ID NO: 24), and (b) CDRL2 comprises the sequence SASFLYS (SEQ ID NO: 26), and CDRL3 may comprise the sequence HNDLPLT (SEQ ID NO: 32).

In an additional embodiment, in the affinity matured variant (a) CDRL1 comprises the sequence VISSSLA (SEQ ID NO: 33), and (b) CDRL2 comprises the sequence GASFLYS (SEQ ID NO: 34).

In another embodiment, in the affinity matured variant CDRL3 comprises the sequence SYTPRST (SEQ ID NO: 75), or a functional fragment thereof.

In yet another embodiment, in the affinity mature variant
   (a) CDRL1 comprises the sequence DVSTAVA (SEQ ID NO: 24); and
   (b) CDR2 comprises the sequence SASFLYS (SEQ IS NO: 26).

In a further embodiment, in the affinity matured variant CDRL3 comprises the sequence QYYSTTTT (SEQ ID NO: 76), or a functional fragment thereof.

In a still further embodiment, in the affinity matured variant
   (a) CDRL1 comprises the sequence DVSTAVA (SEQ ID NO: 24); and
   (b) CDR2 comprises the sequence SASFLYS (SEQ ID NOT: 26).

In a different embodiment, in the affinity matured variant CDRL3 comprises the sequence QQSQNPQTT (SEQ ID NO: 77), or a functional fragment thereof.

In an additional embodiment, in the affinity matured variant
   (a) CDRL1 comprises the sequence DVSTAVA (SEQ ID NO: 24); and
   (b) CDRL2 comprises the sequence SASFLYS (SEQ ID NO: 26).

In another embodiment, in the affinity matured variant CDRL3 comprises the sequence RFSQHIT (SEQ ID NO:78), or a functional fragment thereof.

In yet another embodiment, in the affinity matured variant
   (a) CDRL1 comprises the sequence RIKRYLA (SEQ ID NO: 89); and
   (b) CDRL2 comprises the sequence GASSRAS (SEQ ID NO: 27).

In a further embodiment, in the affinity matured variant CDRL3 comprises the sequence RYSWHTT (SEQ ID NO:79), or a functional fragment thereof.

In a still further embodiment, in the affinity matured variant
   (a) CDRL1 comprises the sequence SISSYLA (SEQ ID NO: 25); and
   (b) CDRL2 comprises the sequence GASSRAS (SEQ ID NO: 27).

In a different embodiment, in the affinity matured variant CDRL3 comprises the sequence RYSLPIT (SEQ ID NO:80), or a functional fragment thereof.

In yet another embodiment, in the affinity matured variant
   (a) CDRL1 comprises the sequence SISSYLA (SEQ ID NO: 25); and
   (b) CDRL2 comprises the sequence GASSRAS (SEQ ID NO: 27).

In further embodiments, the antibody comprises a heavy chain variable domain comprising CDRH1, CDRH2, and CDRH3 regions, wherein at least one of the CDRH1, CDRH2, and CDRH3 regions is selected from the group consisting of:
   (a) CDRH1 comprising a sequence selected from the group consisting of GFTFTDYDIS (SEQ ID NO: 35), GFSFIDYDIS (SEQ ID NO: 36), GFSFTSYMMS (SEQ ID NO: 81), GFSFPSYFIS (SEQ ID NO: 82); and GFTFYDYDIS (SEQ ID NO: 88);
   (b) CDRH2 comprising a sequence selected from the group consisting of SDGYTYYADSVKG (SEQ ID NO: 37), PDCYTYYADSVKG (SEQ ID NO: 38), PDAYTY PDCYTYYADSVKG (SEQ ID NO: 39), PDSYTTYYADSVKG (SEQ ID NO: 90), YDGYTYYADSVKG (SEQ ID NO: 41), YEGYTYYADSVKG (SEQ ID NO: 44), ESGATDYADSVKG (SEQ ID NO: 83), VSGATVYADSVKG (SEQ ID NO: 84) YDGYAYYADSVKG (SEQ ID NO: 85); and LDGYSYYADSVKG (SEQ ID NO: 86); and; and
   (c) CDRH3 comprising a sequence YLYWSYV (SEQ ID NO: 40), and EGYYYSTSIKYYPW (SEQ ID NO: 87),
   or a functional fragment thereof.

In still further embodiments, the antibody comprises a heavy chain variable domain comprising CDRH1, CDRH2, and CDRH3 regions, wherein each of the CDRH1, CDRH2, and CDRH3 regions is selected from the group consisting of:
   (a) CDRH1 comprising a sequence selected from the group consisting of GFTFTDYDIS (SEQ ID NO: 35), GFSFIDYDIS (SEQ ID NO: 36), GFSFTSYMMS (SEQ ID NO: 81), and GFSFPSYFIS (SEQ ID NO: 82),
   (b) CDRH2 comprising a sequence selected from the group consisting of SDGYTYYADSVKG (SEQ ID NO: 37), PDCYTYYADSVKG (SEQ ID NO: 38), PDAYTY PDCYTYYADSVKG (SEQ ID NO: 39), PDSYTTYYADSVKG (SEQ ID NO: 90), YDGYTYYADSVKG (SEQ ID NO: 41), YEGYTYYADSVKG (SEQ ID NO: 44), ESGATDYADSVKG (SEQ ID NO: 83), and VSGATVYADSVKG (SEQ ID NO: 84); and
   (c) CDRH3 comprising a sequence YLYWSYV (SEQ ID NO: 40), or EGYYYSTSIKYYPW (SEQ ID NO: 87),
   or a functional fragment thereof.

In another embodiment, the invention is directed to an antibody which comprises CDRH1, CDRH2 and CDRH3 regions wherein
   (a) CDRL1 comprises the sequence DVSTAVA (SEQ ID NO: 24),
   (b) CDRL2 comprises the sequence SASFLYS (SEQ ID NO: 26),
   (c) CDRL3 comprises the sequence SYTTPPT (SEQ ID NO: 28), and
   (d) CDRH1 comprises the sequence GFTFTDYDIS (SEQ ID NO: 35),
   (e) CDRH2 comprises the sequence SDGYTYYADSVKG (SEQ ID NO: 37), and
   (f) CDRH3 comprises the sequence YLYWSYV (SEQ ID NO: 40),
   or a functional fragment thereof.

In yet another embodiment, the invention is directed to an antibody which comprises CDRH1, CDRH2 and CDRH3 regions wherein
   (a) CDRL1 comprises the sequence SISSYLA (SEQ ID NO: 25),
   (b) CDRL2 comprises the sequence GASSRAS (SEQ ID NO: 27),
   (c) CDR3 comprises the sequence RYSQPIT (SEQ ID NO: 29),
   (d) CDRH1 comprises the sequence GFTFTDYDIS (SEQ ID NO: 35),
   (e) CDRH2 comprises the sequence SDGYTYYADSVKG (SEQ ID NO: 37), and
   (f) CDRH3 comprises the sequence YLYWSYV (SEQ ID NO: 40),
   or a functional fragment thereof.

In a further embodiment, the antibody further comprises CDRH1, CDRH2 and CDRH3 regions wherein
   (d) CDRH1 comprises the sequence GFSFIDYDIS (SEQ ID NO: 36),
   (e) CDRH2 comprises the sequence PDCYTYYADSVKG (SEQ ID NO: 38), and
   (f) CDRH3 comprises the sequence YLYWSYV (SEQ ID NO: 40).

In a still further embodiment, the antibody further comprises CDRH1, CDRH2 and CDRH3 regions wherein
   (d) CDRH1 comprises the sequence SFSGIDYDIS (SEQ ID NO: 91), (e) CDRH2 comprises the sequence YDGYTYYADSVKG (SEQ ID NO: 41), and (f) CDRH3 comprises the sequence YLYWSYV (SEQ ID NO: 40).

In an additional embodiment, the antibody further comprises CDRH1, CDRH2 and CDRH3 regions wherein (d) CDRH1 comprises the sequence GFTFTDYDIS (SEQ ID NO: 35), (e) CDRH2 comprises the sequence SDGYTYYADSVKG (SEQ ID NO: 37), and (f) CDRH3 comprises the sequence YLYWSYV (SEQ ID NO: 40).

In another embodiment, the antibody further comprises CDRH1, CDRH2 and CDRH3 regions wherein (d) CDRH1 comprises the sequence GFSFIDYDIS (SEQ ID NO: 36), (e) CDRH2 comprises the sequence PDAYTYYADSVKG (SEQ ID NO: 42), and (f) CDRH3 comprises the sequence YLYWSYV (SEQ ID NO: 40).

In yet another embodiment, the antibody further comprises CDRH1, CDRH2 and CDRH3 regions wherein (d) CDRH1 comprises the sequence GFSFIDYDIS (SEQ ID NO: 36), (e) CDRH2 comprises the sequence PDSYTYYADSVKG (SEQ ID NO: 43), and (f) CDRH3 comprises the sequence YLYWSYV (SEQ ID NO: 40).

In a further embodiment, the antibody further comprises CDRH1, CDRH2 and CDRH3 regions wherein (d) CDRH1 comprises the sequence SFSGIDYDIS (SEQ ID NO: 91), (e) CDRH2 comprises the sequence YEGYTYYADSVKG (SEQ ID NO: 44), and (f) CDRH3 comprises the sequence YLYWSYV (SEQ ID NO: 40).

In another embodiment, the antibody binds essentially the same epitope of IL-17A and IL-17F as a cross-reactive antibody selected from the group consisting of YW241.47, YW278.15, YW279.1, or an affinity matured variant thereof, or a functional fragment of such antibody or such affinity matured variant.

In yet another embodiment, the affinity matured variant is selected from the group consisting of antibodies YW278.15.18, YW 178.15.2, YW 278.15.3, YW 278.15.18C55A, YW 278.15.18C55S, and YW 278.15.2.D54E.

In a further embodiment, the antibody comprises an antigen-binding domain that binds to IL-17A and IL-17F with substantially the same binding affinity, or a functional fragment thereof.

In a still further embodiment, the antibody comprises an antigen-binding domain that binds to IL-17A and IL-17F with a binding affinity of at least about $10^{-10}$ to $10^{-11}$M, or a functional fragment thereof.

In an additional embodiment, the invention concerns an antibody comprising an antigen-binding domain that binds to IL-17A and IL-17F both as a monomer and a homodimer or a heterodimer, or a functional fragment thereof.

In a further embodiment, the invention concerns an antibody which binds both human IL-17A/F and IL-17A/F of a non-human primate, or a functional fragment thereof. The non-human primate can, for example, be a Cynomolgus (Cyno) or Rhesus monkey. In another embodiment, the antibody binds to human IL-17A/F and optionally a non-human primate IL-17A/F but does not bind a rodent, e.g. rat or mouse, IL-17A/F.

In a still further embodiment, the antibody is capable of reducing demyelination in an inflammatory or immune related disease.

The antibodies of the invention can be monoclonal, and can be chimeric, humanized or human.

The antibody fragments of the invention include, without limitation, Fab, Fab', F(ab')$_2$, and Fv fragments; diabodies; linear antibodies; single-chain antibody molecules; and multispecific antibodies formed from antibody fragments.

In a different aspect, the invention concerns a bispecific antibody comprising a first antigen binding site that binds to IL-17A and a second antigen binding site that binds to IL-17F, wherein (1) the first antigen binding site comprises a first heavy chain variable domain comprising CDRH1, CDRH2, and CDRH3 regions, wherein at least one of the CDRH1, CDRH2 and CDRH3 regions is selected from the group consisting of (a) CDRH1 comprising the sequence TSYEIS (SEQ ID NO: 45), (b) CDRH2 comprising the sequence WVGSIYLWGG (SEQ ID NO: 46), and (c) CDRH3 comprising the sequence ARFGQRYA (SEQ ID NO: 47), and (2) the second antigen binding site comprises a second heavy chain variable domain comprising CDRH1, CDRH2, and CDRH3 regions, wherein at least one of the CDRH1, CDRH2 and CDRH3 regions is selected from the group consisting of (a) CDRH1 comprising the sequence TSPYIS (SEQ ID NO: 48), (b) CDRH2 comprising the sequence WVASIFYYSG (SEQ ID NO: 49), and (c) CDRH3 comprising the sequence ARGGYGYNQW-FYSIYQSY (SEQ ID NO: 50), or an affinity matured variant thereof, or a functional fragment of the antibody or affinity matured variant.

In one embodiment, the bispecific antibody comprises CDRH1, CDRH2, and CDRH3 regions, wherein (1) in the first antigen binding site (a) CDRH1 comprises the sequence TSYEIS (SEQ ID NO: 45), (b) CDRH2 comprises the sequence WVGSIYLWGG (SEQ ID NO: 46), and (c) CDRH3 comprises the sequence ARFGQRYA (SEQ ID NO: 47), and (2) in the second antigen binding site (a) CDRH1 comprises the sequence TSPYIS (SEQ ID NO: 48), (b) CDRH2 comprises the sequence WVASIFYYSG (SEQ ID NO: 49), and (c) CDRH3 comprises the sequence ARGGYGYNQW-FYSIYQSY (SEQ ID NO: 50), or an affinity matured variant thereof, or a functional fragment of the antibody or affinity matured variant.

In another embodiment, the bispecific antibody further comprises a light chain variable domain comprising CDRL1, CDRL2, and CDRL3 regions, wherein at least one of the CDRL1, CDRL2, and CDRL3 regions is selected from the group consisting of:

(a) CDRL1 comprising the sequence SISSYLA (SEQ ID NO: 25), (b) CDRL2 comprising the sequence GASSRAS (SEQ ID NO: 27), and (c) CDRL3 comprising the sequence YYSSPLT (Residues 91-97 of SEQ ID NO: 21), or an affinity matured variant thereof, or a functional fragment of the antibody or affinity matured variant.

In yet another embodiment, in the light chain variable domain of the bispecific antibody or an affinity matured variant thereof, or a functional fragment of the antibody or the affinity matured variant (a) CDRL1 comprises the sequence SISSYLA (SEQ ID NO: 25), (b) CDRL2 comprises the sequence GASSRAS (SEQ ID NO: 27), and (c) CDRL3 comprises the sequence YYSSPLT (Residues 91-97 of SEQ ID NO: 21).

In a further embodiment, the bispecific antibody, or functional fragment thereof, binds to IL-17A and IL-17F with substantially the same binding affinity.

In a still further embodiment, the bispecific antibody, or functional fragment thereof, binds to IL-17A and IL-17F with a binding affinity of at least about $10^{-10}$ to $10^{-11}$ M.

In an additional embodiment, the bispecific antibody, or functional fragment thereof, binds to IL-17A and IL-17F both as a monomer and a homodimer or a heterodimer.

In yet another embodiment, the bispecific antibody, or functional fragment thereof, binds both human and non-human primate IL-17A/F, wherein the non-human primate may, for example, be a Cynomolgus (Cyno) or Rhesus monkey. In another embodiment, the antibody binds to human IL-17A/F and optionally a non-human primate IL-17A/F but does not bind a rodent, e.g. rat or mouse, IL-17A/F.

In a different embodiment, the bispecific antibody, or functional fragment thereof, is capable of reducing demyelination in an inflammatory or immune related disease.

Just as before, the bispecific antibody can also be monoclonal, chimeric, humanized or human, and the antibody fragments include, without limitation, Fab, Fab', F(ab')$_2$, and Fv fragments; diabodies; linear antibodies; single-chain antibody molecules; and multispecific antibodies formed from antibody fragments.

In a different aspect, the invention concerns cross-reactive and bispecific antibodies as hereinabove described, which inhibit a biological function of IL-17A in an antibody to IL-17A molar ratio of about 10:1 to about 1:10, or about 5:1 to about 1:5, or about 1:1 to about 1:5, or about 1:1 to about 1, or about 1:1 to about 1:2, where IL-17A stands for an IL-17A homodimer.

In a further aspect, the invention concerns cross-reactive and bispecific antibodies as hereinabove described, which inhibit a biological function of IL-17F in an antibody to IL-17F molar ratio of about 10:1 to about 1:10, or about 5:1 to about 1:5, or about 1:1 to about 1:5, or about 1:1 to about 1:3, or about 1:1 to about 1:2, where IL-17F stands for an IL-17F homodimer.

In a still further aspect, the invention concerns cross-reactive and bispecific antibodies as hereinabove described, which inhibit a biological function of IL-17A and IL-17F in the form of a heterodimer in an antibody to heterodimer molar ratio of about 10:1 to about 1:10, or about 5:1 to about 1:5, or about 1:1 to about 1:5, or about 1:1 to about 1:3, or about 1:1 to about 1:2.

In another aspect, the invention concerns an isolated nucleic acid molecule encoding a light chain of a cross-reactive or bispecific antibody or antibody fragment as hereinabove described.

In yet another aspect, the invention concerns a recombinant host cell comprising a nucleic acid molecule encoding a light chain of a cross-reactive or bispecific antibody or antibody fragment as hereinabove described. The host cell can be eukaryotic or prokaryotic, including, for example, Chinese hamster Ovary (CHO) cells and E. coli cells.

The invention further concerns a pharmaceutical composition comprising a cross-reactive or bispecific antibody or antibody fragment as hereinabove described in admixture with a pharmaceutically acceptable excipient.

In addition, the invention concerns a method for the treatment of an inflammatory or immune related disease comprising administering to a mammalian subject in need an effective amount of a cross-reactive or bispecific antibody of the present invention, or a functional fragment thereof. The mammalian subject preferably is a human patient.

The inflammatory or immune related condition may, for example, be selected from the group consisting of systemic lupus erythematosis, rheumatoid arthritis, juvenile chronic arthritis, spondyloarthropathies, systemic sclerosis (scleroderma), idiopathic inflammatory myopathies (dermatomyositis, polymyositis), Sjogren's syndrome, systemic vasculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic demyelinating polyneuropathy or Guillain-Barre syndrome, and chronic inflammatory demyelinating polyneuropathy, hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis, inflammatory bowel disease (IBD), including ulcerative colitis: Crohn's disease, gluten-sensitive enteropathy, and Whipple's disease, autoimmune or immune-mediated skin diseases including bullous skin diseases, erythema multiforme and contact dermatitis, psoriasis, allergic diseases such as asthma, allergic rhinitis, atopic dermatitis, food hypersensitivity and urticaria, immunologic diseases of the lung such as eosinophilic pneumonia, idiopathic pulmonary fibrosis and hypersensitivity pneumonitis, transplantation associated diseases including graft rejection and graft-versus-host-disease. Infectious diseases including viral diseases such as AIDS (HIV infection), hepatitis A, B, C, D, and E, herpes, etc., bacterial infections, fungal infections, protozoal infections and parasitic infections.

In a preferred embodiment, the inflammatory or immune related disease is selected from the group consisting of rheumatoid arthritis (RA), inflammatory bowel disease (IBD) and asthma.

In as still further aspect, the invention concerns an article of manufacture, comprising: (a) a container; (b) a label on the container; and (c) a composition of matter comprising a cross-reactive or bispecific antibody of the present invention, contained with the container, wherein the label on said container indicates that the composition of matter can be used for treating an inflammatory or an immune related disease.

The invention further concerns the use of an antibody herein in the preparation of a medicament for the treatment of an inflammatory or an immune related disease.

BRIEF DESCRIPTION OF THE DRAWINGS

FIG. 1 shows a nucleotide sequence (SEQ ID NO:1) of a native sequence human IL-17A cDNA.

FIG. 2 shows the amino acid sequence (SEQ ID NO:2) derived from the coding sequence of SEQ ID NO:1 shown in FIG. 1.

FIG. 3 shows a nucleotide sequence (SEQ ID NO:3) of a native sequence human IL-17F cDNA.

FIG. 4 shows the amino acid sequence (SEQ ID NO:4) derived from the coding sequence of SEQ ID NO:3 shown in FIG. 3.

FIG. 5A shows the alignment of light chain sequences of IL-17A/F cross-reactive antibodies YW 248.65, YW240.27, YW 241.47, YW 271.25, YW 278.15, YW 278.27, YW 278.57, YW 278.60, YW 279.1, and YW 280.3 (SEQ ID NOs: 5-14).

FIG. 5B shows the alignment of heavy chain sequences of IL-17A/F cross-reactive antibodies YW 248.65, YW240.27, YW 241.47, YW 271.25, YW 278.15, YW 278.27, YW 278.57, YW 278.60, YW 279.1, and YW 280.3 (SEQ I NOs: 51-60).

FIG. 5C shows the alignment of light chain sequences of IL-17A/F cross-reactive antibodies YW 278.15.7, YW 278.15.8, YW 278.15.9, YW 279.1.20, YW 279.1.21, and YW 279.1.22 (SEQ ID Nos: 63-68).

FIG. 5D shows the alignment of heavy chain sequences of IL-17A/F cross-reactive antibodies YW 278.15.7, YW 278.15.8, YW 278.15.9, YW 279.1.20, YW 279.1.21, and YW 279.1.22 (SEQ ID Nos: 69-74).

FIG. 6 shows the alignment of light chain sequences of IL-17A/F cross-reactive antibody YW278.15 (SEQ ID NO: 9) and its affinity matured variants, YW278.15.18 (SEQ ID NO: 15), YW278.15.2 (SEQ ID NO: 16), and YW278.15.3 (SEQ ID NO: 17). The CDRL1, CDRL2 and CDRL3 sequences are boxed.

FIG. 7 shows the alignment of the heavy chain sequences of IL-17A/F cross-reactive antibody YW278.15 (SEQ ID NO: 92) and its affinity matured variants, YW278.15.18 (SEQ ID NO: 93), YW278.15.2 (SEQ ID NO: 94), YW278.15.2.D54E (SEQ ID NO: 95), YW278.15.3 (SEQ ID NO: 92), YW278.15.18C55A (SEQ ID NO: 18) and YW278.15.18C55S (SEQ ID NO: 19). The CDRL1, CDRL2 and CDRL3 sequences are boxed. Note: YW278.15.18C55A and YW278.15.18C55S have the same light chain as YW278.15.18.

FIGS. 8A and 8B show the results of the BIAcore immunoassay performed with three affinity matured IL-17A/F cross-reactive antibodies. A. The binding affinities to recombinant human IL-17A (rhIL-17A), recombinant human IL-17F (rhIL-17F), cyno IL-17F and human IL-17A/F in solution (Kd (M)) are shown in the last column. B. The binding affinities to recombinant human IL-17A (rhIL-17A), recombinant human IL-17F (rhIL-17F), cyno IL-17F, cyno IL-17A (FIG. 8B), and human IL-17A/F in solution (Kd (M)) are shown in the last column.

FIG. 9 shows the results of the BIAcore immunoassay performed with two further affinity matured IL-17A/F cross-reactive antibodies, in comparison to YW278.15.18. The binding affinities to recombinant human IL-17A (rhIL-17A), recombinant human IL-17F (rhIL-17F), cyno IL-17F and human IL-17A/F in solution (Kd (M)) are shown in the last column.

FIG. 10 shows the results of the BIAcore immunoassay performed with three affinity matured IL-17A/F cross-reactive antibodies. The binding affinities to rhesus IL-17A are shown in the last column.

FIG. 11 shows the alignment of the light chain variable region sequences of IL-17A specific antibody YW264.21 (SEQ ID NO: 20) and IL-17F specific antibody YW265.01 (SEQ ID NO: 21).

FIG. 12 shows the alignment of the heavy chain variable region sequences of IL-17A specific antibody YW264.21 (SEQ ID NO: 22) and IL-17F specific antibody YW265.01 (SEQ ID NO: 23).

FIGS. 13A and 13B show the IC50 and IC90 data for several IL-17A/F cross-reactive antibodies, as well as the antibody molar ratios needed to inhibit the activity of the target IL-17A/F polypeptides.

FIG. 14 shows IL-17A and IL-17F binding affinity data for an IL-17A/F bispecific antibody in comparison with anti-IL-17A antibody YW264.1 and anti-IL-17F antibody YW265.01.

FIG. 15 shows another alignment of the light chain variable region sequences (SEQ ID NOS 61 and 20-21) of IL-17A/F bispecific antibodies, including antibody YW264.03 (SEQ ID NO: 61).

FIG. 16 shows another alignment of the heavy chain variable region sequences (SEQ ID NOS 62 and 22-23) of IL-17A/F bispecific antibodies, including YW264.03 (SEQ ID NO: 62).

DETAILED DESCRIPTION OF THE INVENTION

I. Definitions

Figure 17:
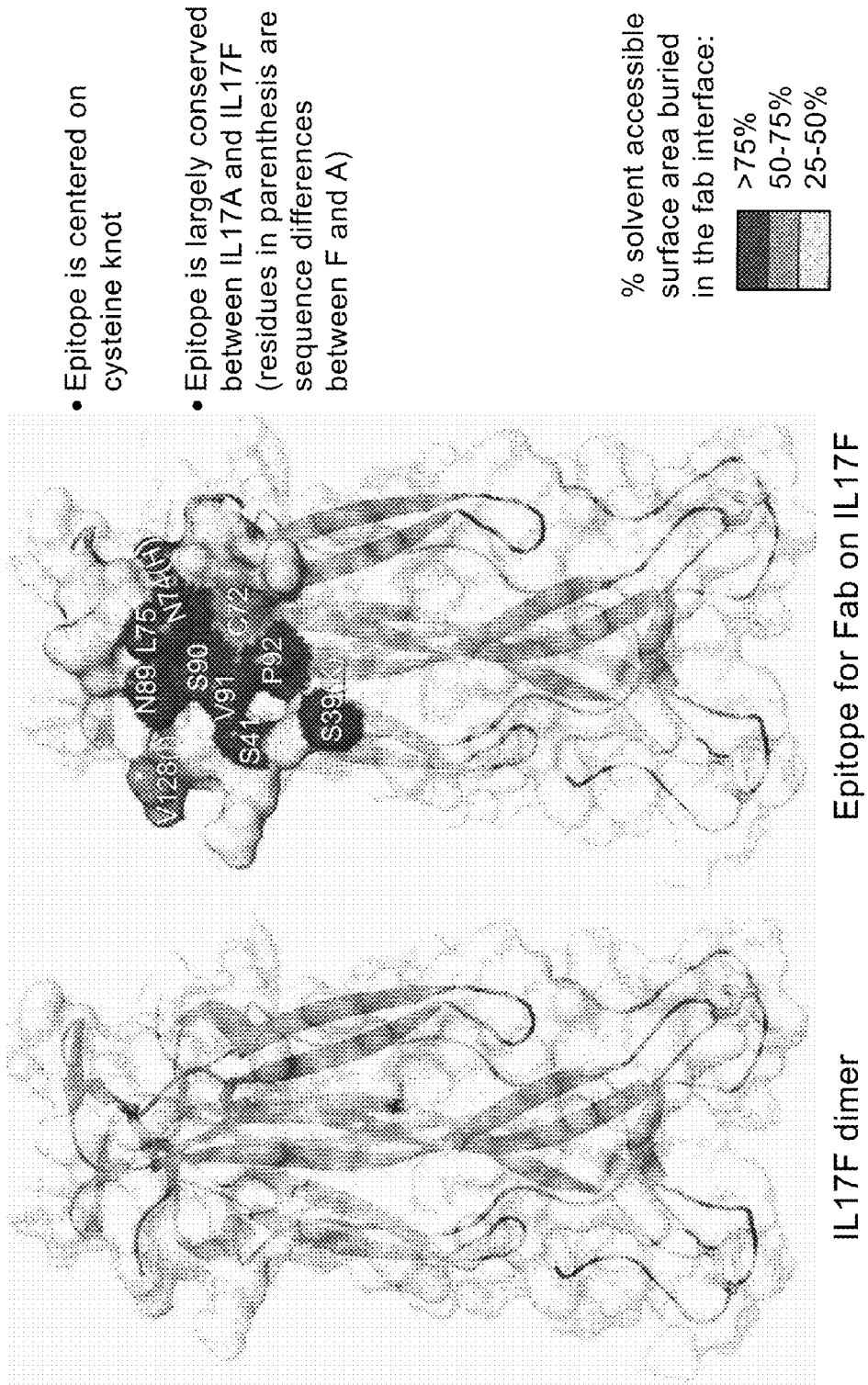
FIG. 17 shows the Fab bound to an IL-17F dimer.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

A "native sequence IL-17A/F polypeptide" comprises a polypeptide having the same amino acid sequence as the corresponding IL-17A/F polypeptide derived from nature. Such native sequence IL-17A/F polypeptides can be isolated from nature or can be produced by recombinant and/or synthetic means. The term "native sequence IL-17A/F polypeptide" specifically encompasses naturally-occurring truncated or secreted forms of the specific IL-17A/F polypeptide (e.g., an extracellular domain sequence), naturally-occurring variant forms (e.g., alternatively spliced forms) and naturally-occurring allelic variants of the polypeptide. In various embodiments of the invention, the native sequence IL-17A/F polypeptides disclosed herein are mature or full-length native sequence polypeptides comprising the full-length amino acid sequences shown in the accompanying figures. Start and stop codons are shown in bold font and underlined in the figures.

"IL-17A/F polypeptide variant" means an active IL-17A/F polypeptide as defined above or below having at least about 80% amino acid sequence identity with a full-length native sequence IL-17A/F polypeptide sequence as disclosed herein, an IL-17A/F polypeptide sequence lacking the signal peptide as disclosed herein, or any other fragment of a full-length IL-17A/F polypeptide sequence as disclosed herein. Such IL-17A/F polypeptide variants include, for instance, IL-17A/F polypeptides wherein one or more amino acid residues are added, or deleted, at the- or C-terminus of the full-length native amino acid sequence. Ordinarily, an IL-17A/F polypeptide variant will have at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to a full-length native sequence IL-17A/F polypeptide sequence as disclosed herein, an IL-17A/F polypeptide sequence lacking the signal peptide as disclosed herein, or any other specifically defined fragment of a full-length IL-17A/F polypeptide sequence as disclosed herein. Ordinarily, IL-17A/F variant polypeptides are at least about 10 amino acids in length, alternatively at least about 20 amino acids in length, alternatively at least about 30 amino acids in length, alternatively at least about 40 amino acids in length, alternatively at least about 50 amino acids in length, alternatively at least about 60 amino acids in length, alternatively at least about 70 amino acids in length, alternatively at least about 80 amino acids in length, alternatively at least about 90 amino acids in length, alternatively at least about 100 amino acids in length, alternatively at least about 150 amino acids in length, alternatively at least about 200 amino acids in length, alternatively at least about 300 amino acids in length, or more. The same definition applies to further variants of variant IL-17A/F polypeptides.

"Percent (%) amino acid sequence identity" with respect to the IL-17A/F polypeptide sequences identified herein is defined as the percentage of amino acid residues in a candidate sequence that are identical with the amino acid residues in the specific IL-17A/F polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc. and the source code has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

Unless specifically stated otherwise, all % amino acid sequence identity values used herein are obtained as described in the immediately preceding paragraph using the ALIGN-2 computer program. However, % amino acid sequence identity values may also be obtained as described below by using the WU-BLAST-2 computer program (Altschul et al., *Methods in Enzymology* 266:460-480 (1996)). Most of the WU-BLAST-2 search parameters are set to the default values. Those not set to default values e., the adjustable parameters, are set with the following values: overlap span=1, overlap fraction=0.125, word threshold (T)=11, and scoring matrix=BLOSUM62. When WU-BLAST-2 is employed, a % amino acid sequence identity value is determined by dividing (a) the number of matching identical amino acid residues between the amino acid sequence of the polypeptide of interest having a sequence derived from the native polypeptide and the comparison amino acid sequence of interest (i.e., the sequence against which the polypeptide of interest is being compared which may be an IL-17A/F variant polypeptide) as determined by WU-BLAST-2 by (b) the total number of amino acid residues of the polypeptide of interest. For example, in the statement "a polypeptide comprising an the amino acid sequence A which has or having at least 80% amino acid sequence identity to the amino acid sequence B", the amino acid sequence A is the comparison amino acid sequence of the "Comparison Protein" of interest and the amino acid sequence B is the amino acid sequence of the polypeptide of interest.

Percent amino acid sequence identity may also be determined using the sequence comparison program NCBI-BLAST2 (Altschul et al., *Nucleic Acids Res.* 25:3389-3402 (1997)). The NCBI-BLAST2 sequence comparison program may be downloaded from http://www.ncbi.nlm.nih.gov or otherwise obtained from the National Institute of Health, Bethesda, Md. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y where X is the number of amino acid residues scored as identical matches by the sequence alignment program NCBI-BLAST2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

"IL-17A/F variant polynucleotide" or "IL-17A/F variant nucleic acid sequence" means a nucleic acid molecule which encodes an active IL-17A/F polypeptide as defined below and which has at least about 80% nucleic acid sequence identity with a nucleotide acid sequence encoding a full-length native sequence IL-17A/F polypeptide sequence as disclosed herein, a full-length native sequence IL-17A/F polypeptide sequence lacking the signal peptide as disclosed herein, or any other fragment of a full-length IL-17A/F polypeptide sequence as disclosed herein. Ordinarily, an IL-17A/F variant polynucleotide will have at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity with a nucleic acid sequence encoding a full-length native sequence IL-17A/F polypeptide sequence as disclosed herein, a full-length native sequence IL-17A/F polypeptide sequence lacking the signal peptide as disclosed herein, or any other fragment of a full-length IL-17A/F polypeptide sequence as disclosed herein. Variants do not encompass the native nucleotide sequence.

Ordinarily, IL-17A/F variant polynucleotides are at least about 30 nucleotides in length, alternatively at least about 60 nucleotides in length, alternatively at least about 90 nucleotides in length, alternatively at least about 120 nucleotides in length, alternatively at least about 150 nucleotides in length, alternatively at least about 180 nucleotides in length, alternatively at least about 210 nucleotides in length, alternatively at least about 240 nucleotides in length, alternatively at least about 270 nucleotides in length, alternatively at least about 300 nucleotides in length, alternatively at least about 450 nucleotides in length, alternatively at least about 600 nucleotides in length, alternatively at least about 900 nucleotides in length, or more.

"Percent (%) nucleic acid sequence identity" with respect to IL-17A/F-encoding nucleic acid sequences identified herein is defined as the percentage of nucleotides in a candidate sequence that are identical with the nucleotides in the IL-17A/F nucleic acid sequence of interest, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. For purposes herein, however, % nucleic acid sequence identity values are generated using the sequence comparison computer program ALIGN-2, wherein the complete source code for the ALIGN-2 program has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code. The ALIGN-2 program should be compiled for use on a UNIX operating system, preferably digital UNIX V4.0D. All sequence comparison parameters are set by the ALIGN-2 program and do not vary.

In situations where ALIGN-2 is employed for nucleic acid sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows: 100 times the fraction W/Z where W is the number of nucleotides scored as identical matches by the sequence alignment program ALIGN-2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

Unless specifically stated otherwise, all % nucleic acid sequence identity values used herein are obtained as described in the immediately preceding paragraph using the ALIGN-2 computer program. However, % nucleic acid sequence identity values may also be obtained as described below by using the WU-BLAST-2 computer program (Altschul et al., *Methods in Enzymology* 266:460-480 (1996)). Most of the WU-BLAST-2 search parameters are set to the default values. Those not set to default values i.e., the adjustable parameters, are set with the following values: overlap span=1, overlap fraction=0.125, word threshold (T)=11, and scoring matrix=BLOSUM62. When WU-BLAST-2 is employed, a % nucleic acid sequence identity value is determined by dividing (a) the number of matching identical nucleotides between the nucleic acid sequence of the IL-17A/F polypeptide-encoding nucleic acid molecule of interest having a sequence derived from the native sequence IL-17A/F polypeptide-encoding nucleic acid and the comparison nucleic acid molecule of interest (i.e., the sequence against which the IL-17A/F polypeptide-encoding nucleic acid molecule of interest is being compared which may be a variant IL-17A/F polynucleotide) as determined by WU-BLAST-2 by (b) the total number of nucleotides of the IL-17A/F polypeptide-encoding nucleic acid molecule of interest. For example, in the statement "an isolated nucleic acid molecule comprising a nucleic acid sequence A which has or having at least 80% nucleic acid sequence identity to the nucleic acid sequence B", the nucleic acid sequence A is the comparison nucleic acid molecule of interest and the nucleic acid sequence B is the nucleic acid sequence of the IL-17A/F polypeptide-encoding nucleic acid molecule of interest.

Percent nucleic acid sequence identity may also be determined using the sequence comparison program NCBI-BLAST2 (Altschul et al., *Nucleic Acids Res.* 25:3389-3402 (1997)). The NCBI-BLAST2 sequence comparison program may be downloaded from http://www.ncbi.nim.nih.gov or otherwise obtained from the National Institute of Health, Bethesda, Md. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows: 100 times the fraction W/Z where W is the number of nucleotides scored as identical matches by the sequence alignment program NCBI-BLAST2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

In other embodiments, IL-17A/F variant polynucleotides are nucleic acid molecules that encode an active IL-17A/F polypeptide and which are capable of hybridizing, preferably under stringent hybridization and wash conditions, to nucleotide sequences encoding a full-length IL-17A/F polypeptide as disclosed herein. IL-17A/F variant polypeptides may be those that are encoded by an IL-17A/F variant polynucleotide.

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the IL-17A/F polypeptide natural environment will not be present. Ordinarily, however, isolated polypeptide will be prepared by at least one purification step.

An "isolated" IL-17A/F polypeptide-encoding nucleic acid or other polypeptide-encoding nucleic acid is a nucleic acid molecule that is identified and separated from at least one contaminant nucleic acid molecule with which it is ordinarily associated in the natural source of the polypeptide-encoding nucleic acid. An isolated polypeptide-encoding nucleic acid molecule is other than in the form or setting in which it is found in nature. Isolated polypeptide-encoding nucleic acid molecules therefore are distinguished from the specific polypeptide-encoding nucleic acid molecule as it exists in natural cells. However, an isolated polypeptide-encoding nucleic acid molecule includes polypeptide-encoding nucleic acid molecules contained in cells that ordinarily express the polypeptide where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include an promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; an promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5.times.SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1.times.SSC containing EDTA at 55° C.

"Moderately stringent conditions" may be identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "epitope tagged" when used herein refers to a chimeric polypeptide comprising an IL-17A/F polypeptide fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

The term "antagonist" is used in the broadest sense, and includes any molecule that partially or fully blocks, inhibits, or neutralizes a biological activity of a native IL-17A/F polypeptide disclosed herein. In a similar manner, the term "agonist" is used in the broadest sense and includes any molecule that mimics a biological activity of a native IL-17A/F polypeptide disclosed herein. Suitable agonist or antagonist molecules specifically include agonist or antagonist antibodies or antibody fragments, fragments or amino acid sequence variants of native IL-17A/F polypeptides, peptides, antisense oligonucleotides, small organic molecules, etc. Methods for identifying agonists or antagonists of an IL-17A/F polypeptide may comprise contacting an IL-17A/F polypeptide with a candidate agonist or antagonist molecule and measuring a detectable change in one or more biological activities normally associated with the IL-17A/F polypeptide.

"Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

"Mammal" for purposes of treatment refers to any animal classified as a mammal, including humans, non-human higher primates, domestic and farm animals, and zoo, sports, or pet animals, such as dogs, cats, cattle, horses, sheep, pigs, goats, rabbits, etc. Preferably, the mammal is human.

Administration "in combination with" one or more further therapeutic agents includes simultaneous (concurrent) and consecutive administration in any order.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

The term "antibody" is used in the broadest sense and specifically covers, for example, single anti-IL-17A/F or anti-IL17A or anti-IL-17F monoclonal antibodies (including agonist, antagonist, and neutralizing antibodies), corresponding antibody compositions with polyepitopic specificity, polyclonal antibodies, single chain antibodies, and antibody fragments (see below) as long as they exhibit the desired biological or immunological activity. The term "immunoglobulin" (Ig) is used interchangeably with antibody herein.

An "isolated antibody" is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The basic 4-chain antibody unit is a heterotetrameric glycoprotein composed of two identical light (L) chains and two identical heavy (H) chains (an IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to a H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain ($C_L$) at its other end. The $V_L$ is aligned with the $V_H$ and the $C_L$ is aligned with the first constant domain of the heavy chain ($C_{H1}$). Particular amino acid residues are believed to form an interface between the light chain and heavy chain variable domains. The pairing of a $V_H$ and $V_L$ together forms a single antigen-binding site. For the structure and properties of the different classes of antibodies, see, e.g., *Basic and Clinical Immunology*, 8th edition, Daniel P. Stites, Abba I. Terr and Tristram G. Parslow (eds.), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains (C.sub.H), immunoglobulins can be assigned to different classes or isotypes. There are five classes of immunoglobulins: IgA, IgD, IgE, IgG, and IgM, having heavy chains designated .α, δ, ε, γ, and μ, respectively. The γ and α classes are further divided into subclasses on the basis of relatively minor differences in $C_H$ sequence and function, e.g., humans express the following subclasses: IgG1, IgG2, IgG3, IgG4, IgA1, and IgA2.

The term "variable" refers to the fact that certain segments of the variable domains differ extensively in sequence among antibodies. The V domain mediates antigen binding and define specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a .beta.-sheet configuration, connected by three hypervariable regions, which form loops connecting, and in some cases forming part of, the .beta.-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. around about residues 24-34 (L1), 50-56 (L2) and 89-97 (L3) in the $V_L$, and around about 1-35 (H1), 50-65 (H2) and 95-102 (H3) in the $V_H$; Kabat et al., Sequences of Proteins of Immunological Interest, 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the $V_L$, and 26-32 (H1), 53-55 (H2) and 96-101 (H3) in the $V_H$; Chothia and Lesk J. Mol. Biol. 196: 901-917 (1987)).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222:581-597 (1991), for example.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81:6851-6855 (1984)). Chimeric antibodies of interest herein include "primatized" antibodies comprising variable domain antigen-binding sequences derived from a non-human primate (e.g. Old World Monkey, Ape etc), and human constant region sequences.

An "intact" antibody is one which comprises an antigen-binding site as well as a C.sub.L and at least heavy chain constant domains, CH1, CH2 and CH3. The constant domains may be native sequence constant domains (e.g. human native sequence constant domains) or amino acid sequence variant thereof. Preferably, the intact antibody has one or more effector functions.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (see U.S. Pat. No. 5,641,870, Example 2; Zapata et al., Protein Eng. 8(10): 1057-1062 [1995]); single-chain antibody molecules; and multispecific antibodies formed from antibody fragments. In a preferred embodiment, the fragment is "functional," i.e. qualitatively retains the ability of the corresponding intact antibody to bind to the target IL-17A and IL-17F polypeptides and, if the intact antibody also inhibits IL-17A/F biological activity or function, qualitatively retains such inhibitory property as well. Qualitative retention means that the activity in kind is maintained, but the degree of binding affinity and/or activity might differ.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_{H1}$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having divalent antigen-binding activity and is still capable of cross-linking antigen. Fab' fragments differ from Fab fragments by having additional few residues at the carboxy terminus of the C$_{H1}$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the V.sub.H and V.sub.L antibody domains connected into a single polypeptide chain. Preferably, the sFv polypeptide further comprises a polypeptide linker between the V.sub.H and V.sub.L domains which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments (see preceding paragraph) with short linkers (about 5-10 residues) between the V$_H$ and V$_L$ domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the V$_H$ and V$_L$ domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993).

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332: 323-329 (1988); and Presta, Curr. Op. Struct. Biol. 2:593-596 (1992).

A "cross-reactive antibody" is an antibody which recognizes identical or similar epitopes on more than one antigen. Thus, the cross-reactive antibodies of the present invention recognize identical or similar epitopes present on both IL-17A and IL-17F. In a particular embodiment, the cross-reactive antibody uses the same or essentially the same paratope to bind to both IL-17A and IL-17F. Preferably, the cross-reactive antibodies herein also block both IL-17A and IL-17F function (activity).

The term "paratope" is used herein to refer to the part of an antibody that binds to a target antigen.

A "species-dependent antibody," e.g., a mammalian anti-IL-17A/F" antibody, is an antibody which has a stronger binding affinity for an antigen from a first mammalian species than it has for a homologue of that antigen from a second mammalian species. Normally, the species-dependent antibody "bind specifically" to a human antigen (i.e., has a binding affinity (Kd) value of no more than about $1 \times 10^{-7}$ M, preferably no more than about $1 \times 10^{-8}$ M and most preferably no more than about $1 \times 10^{-9}$ M) but has a binding affinity for a homologue of the antigen from a second non-human mammalian species which is at least about 50 fold, or at least about 500 fold, or at least about 1000 fold, weaker than its binding affinity for the human antigen. The species-dependent antibody can be of any of the various types of antibodies as defined above, but preferably is a humanized or human antibody.

An antibody "which binds" an antigen of interest, is one that binds the antigen with sufficient affinity such that the antibody is useful as a diagnostic and/or therapeutic agent in targeting a cell or tissue expressing the antigen, and does not significantly cross-react with other proteins. In such embodiments, the extent of binding of the antibody to a "non-target" protein will be less than about 10% of the binding of the antibody to its particular target protein as determined by fluorescence activated cell sorting (FACS) analysis or radio immunoprecipitation (RIA). With regard to the binding of an antibody to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of at least about $10^{-4}$ M, alternatively at least about $10^{-5}$ M, alternatively at least about $10^{-6}$ M, alternatively at least about $10^{-7}$ M, alternatively at least about $10^{-8}$ M, alternatively at least about $10^{-9}$ M, alternatively at least about $10^{-10}$ M, alternatively at least about $10^{-11}$ M, alternatively at least about $10^{-12}$ M, or greater. In one embodiment, the term "specific binding" refers to binding where a molecule binds to a particular polypeptide or epitope on a particular polypeptide without substantially binding to any other polypeptide or polypeptide epitope. In preferred embodiments, the specific binding affinity is at least about $10^{-10}$ M.

Antibody "effector functions" refer to those biological activities attributable to the Fc region (a native sequence Fc region or amino acid sequence variant Fc region) of an antibody, and vary with the antibody isotype. Examples of antibody effect or functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express Fc .gamma.RIII only, whereas monocytes express Fc.gamma.RI, Fc.gamma.RII and Fc.gamma.RIII. FcR expression on hematopoietic cells is summarized in Table 3 on page 464 of Ravetch and Kinet, Annu. Rev. Immunol. 9:457-92 (1991). To assess ADCC activity of a molecule of interest, an in vitro ADCC assay, such as that described in U.S. Pat. Nos. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. Proc. Natl. Acad. Sci. U.S.A. 95:652-656 (1998).

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII and FcγRIII subclasses, including allelic variants and alternatively spliced forms of these receptors. Fc.gamma.RII receptors include FcγRIIA (an "activating receptor") and FcγRIIB (an "inhibiting receptor"), which have similar amino acid sequences that differ primarily in the cytoplasmic domains thereof. Activating receptor Fc.gamma.RIIA contains an immunoreceptor tyrosine-based activation motif (ITAM) in its cytoplasmic domain. Inhibiting receptor Fc.gamma.RIIB contains an immunoreceptor tyrosine-based inhibition motif (ITIM) in its cytoplasmic domain. (see review M. in Daeron, Annu. Rev. Immunol. 15:203-234 (1997)). FcRs are reviewed in Ravetch and Kinet, Annu. Rev. Immunol. 9:457-492 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976) and Kim et al., J. Immunol. 24:249 (1994)).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source, e.g., from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al., Immunol. Methods 202:163 (1996), may be performed.

The word "label" when used herein refers to a detectable compound or composition which is conjugated directly or indirectly to the antibody so as to generate a "labeled" antibody. The label may be detectable by itself (e.g. radioisotope labels or fluorescent labels) or, in the case of an enzymatic label, may catalyze chemical alteration of a substrate compound or composition which is detectable.

By "solid phase" is meant a non-aqueous matrix to which the antibody of the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as an IL-17A/F polypeptide or antibody thereto) to a mammal. The components of the liposome are commonly arranged in a bilayer formation, similar to the lipid arrangement of biological membranes.

"Active" or "activity" or "function" with reference to an IL-17A/F polypeptide for the purposes herein refers to form(s) of the IL-17A/F polypeptide which retain a biological and/or an immunological activity of native or naturally-occurring IL-17A/F polypeptides, wherein "biological" activity refers to a biological function (either inhibitory or stimulatory) caused by a native or naturally-occurring IL-17A/F polypeptide other than the ability to induce the production of an antibody against an antigenic epitope possessed by a native or naturally-occurring IL-17A/F polypeptide and an "immunological" activity refers to the ability to induce the production of an antibody against an antigenic epitope possessed by a native or naturally-occurring IL-17A/F polypeptide. One preferred biological activity includes inducing activation of NF-κB and stimulation of the production of the proinflammatory chemokines IL-8 and IL-6. Another preferred biological activity includes stimulation of peripheral blood mononuclear cells or CD4+ cells. Another preferred biological activity includes stimulation of the proliferation of T-lymphocytes. Another preferred biological activity includes, for example, the release of TNF-α from THP1 cells. Another activity includes an enhancement of matrix synthesis in articular cartilage. Alternatively, another activity includes promoting breakdown of articular cartilage matrix as well as inhibiting matrix synthesis. Another preferred biological activity includes modulating the level of the interleukin-17 signalling pathway during mild to severe stages of inflammatory bowel disease or during stroke.

With reference to anti-IL-17A/F (or anti-IL-17A or anti-IL-17F) antibodies the terms "active" or "activity" or "function", and grammatical variants thereof, are used to refer to the ability to inhibit (blocking or antagonist antibodies) or mimic (agonist antibodies) at least one of the foregoing activities. Antibodies and antibody fragments referred to as "functional" are characterized by having such properties.

An "immunological" activity refers only to the ability to induce the production of an antibody against an antigenic epitope possessed by a native or naturally-occurring IL-17A/F polypeptide.

Degenerative cartilaginous disorder" describes a host of disorders that is characterized principally by the destruction of the cartilage matrix. Additional pathologies includes nitric oxide production, and elevated proteoglycan breakdown. Exemplary disorders encompassed within this definition, include, for example, arthritis (e.g., osteoarthritis, rheumatoid arthritis, psoriatic arthritis).

The term "immune related disease" means a disease in which a component of the immune system of a mammal causes, mediates or otherwise contributes to a morbidity in the mammal. Also included are diseases in which stimulation or intervention of the immune response has an ameliorative effect on progression of the disease. Included within this term are immune-mediated inflammatory diseases, non-immune-mediated inflammatory diseases, infectious diseases, immunodeficiency diseases, neoplasia, etc.

The term "T cell mediated disease" means a disease in which T cells directly or indirectly mediate or otherwise contribute to morbidity in a mammal. The T cell mediated disease may be associated with cell mediated effects, lymphokine mediated effects, etc., and even effects associated with B cells if the B cells are stimulated, for example, by the lymphokines secreted by T cells.

Examples of immune-related and inflammatory diseases, some of which are immune or T cell mediated, which can be treated according to the invention include systemic lupus erythematosis, rheumatoid arthritis, juvenile chronic arthritis, spondyloarthropathies, systemic sclerosis (scieroderma), idiopathic inflammatory myopathies (dermatomyositis, polymyositis), Sjogren's syndrome, systemic vasculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic demyelinating polyneuropathy or Guillain-Barre syndrome, and chronic inflammatory demyelinating polyneuropathy, hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis, inflammatory bowel disease (IBD), including ulcerative colitis: Crohn's disease, gluten-sensitive enteropathy, and Whipple's disease, autoimmune or immune-mediated skin diseases including bullous skin diseases, erythema multiforme and contact dermatitis, psoriasis, allergic diseases such as asthma, allergic rhinitis, atopic dermatitis, food hypersensitivity and urticaria, immunologic diseases of the lung such as eosinophilic pneumonia, idiopathic pulmonary fibrosis and hypersensitivity pneumonitis, transplantation associated diseases including graft rejection and graft-versus-host-disease. Infectious diseases including viral diseases such as AIDS (HIV infection), hepatitis A, B, C, D, and E, herpes, etc., bacterial infections, fungal infections, protozoal infections and parasitic infections.

The term "effective amount" is a concentration or amount of an IL-17A/F polypeptide and/or agonist/antagonist which results in achieving a particular stated purpose. An "effective amount" of an IL-17A/F polypeptide or agonist or antagonist thereof may be determined empirically. Furthermore, a "therapeutically effective amount" is a concentration or amount of an IL-17A/F polypeptide and/or agonist/antagonist which is effective for achieving a stated therapeutic effect. This amount may also be determined empirically.

II. Detailed Description

The present invention provides a method for preparing antibodies cross-reactive with IL-17A/F and bispecific antibodies specifically binding to IL-17A and IL-17F. IL-17A and IL-17F are major pro-inflammatory cytokines secreted by Th17 T cell subset. They target almost all the cell types in body and induce tissue inflammation and tissue damage. Due to the involvement of these cytokines in inflammation and, in particular, immune related diseases, such as autoimmune diseases, e.g. rheumatoid arthritis (RA) and inflammatory bowel disease (IBD), makes it desirable to produce antibodies that are capable of blocking both IL-17A and IL-17F. The present invention provides such antibodies. More specifically, the present invention provides antibodies cross-reactive with IL-17A and IL-17F as well as bispecific antibodies with binding specificities both for IL-17A and IL-17F.

General Methods for the Recombinant Production of Antibodies

The antibodies and other recombinant proteins herein can be produced by well known techniques of recombinant DNA technology. Thus, aside from the antibodies specifically identified herein, the skilled practitioner could generate antibodies directed against an antigen of interest, e.g., using the techniques described below.

The antibodies produced in accordance with the present invention are directed against two antigens of interest, IL-17A and IL-17F. The IL-17A/F cross-reactive and bispecific antibodies of the present invention have been generated using phage display technology, but other techniques known for making bispecific antibodies and antibodies having an antigen binding region binding to two different antigens can also be used.

Cross-Reactive Antibodies

According to one embodiment, an antibody with specificity for one of IL-17A is diversified such that it develops specificity for IL-17F the while retaining specificity for IL-17A. Alternatively, an antibody with binding specificity for IL-17F is diversified such that it develops specificity for IL-17A while retaining specificity for IL-17F. In generic terms, this method comprises the steps of (1) diversifying the amino acid sequence of a light chain variable domain ($V_L$) of an antibody, wherein prior to the diversification, the antibody comprised a $V_L$ and a heavy chain variable domain ($V_H$) capable of binding to an epitope on a first IL-17 protein (IL-17A or IL-17F) and (2) selecting a diversified antibody capable of binding to the epitope on the first IL-17 protein (IL-17A or IL-17F) and an epitope on a second IL-17 protein (IL-17F or IL-17A). A detailed description of this method is provided in co-pending Application Publication No. 20080069820 published Mar. 20, 2008, the entire disclosure of which is expressly incorporated by reference herein. A specific production and selection method for producing the IL-17A/F cross-reactive antibodies is illustrated in Example 1.

Bispecific Antibodies

According to another embodiment, an antibody that has specificity for two IL-17 polypeptides (IL-17A and IL-17F) is isolated from a non-human mammal, such as a mouse or a rat, that was injected with IL-17A and IL-17F.

Methods for making bispecific antibodies are known in the art. Traditional production of full length bispecific antibodies is based on the coexpression of two immunoglobulin heavy chain-light chain pairs, where the two chains have different specificities (Millstein et al., *Nature*, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.*, 10:3655-3659 (1991).

According to another approach described in WO 96/27011, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676, 980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

For review of methods for making bispecific antibodies, see, e.g. Holliger, P. and Winter, G., *Curr. Opin. Biotechnol.* 4, 446-449 (1993); Carter, P. et al., *J. Hematotherapy* 4, 463-470 (1995); and Pluckthun, A. and Pack, P., *Immunotechnology* 3, 83-105 (1997). Bispecificity and/or bivalency has been accomplished by fusing two scFv molecules via flexible linkers, leucine zipper motifs, heterodimerization, and by association of scFv molecules to form bivalent monospecific diabodies and related structures.

Thus, for example, in order to generate bispecific antibodies, one can start with two mono-specific antibodies (e.g. anti-IL-17A and anti-IL-17F antibodies). The two arms of the antibodies can then be separated and rejoined covalently to form a bispecific antibody. Such a bispecific antibody can comprise a common Fc portion and one Fab portion from each of the parental molecules. Thus, one Fab portion is specific for one of the receptor subunits, and the other is specific for a different receptor subunit. Of course, the starting materials need not be intact, bivalent antibodies. For example, they can be fragments, e.g., Fab fragments, or Fab fragments further comprising one or more heavy chain CH2 and/or CH3 domains (e.g., F(ab=)2 fragments).

Bispecific antibodies can also be prepared using chemical linkage. Brennan et al., *Science* 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. In a further embodiment, Fab'-SH fragments directly recovered from *E. coli* can be chemically coupled vitro to form bispecific antibodies. Shalaby et al., J. Exp. Med. 175:217-225 (1992).

Bispecific antibodies include cross-linked or "heteroconjugate" antibodies. For example, one of the antibodies in the heteroconjugate can be coupled to avidin, the other to biotin. Heteroconjugate antibodies may be made using any convenient cross-linking methods. Suitable cross-linking agents are well known in the art, and are disclosed in U.S. Pat. No. 4,676,980, along with a number of cross-linking techniques.

Bispecific antibodies have also been produced using leucine zippers. Kostelny et al., *J. Immunol.* 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., J. Immunol. 152:5368 (1994). Alternatively, the bispecific antibody may be a "linear antibody" produced as described in Zapata et al. Protein Eng. 8(10):1057-1062 (1995).

Any of a variety of conventional methods can be used to chemically couple (cross-link) two polypeptide chains (e.g., antibody moieties). Covalent binding can be achieved either by direct condensation of existing side chains (e.g., the formation of disulfide bonds between cysteine residues) or by the incorporation of external bridging molecules. Many bivalent or polyvalent agents are useful in coupling polypeptides. For a description of some methods which can be used to chemically cross-link antibodies, see, e.g., Cao et al. (1988) Bioconjugate Chemistry 9, 635-644; Shalaby et al. (1992) J. Exp. Med. 175, 217-225; Glennie et al. (1987) J. Immunol. 139, 2367-2375; Jung et al. (1991) Eur. J. Immunol. 21, 2431-2435; VanDijk et al. (1989) Int. J. Cancer 44, 738-743; Pierce ImmunoTechnology Catalog & Handbook (1991) E8-E39; Karpovsky et al. (1984) J. Exp. Med. 160, 1686; Liu et al. (1985) Proc. Natl. Acad. Sci. USA 82, 8648; Kranz et al. (1981), PNAS 78, 5807; Perez et al. (1986), J. Exp. Med. 163, 166-178; Brennan (1986) Biotech. 4, 424; and U.S. Pat. Nos. 4,676,980, 6,010,902 and 5,959,083.

In addition, recombinant techniques can be used to generate a single-chain bispecific antibody, as described, for example, in Whitlow et al. (1991), Methods: A Companion to Methods in Enzymology, Vol. 2, page 97; Bird et al. (1988), *Science* 242, 423-426; U.S. Pat. No. 4,946,778; Pack et al. (1993), *Bio/Technology* 11, 1271-77; and Sandhu (1992), *Crit. Rev. Biotech.* 12, 437. Methods for generating bispecific single chain antibodies, in particular, are described, e.g., in U.S. Pat. No. 5,892,020; Gruber et al. (1994). *J. Immunol.* 152, 5368-74; Mallender et al. (1994). *Biochemistry* 33, 10100-10108; Winter et al. (1991). *Nature* 349, 293-299; Schmidt et al. (1996). *International Journal of Cancer* 65, 538-546; and Thirion et al. (1996). *Eur. J. of Cancer Prevention* 5, 507-511.

A specific method for making bispecific antibodies is described in Example 2 herein.

Recombinant Production of Antibodies

For recombinant production of the antibody, the nucleic acid encoding it may be isolated and inserted into a replicable vector for further cloning (amplification of the DNA) or for expression. In another embodiment, the antibody may be produced by homologous recombination, e.g. as described in U.S. Pat. No. 5,204,244, specifically incorporated herein by reference. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence, e.g., as described in U.S. Pat. No. 5,534,615 issued Jul. 9, 1996 and specifically incorporated herein by reference.

Suitable host cells for cloning or expressing the DNA encoding antibody chains include mammalian host cells. Interest has been great in mammalian host cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/−DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2).

Host cells are transformed with expression or cloning vectors for antibody production and cultured in conventional nutrient media modified as appropriate for inducing promoters, selecting transformants, or amplifying the genes encoding the desired sequences.

The mammalian host cells may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102: 255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, human γ2, or human γ4 heavy chains (Lindmark et al., J. Immunol. Meth. 62:1-13 (1983)). Protein G is recommended for all mouse isotypes and for human γ3 (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, hydrophobic interaction chromatography, and ammonium sulfate precipitation are also available depending on the antibody to be recovered.

Following any preliminary purification step(s), the mixture comprising the antibody of interest and contaminants may be subjected to additional purification steps to achieve the desired level of purity.

A humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature,* 321:522-525 (1986); Riechmann et al., *Nature,* 332:323-327 (1988); Verhoeyen et al., *Science,* 239: 1534-1536 (1988)), by substituting rodent CDRs or CDR sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human FR for the humanized antibody (Sims et al., *J. Immunol.*, 151:2296 (1993)). Another method uses a particular framework derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immunol.*, 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA*, 90:2551 (1993); Jakobovits et al., *Nature*, 362:255-258 (1993); Bruggermann et al., *Year in Immuno.*, 7:33 (1993); and Duchosal et al. *Nature* 355:258 (1992). Human antibodies can also be derived from phage-display libraries (Hoogenboom et al., *J. Mol. Biol.*, 227:381 (1991); Marks et al., *J. Mol. Biol.*, 222:581-597 (1991); Vaughan et al. *Nature Biotech* 14:309 (1996)).

Therapeutic Uses

The antibodies of the present invention are useful in the treatment of inflammatory and immune related diseases associated with the production of IL-17A and/or IL-17F. As discussed earlier, in view of the proinflammatory properties of both IL-17A and IL-17F, the cross-reactive and bispecific antibodies that can block both IL-17A and IL-17F with high potency provide new therapeutic opportunities in the treatment of inflammatory and immune-related diseases, including autoimmune diseases.

Exemplary inflammatory and immune-related diseases targeted by the cross-reactive and bispecific antibodies of the present invention, which may be, but don't have to be, immune or T cell mediated, include systemic lupus erythematosis, rheumatoid arthritis, juvenile chronic arthritis, spondyloarthropathies, systemic sclerosis (scieroderma), idiopathic inflammatory myopathies (dermatomyositis, polymyositis), Sjogren's syndrome, systemic vasculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic demyelinating polyneuropathy or Guillain-Barre syndrome, and chronic inflammatory demyelinating polyneuropathy, hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis, inflammatory bowel disease (IBD), including ulcerative colitis: Crohn's disease, gluten-sensitive enteropathy, and Whipple's disease, autoimmune or immune-mediated skin diseases including bullous skin diseases, erythema multiforme and contact dermatitis, psoriasis, allergic diseases such as asthma, allergic rhinitis, atopic dermatitis, food hypersensitivity and urticaria, immunologic diseases of the lung such as eosinophilic pneumonia, idiopathic pulmonary fibrosis and hypersensitivity pneumonitis, transplantation associated diseases including graft rejection and graft-versus-host-disease. Infectious diseases including viral diseases such as AIDS (HIV infection), hepatitis A, B, C, D, and E, herpes, etc., bacterial infections, fungal infections, protozoal infections and parasitic infections.

In a specific embodiment the antibodies are used to treat rheumatoid arthritis (RA), inflammatory bowel disease (IBD), including ulcerative colitis and Crohn's disease, asthma or other allergic or autoimmune diseases.

Dosages and Formulations

The antibody or antibody fragment compositions herein will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the antibody or antibody fragment to be administered will be governed by such considerations, and is the minimum amount necessary to prevent, ameliorate, or treat a target disease, such as any of the diseases and conditions listed above. The antibody or antibody fragment need not be, but is optionally formulated with one or more agents currently used to prevent or treat the target disease. The effective amount of such other agents depends on the amount of antibody or antibody fragment present in the formulation, the type of disorder or treatment, and other factors discussed above. These are generally used in the same dosages and with administration routes as used hereinbefore or about from 1 to 99% of the heretofore employed dosages.

Generally, treatment of a target disease involves the lessening of one or more symptoms or medical problems associated with the target disease. For example, if the target disease is an inflammatory disease or condition, the treatment can reduce inflammation and/or alleviate one or more symptoms associated with inflammation.

In the case of rheumatoid arthritis, symptoms include, without limitation, muscle and joint aches, stiffness, swelling, joint pain or tenderness, one or more of which can be alleviated by administration of the antibodies herein, In addition, the cross-reactive and bispecific anti-IL17A/F antibodies of the present invention can prevent, reduce, or slow down the physical manifestations of the target disease. For example, if the target disease is rheumatoid arthritis, the treatment may prevent, lessen, reduce, or slow down the development of structural damage, such as bone erosions and joint damage characteristic of the disease. For this indication, the cross-reactive and bispecific antibodies of the present invention can be combined with other treatment modalities used in clinical practice, such as administration of Rituxan® (rituximab), alone or in combination with methotrexate, to treat patients with moderately-to-severely active rheumatoid arthritis (RA). Other treatment options that can be used in combination with the antibodies of the present invention include, without limitation, non-steroidal anti-inflammatory drugs (NSAIDs), corticosteroids, and TNF antagonist therapies, such as etanercept, infliximab, or adalimumab.

If the target disease is inflammatory bowel disease (IBD), including ulcerative colitis and Crohn's disease, the treatment may prevent, lessen, reduce, or slow down the development of inflammation, and/or one or more of the accompanying symptoms, including abdominal pain, diarrhea or constipation, fatigue, and fever. Treatment with the cross-reactive and bispecific antibodies of the present invention can be combined with traditional treatments for the management of IBD, including aminosalicylates, corticosteroids, antibiotics, and other biologic treatment options, such as TNF antagonist therapies, such as etanercept, infliximab, or adalimumab.

Therapeutic formulations are prepared using standard methods known in the art by mixing the active ingredient having the desired degree of purity with optional physiologically acceptable carriers, excipients or stabilizers (Remington's Pharmaceutical Sciences (20.sup.th edition), ed. A. Gennaro, 2000, Lippincott, Williams & Wilkins, Philadelphia, Pa.). Acceptable carriers, include saline, or buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagines, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™, or PEG.

Optionally, but preferably, the formulation contains a pharmaceutically acceptable salt, preferably sodium chloride, and preferably at about physiological concentrations. Optionally, the formulations of the invention can contain a pharmaceutically acceptable preservative. In some embodiments the preservative concentration ranges from 0.1 to 2.0%, typically v/v. Suitable preservatives include those known in the pharmaceutical arts. Benzyl alcohol, phenol, m-cresol, methylparaben, and propylparaben are preferred preservatives. Optionally, the formulations of the invention can include a pharmaceutically acceptable surfactant at a concentration of 0.005 to 0.02%.

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, supra.

Sustained-release preparations may be prepared. Suitable examples of sustained-release preparations include semipermeable matrices of solid hydrophobic polymers containing the antibody, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and .gamma. ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The antibodies and antibody fragments described herein are administered to a human subject, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Local administration may be particularly desired if extensive side effects or toxicity is associated with the antibodies herein antagonism. An ex vivo strategy can also be used for therapeutic applications. Ex vivo strategies involve transfecting or transducing cells obtained from the subject with a polynucleotide encoding an antibody or antibody fragment. The transfected or transduced cells are then returned to the subject. The cells can be any of a wide range of types including, without limitation, hemopoietic cells (e.g., bone marrow cells, macrophages, monocytes, dendritic cells, T cells, or B cells), fibroblasts, epithelial cells, endothelial cells, keratinocytes, or muscle cells.

Articles of Manufacture and Kits

Another embodiment of the invention is an article of manufacture containing materials useful for the treatment of diseases or conditions targeted by the antibodies of the present invention. The article of manufacture comprises a container and a label or package insert on or associated with the container. Suitable containers include, for example, bottles, vials, syringes, etc. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). At least one active agent in the composition is a cross-reactive or bispecific antibody or antibody fragment antibody of the invention. The label or package insert indicates that the composition is used for treating the particular condition. The label or package insert will further comprise instructions for administering the antibody composition to the patient. Articles of manufacture and kits comprising combinatorial therapies described herein are also contemplated.

Package insert refers to instructions customarily included in commercial packages of therapeutic products that contain information about the indications, usage, dosage, administration, contraindications and/or warnings concerning the use of such therapeutic products. In one embodiment, the package insert indicates that the composition is used for treating of an inflammatory or immune related condition, such as, for example, any of the conditions listed before, including various forms of arthritis, e.g. rheumatoid arthritis, inflammatory bowel disease (IBD), other autoimmune diseases, or allergic conditions, such as asthma.

Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The foregoing written description is considered to be sufficient to enable one skilled in the art to practice the invention. The following Examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

Commercially available reagents referred to in the Examples were used according to manufacturer's instructions unless otherwise indicated. The source of those cells identified in the following Examples, and throughout the specification, by ATCC accession numbers is the American Type Culture Collection, Manassas, Va. Unless otherwise noted, the present invention uses standard procedures of recombinant DNA technology, such as those described hereinabove and in the following textbooks: Sambrook et al., supra; Ausubel et al., *Current Protocols in Molecular Biology* (Green Publishing Associates and Wiley Interscience, N.Y., 1989); Innis et al., *PCR Protocols: A Guide to Methods and Applications* (Academic Press, Inc.: N.Y., 1990); Harlow et al., *Antibodies: A Laboratory Manual* (Cold Spring Harbor Press: Cold Spring Harbor, 1988); Gait, *Oligonucleotide Synthesis* (IRL Press: Oxford, 1984); Freshney, *Animal Cell Culture*, 1987; Coligan et al., *Current Protocols in Immunology*, 1991.

EXAMPLES

The following examples are offered for illustrative purposes only, and are not intended to limit the scope of the present invention in any way.

All patent and literature references cited in the present specification are hereby incorporated by reference in their entirety.

Example 1

Anti-IL-17A/F Cross-Reactive Antibodies

Materials and Methods

Library Sorting and Screening to Identify Anti-IL-17A/F Antibodies

Human IL-17 A (R&D Systems, cat #317-IL-050/CF) and IL-17 F (R&D Systems, cat #1335-IL-025/CF) were used as antigens for library sorting. For conventional sorting, the phage libraries were sorted four rounds against either IL-17 A or IL-17 F alone. For alternative sorting, phage libraries were sorted against IL-17A and IL-17 F interchangeably in alternative rounds. Nunc 96 well Maxisorp immunoplates were coated overnight at 4° C. with target antigen (10 µg/ml) and were blocked for 1 hour at room temperature with phage blocking buffer PBST (phosphate-buffered saline (PBS) and 1% (w/v) bovine serum albumin (BSA) and 0.05% (v/v) tween-20). Antibody phage libraries VH (see, e.g., Lee et al., J. Immunol. Meth. 284:119-132, 2004) and VH/VL (see Liang et al., JMB. 366: 815-829, 2007) were added to antigen plates separately and incubated overnight at room temperature. The following day antigen-coated plates were washed ten times with PBT (PBS with 0.05% Tween-20), and bound phage were eluted with 50 mM HCl and 500 mM NaCl for 30 minutes and neutralized with an equal volume of 1 M Tris base (pH7.5). Recovered phages were amplified in *E. coli* XL-1 Blue cells. During the subsequent selection rounds, incubation of antibody phage with the antigen-coated plates was reduced to 2-3 hours, and the stringency of plate washing was gradually increased.

After 4 rounds of panning, significant enrichment was observed. 96 clones were picked each from VH and VH/VL library sorting to determine whether they specifically bound to both human IL-17 A and IL-17 F. The variable regions of these clones were PCR sequenced to identify unique sequence clones.

The affinities of phage antibodies were ranked using spot competition ELISA. The phage antibody IC50 values were further determined using competitive phage-binding ELISA. Unique phage antibodies that bind both human IL-17 A and IL-17 F with highest IC50 were chosen and reformatted to full length IgGs for evaluation in in vitro cell assay.

Clones of interest were reformatted into IgGs by cloning $V_L$ and $V_H$ regions of individual clones into the LPG3 and LPG4 vector respectively, transiently expressing in mammalian CHO cells, and purifying with a protein A column.

Determination of IC50/90 of Cross-Reactive Antibodies

Human neonatal foreskin fibroblasts (Invitrogen) were seeded in 96-well plate at $2\times10^4$ cells/150 µl media/well on day 1. Media was replaced with cytokine/antibody containing media (150 µl) on day 2. Recombinant human IL-17A was used at 5 ng/ml. Recombinant human IL-17F was used at 50 ng/ml. Recombinant human IL-17A/F heterodimer was purified in-house and was used at 25 ng/ml. Supernatant was harvested 24 hours later and G-CSF ELISA was performed to measure G-CSF induction. Data was plotted in PRISM and IC50/90 values calculated using the same software.

Construct Libraries for Affinity Improvement of Clones Derived from the $V_H$ Library Phagemid pW0703 (derived from phagemid pV0350-2b (Lee et al., *J. Mol. Biol.* 340, 1073-1093 (2004)), containing stop codon (TAA) in all CDR-L3 positions and displaying monovalent Fab on the surface of M13 bacteriophage) served as the library template for grafting heavy chain variable domains ($V_H$) of clones of interest from the $V_H$ library for affinity maturation. Both hard and soft randomization strategies were used for affinity maturation. For hard randomization, one light chain library with selected positions of the three light chain CDRs was randomized using amino acids designed to mimic natural human antibodies and the designed DNA degeneracy was as described in Lee et al. (*J. Mol. Biol.* 340, 1073-1093 (2004)). For soft randomization, residues at positions 91-94, and 96 of CDR-L3, 28-31 and 34-35 of CDR-H1, 50, 52, and 53-58 of CDR-H2, 95-99 and 100A of CDR-H3, were targeted; and two different combinations of CDR loops, L3/H1/H2 and L3/H3, were selected for randomization. To achieve the soft randomization conditions, which introduced the mutation rate of approximately 50% at the selected positions, the mutagenic DNA was synthesized with 70-10$^{-10}$-10 mixtures of bases favoring the wild type nucleotides (Gallop et al., *Journal of Medicinal Chemistry* 37:1233-1251 (1994)).

Phage Sorting Strategy to Generate Affinity Improvement

For affinity improvement selection, phage libraries were subjected to plate sorting for the first round, followed by four or five rounds of solution sorting. The libraries were sorted individually against human IL-17 A and IL-17 F, separately. For the first round of plate sorting, the libraries were sorted against target coated plate (NUNC Maxisorp plate) with phage input about 3 O.D./ml in 1% BSA and 0.05% Tween 20 for 2 hours at room temperature. After the first round of plate sorting, solution sorting was performed to increase the stringency of selection. For solution sorting, 1 O.D./ml phage propagated from the first round of plate sorting were incubated with 100 nM biotinylated target protein (the concentration is based on parental clone phage IC50 value) in 100 µl buffer containing 1% Superblock (Pierce Biotechnology) and 0.05% Tween20 for 30 minutes at room temperature. The mixture was further diluted 10× with 1% Superblock, and 100 µl/well was applied to neutravidin-coated wells (5 µg/ml) for 15 minutes at room temperature with gentle shaking such that biotinylated target bound phage. The wells were washed with PBS-0.05% Tween 20 ten times. To determine background binding, control wells containing phage with targets that were not biotinylated were captured on neutravidin-coated plates. Bound phage was eluted with 0.1N HCl for 20 minutes, neutralized by 1/10 volume of 1M Tris pH11, titered, and propagated for the next round. Next, five more rounds of solution sorting were carried out together with increasing selection stringency. The first of which is for on-rate selection by decreasing biotinylated target protein concentration from 10 nM to 1 nM, and the second of which is for off-rate selection by adding excess amounts of non-biotinylated target protein (100 fold more) to compete off weaker binders either at room temperature. Also, the phage input was decreased (0.1~0.5 O.D/ml) to lower background phage binding.

High Throughput Affinity Screening ELISA (Single Spot Competition)

Colonies were picked from the fifth or sixth round screens. Colonies were grown overnight at 37° C. in 150 µl/well of 2YT media with 50 µg/ml carbenicillin and 1E10/ml KO7 in 96-well plate (Falcon). From the same plate, a colony of XL-1 infected parental phage was picked as control. 96-well Nunc Maxisorp plates were coated with 100 µl/well of human IL-17 A and IL-17 F (2 µg/ml) separately in PBS at 4° C. overnight or room temperature for 2 hours. The plates were blocked with 65 µl of 1% BSA for 30 min and 40 µl of 1% Tween 20 for another 30 minutes.

The phage supernatant was diluted 1:10 in ELISA (enzyme linked immunosorbent assay) buffer (PBS with 0.5% BSA, 0.05% Tween20) with or without 10 nM target protein in 100 µl total volume and incubated at least 1 hour at room temperature in an F plate (NUNC). 75 µl of mixture with or without target protein was transferred side by side to the target protein coated plates. The plate was gently shaken for 15 min to allow the capture of unbound phage to the target protein-coated plate. The plate was washed at least five times with PBS-0.05% Tween 20. The binding was quantified by adding horseradish peroxidase (HRP)-conjugated anti-M13 antibody in ELISA buffer (1:5000) and incubated for 30 minutes at room temperature. The plates were washed with PBS-0.05% Tween 20 at least five times. Next, 100 µl/well of a 1:1 ratio of 3,3',5,5'-tetramethylbenzidine (TMB) Peroxidase substrate and Peroxidase Solution B ($H_2O_2$) (Kirkegaard-Perry Laboratories (Gaithersburg, Md.)) was added to the well and incubated for 5 minutes at room temperature. The reaction was stopped by adding 100 µl 1M Phosphoric Acid ($H_3PO_4$) to each well and allowed to incubate for 5 minutes at room temperature. The OD (optical density) of the yellow color in each well was determined using a standard ELISA plate reader at 450 nm. The OD reduction (%) was calculated by the following equation.

$$OD_{450nm} \text{ reduction}(\%) = [(OD_{450nm} \text{ of wells with competitor})/(OD_{450nm} \text{ of well with no competitor})]*100$$

In comparison to the $OD_{450nm}$ reduction (%) of the well of parental phage (100%), clones that had the $OD_{450nm}$ reduction (%) lower than 50% for both the human and murine target were picked for sequence analysis. Unique clones were selected for phage preparation to determine binding affinity (phage IC50) against both human IL-17A and IL-17F by comparison with parental clones. Then the most affinity-improved clones were reformatted into human IgG1 for antibody production and further BIAcore binding kinetic analysis and other in vitro or in vivo assay.

Characterization of Anti IL-17A/F Antibodies (Biacore)

Binding affinities of anti IL-17 A/F IgGs were measured by Surface Plasmon Resonance (SRP) using a BIAcore™-3000 instrument. Anti IL-17 A/F human IgG was captured by mouse anti-human Fc antibody (GE Healthcare, cat #BR-1008-39) coated on CM5 biosensor chips to achieve approximately 200 response units (RU). For kinetics measurements, two-fold serial dilutions (0.98 nM to 125 nM) of human IL-17A (R&D Systems, cat #317-IL-050/CF), IL-17 F (R&D, cat #1335-IL-025/CF), IL-17A/F (GNE), Rhesus IL-17F (GNE), Cyno IL-17A (PUR17200) were injected in PBT buffer (PBS with 0.05% Tween 20) at 25° C. with a flow rate of 30 µl/min. Association rates ($k_{on}$) and dissociation rates ($k_{off}$) were calculated using a simple one-to-one Langmuir binding model (BIAcore Evaluation Software version 3.2). The equilibrium dissociation constant ($K_D$) was calculated as the ratio $k_{off}/k_{on}$.

Results

As discussed earlier, IL-17A & IL17-F are major pro-inflammatory cytokines secreted by Th17 T cell subset. They target almost all the cell types in body and induce tissue inflammation and tissue damage. The goal of the work described in the present example has been to generate cross-reactive antibodies that can block both IL-17A & F with high potency and cross-species reactivity.

Figure 5A:
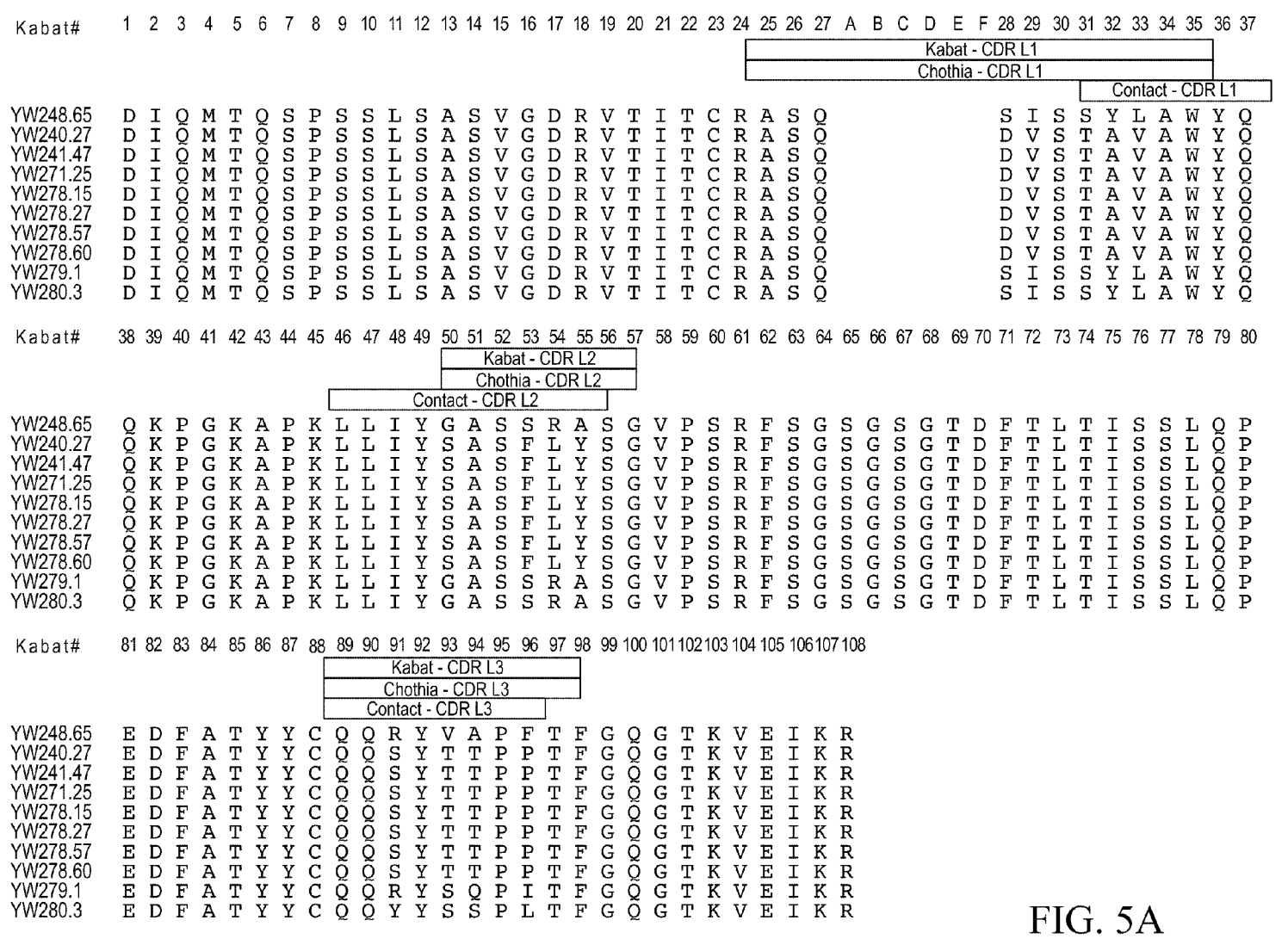
Figure 5B:
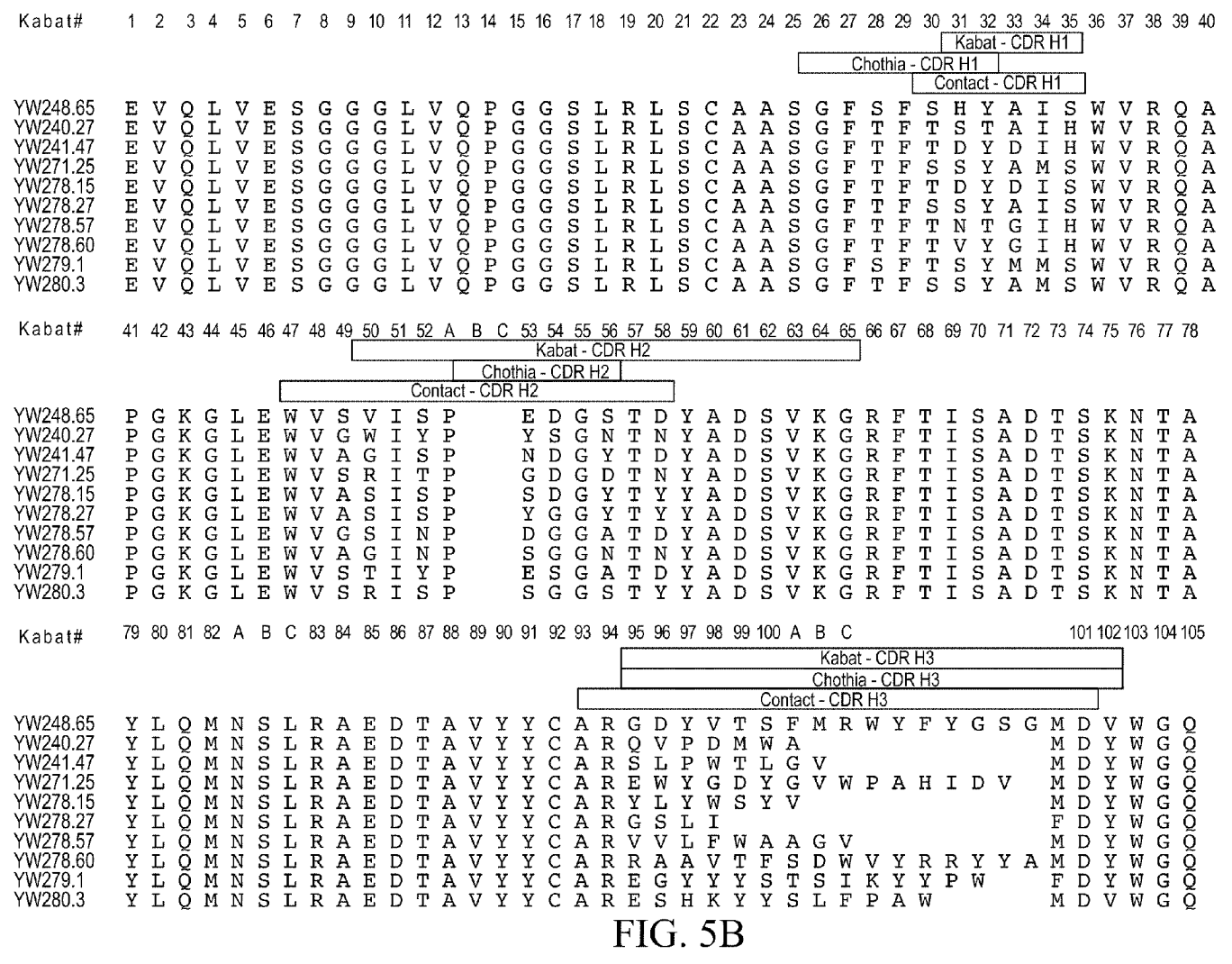

The light chain variable region sequences of cross-reactive anti-IL-17A/F clones are shown in FIG. 5A (SEQ ID NOs: 5-14), including the CDRL1, CDRL2, and CDRL3 sequences. The heavy chain variable region sequence of cross-reactive anti-IL-17A/F clones are shown in FIG. 5B (SEQ ID NOs: 51-60). Of the cross-reactive clones identified YW241.47, YW278.15 and YW279.1 showed particularly strong binding to both IL-17A and IL-17F, both in monodimeric and heterodimeric form. It is noteworthy that cross-reactive antibodies YW278.15 and 279.1 show nearly equal blocking of IL-17A and F. Of these, cross-reactive antibody YW278.15 was selected for affinity maturation.

Light chain variable region sequences of further cross-reactive anti-17A/F antibodies, including affinity matured variants of YW278.15 and YW279.1, are shown in FIG. 5C (SEQ ID Nos: 63-68).

Heavy chain variable region sequences of further cross-reactive anti-A/F antibodies, including affinity matured variants of YW278.15 and YW279.1, are shown in FIG. 5D (SEQ ID Nos: 69-74).

FIG. 6 shows the alignment of light chain sequences of IL-17A/F cross-reactive antibody YW278.15 (SEQ ID NO: 9) and its affinity matured variants, YW278.15.18 (SEQ ID NO: 15), YW278.15.2 (SEQ ID NO: 16), and YW278.15.3 (SEQ ID NO: 17). The CDRL1, CDRL2 and CDRL3 sequences are boxed.

FIG. 7 shows the alignment of the heavy chain sequences of IL-17A/F cross-reactive antibody YW278.15 (SEQ ID NO: 92) and its affinity matured variants, YW278.15.18 (SEQ ID NO: 93), YW278.15.2 (SEQ ID NO: 94), 278.15.2.D54E (SEQ ID NO: 95), YW278.15.3 (SEQ ID NO: 92), YW278.15.18C55A (SEQ ID NO: 18) and YW278.15.18C55S (SEQ ID NO: 19). The CDRL1, CDRL2 and CDRL3 sequences are boxed. YW278.15.18C55A and YW278.15.18C55S have the same light chain as YW278.15.18, and the C55A and C55S mutations in the antibody heavy chains were introduced to facilitate manufacturing.

FIG. 8A shows the results of the BIAcore™ immunoassay performed with three affinity matured IL-17A/F cross-reactive antibodies, YW278.15.2, YW278.15.18, and YW278.15.3. The binding affinities to recombinant human IL-17A (rhIL-17A), recombinant human IL-17F (rhIL-17F), cyno IL-17F and human IL-17A/F in solution (Kd (M)) are shown in the last column.

FIG. 8B shows the results of the BIAcore™ immunoassay performed with affinity matured IL-17A/F cross-reactive antibodies, YW278.15.2.D54E; YW278.15.3; YW278.15.9; YW279.1.20; YW279.1.21; YW279.1.22. The binding affinities to recombinant human IL-17A (rhIL-17A), recombinant human IL-17F (rhIL-17F), cyno IL-17A, cyno IL-17F and human IL-17A/F in solution (Kd (M)) are shown in the last column.

FIG. 9 shows the results of the BIAcore™ immunoassay performed with two further affinity matured IL-17A/F cross-reactive antibodies, YW278.15.18.C55A and YW278.15.18.C55S, in comparison to YW278.15.18. The binding affinities to recombinant human IL-17A (rhIL-17A), recombinant human IL-17F (rhIL-17F), cyno IL-17F, and human IL-17A/F in solution (Kd (M)) are shown in the last column.

FIG. 10 shows the results of the BIAcore™ immunoassay performed with three affinity matured IL-17A/F cross-reactive antibodies, using rhesus IL-17A as the target. The binding affinities to rhesus IL-17A are shown in the last column.

FIGS. 13A and 13B show IC50 and IC90 data for a set of cross-reactive antibodies, as determined in repeated assays. The antibody to target cytokine molar ratios are also shown.

The results show that affinity of YW278.15 and 279.1 was improved through CDR randomization to both IL-17A and IL-17F. Of the cross-reactive antibodies tested, YW278.15.2 and YW278.15.18 showed best improvement in affinity and in cell blocking activity. Both YW278.15.2 and YW278.15.18 have similar activity to IL17-A and IL-17F.

Example 2

Anti-IL-17A/F Bispecific Antibodies

Materials and Methods

Library Sorting and Screening to Identify Anti-IL-17A/F Antibodies

Human IL-17A (R&D Systems, cat #317-IL-050/CF) and IL-17 F (R&D Systems, cat #1335-IL-025/CF) were used as antigens for library sorting. For conventional sorting, the phage libraries were sorted four rounds against either IL-17 A or IL-17 F alone. For alternative sorting, phage libraries were sorted against IL-17A and IL-17 F interchangeably in alternative rounds. Nunc 96 well Maxisorp immunoplates were coated overnight at 4° C. with target antigen (10 μg/ml) and were blocked for 1 hour at room temperature with phage blocking buffer PBST (phosphate-buffered saline (PBS) and 1% (w/v) bovine serum albumin (BSA) and 0.05% (v/v) tween-20). Antibody phage libraries VH (see, e.g., Lee et al., J. Immunol. Meth. 284:119-132, 2004) and VH/VL (see Liang et al., JMB. 366: 815-829, 2007) were added to antigen plates separately and incubated overnight at room temperature. The following day antigen-coated plates were washed ten times with PBT (PBS with 0.05% Tween-20), and bound phage were eluted with 50 mM HCl and 500 mM NaCl for 30 minutes and neutralized with an equal volume of 1 M Tris base (pH7.5). Recovered phages were amplified in $E.\ coli$ XL-1 Blue cells. During the subsequent selection rounds, incubation of antibody phage with the antigen-coated plates was reduced to 2-3 hours, and the stringency of plate washing was gradually increased.

After 4 rounds of panning, significant enrichment was observed. 96 clones were picked each from VH and VH/VL library sorting to determine whether they specifically bound to both human IL-17 A and IL-17 F. The variable regions of these clones were PCR sequenced to identify unique sequence clones.

The affinities of phage antibodies were ranked using spot competition ELISA. The phage supernatant was diluted 1:5 in ELISA (enzyme linked immunosorbent assay) buffer (PBS with 0.5% BSA, 0.05% Tween20) with or without 50 nM target protein in 100 μl total volume and incubated at least 1 hour at room temperature in an F plate (NUNC). 75 μl of mixture with or without target protein was transferred side-by-side to the target protein coated plates (1 ug/ml IL-17A or IL-17F coated overnight). The plate was gently shaken for 15 min to allow the capture of unbound phage to the target protein-coated plate. The plate was washed ten times with PBS-0.05% Tween 20. The binding was quantified by adding horseradish peroxidase (HRP)-conjugated anti-M13 antibody in ELISA buffer (1:5000) and incubated for 30 minutes at room temperature. The plates were washed ten times with PBS-0.05% Tween 20. Next, 100 μl/well of a 1:1 ratio of 3,3',5,5'-tetramethylbenzidine (TMB) Peroxidase substrate and Peroxidase Solution B ($H_2O_2$) (Kirkegaard-Perry Laboratories (Gaithersburg, Md.)) was added to the well and incubated for 5 minutes at room temperature. The reaction was stopped by adding 100 μl 0.1M phosphoric Acid ($H_3PO_4$) to each well and allowed to incubate for 5 minutes at room temperature. The OD (optical density) of the yellow color in each well was determined using a standard ELISA plate reader at 450 nm. The OD reduction (%) was calculated by the following equation.

$OD_{450nm}$ reduction(%)=[($OD_{450nm}$ of wells with competitor)/($OD_{450nm}$ of well with no competitor)]*100

In comparison to the $OD_{450nm}$ reduction (%) of the well of parental phage (100%), clones that had the $OD_{450nm}$ reduction (%) lower than 60% for either IL-17A or IL-17F target were picked and reformatted into full length human IgG1 by cloning $V_L$ and $V_H$ regions of individual clones into the LPG3 and LPG4 vector respectively, transiently expressing in mammalian CHO cells, and purifying with a protein A column. Bi-specific antibody (one arm of the antibody specific for IL-17A and the other specific for IL-17F) was constructed using the knob-and-hole technology (see Merchant et al., Nature Biotechnology, 16:677-681, 1998 and Atwell S. et al., J Mol Biol 270(1):2635 (1997)). These mono- and bi-specific antibodies were then used for evaluation in in vitro cell assay and BIAcore binding kinetic analyses.

Characterization of Anti IL-17A/F Antibodies (Biacore)

Binding affinities of anti IL-17 A/F IgGs were measured by Surface Plasmon Resonance (SRP) using a BIAcore™-3000 instrument. Anti IL-17 A/F human IgG was captured by mouse anti-human Fc antibody (GE Healthcare, cat #BR-1008-39) coated on CM5 biosensor chips to achieve approximately 200 response units (RU). For kinetics measurements, two-fold serial dilutions (0.245 nM to 500 nM) of human IL-17A (R&D Systems, cat #317-IL-050/CF) or IL-17 F (R&D, cat #1335-IL-025/CF) were injected in PBT buffer (PBS with 0.05% Tween 20) at 25° C. with a flow rate of 30 μl/min. Association rates ($k_{on}$) and dissociation rates ($k_{off}$) were calculated using a simple one-to-one Langmuir binding model (BIAcore Evaluation Software version 3.2). The equilibrium dissociation constant ($K_D$) was calculated as the ratio $k_{off}/k_{on}$.

Results

FIG. 11 shows the alignment of the light chain variable region sequences of IL-17A specific antibody YW264.21 (SEQ ID NO: 20) and IL-17F specific antibody YW265.01 (SEQ ID NO: 21).

FIG. 12 shows the alignment of the heavy chain variable region sequences of IL-17A specific antibody YW264.21 (SEQ ID NO: 22) and IL-17F specific antibody YW265.01 (SEQ ID NO: 23).

FIG. 14 shows IL-17A and IL-17F binding affinity data for an IL-17A/F bispecific antibody in comparison with anti-IL-17A antibody YW264.21 and anti-IL-17F antibody YW265.01.

FIG. 15 shows the alignment of the light chain variable region sequences of IL-17A specific antibodies YW264.21 (SEQ ID NO: 20) and YW264.03 (SEQ ID NO: 61) and IL-17F specific antibody YW265.01 (SEQ ID NO: 21).

FIG. 16 shows the alignment of the heavy chain variable region sequences of IL-17A specific antibodies YW264.21 (SEQ ID NO: 22) and YW264.03 (SEQ ID NO: 62) and IL-17F specific antibody YW265.01 (SEQ ID NO: 23).

Example 3

Crystal Structure of IL-17F-Fab Complex

Materials & Methods

Protein Expression:

IL-17F was expressed and purified as described in Hymowitz S G, et al., EMBO J., 2001, 20:5332-5341. Briefly, DNA encoding 1L-17F was subcloned into pET15b (Novagen) sites in order to introduce an N-terminal His-tag and thrombin cleavage site. After another PCR step, the coding region was subcloned into the baculovirus transfer vector pAcGP67B (PharMingen), which was then co-transfected with BaculoGold DNA (PharMingen) into Sf9 cells, and recombinant virus was isolated and amplified in Sf9 cells. For protein production, Hi5 cells were infected with amplified baculovirus. The medium was harvested by centrifugation and the pH was adjusted to 7.0. The medium was filtered and loaded onto a Ni-NTA column. Fractions containing IL-17F were eluted with imidazole, pooled and dialyzed into PBS, pH 6.5, together with thrombin overnight at 4° C. The protein sample was then concentrated and the thrombin and His-tag were removed by purification over a size exclusion column.

The Fab fragment of YW 278.15.18.C55S (hereafter referred to as "fab") was expressed in E. coli, purified using Protein G-Sepharose, and eluted with 0.58% acetic acid. Fab-containing fractions were then purified using a SP HiTrap column (GE Healthcare) with 20 mM MES pH 5.5 and a NaCl gradient. Final buffer was 25 mM Tris, 100 mM NaCl, pH7.5.

Complex Purification:

Purified fab was mixed with an excess of purified recombinant IL17F. The complex was purified by passage over a size exclusion column. Fractions containing complex were pooled and concentrated to 25 mg/mL.

Crystallization:

The IL-17F-fab complex was crystallized using vapor diffusion using hanging drops. The hanging drop was set up by mixing 2 ul of protein and 2 ul of well solution (40% MPD, 5% PEG 8000, and 0.1 M Na Cacodylate pH6.5) at 19° C. Crystals grew after 5 days incubation, and were washed and frozen directly in mother liquid in liquid nitrogen.

Crystallographic Data and Refinement:

Crystallographic data was collected beamline 11-1 at the Stanford Synchtron Radiation Laboratory. The data sets were processed using the programs in the HKL package (HKL, Charlottesville, Va.). The structure was solved by molecular replacement using the program PHASER (CCP4) using a variant of the humanized 4D5 Fab (PDB code 1FVE) as the search model followed by refinement with REFMAC5 (CCP4). The final model has excellent geometry with 99.6% of all residues in the most favored or additional allowed regions of a Ramachandran plot and only 0.6% (6 residues) in either the generously allowed or disallowed regions.

TABLE 1

| X-Ray Data collection and refinement statistics. | |
|---|---|
| | Human IL-17F-Fab complex |
| Data collection | |
| Space group | $P2_12_12$ |
| Cell dimensions | |
| a, b, c (Å) | 150.4, 90.0, 120.7 |
| Resolution (Å) | 50-2.90 (3.00-2.90) |
| $R_{sym}$ | 13.7 (48.0) |
| <I>/<☐I> | 13.8 (2.4) |
| Completeness (%) | 98.3 (90.3) |
| Redundancy | 6.9 (4.6) |
| Refinement | |
| Resolution (Å) | 50-2.90 |
| Complex in asu | 2 fab bound to one IL-17F dimer |
| No. reflections | 30,991 |
| $R_{work}/R_{free}$ (%) | 21.6, 25.8 |
| No. atoms | |
| Protein | 8446 |
| Solvent | — |
| R.m.s. deviations | |
| Bond lengths (Å) | 0.007 |
| Bond angles (°) | 1.56 |

*Values in parentheses are for highest-resolution shell.

Figure 18:
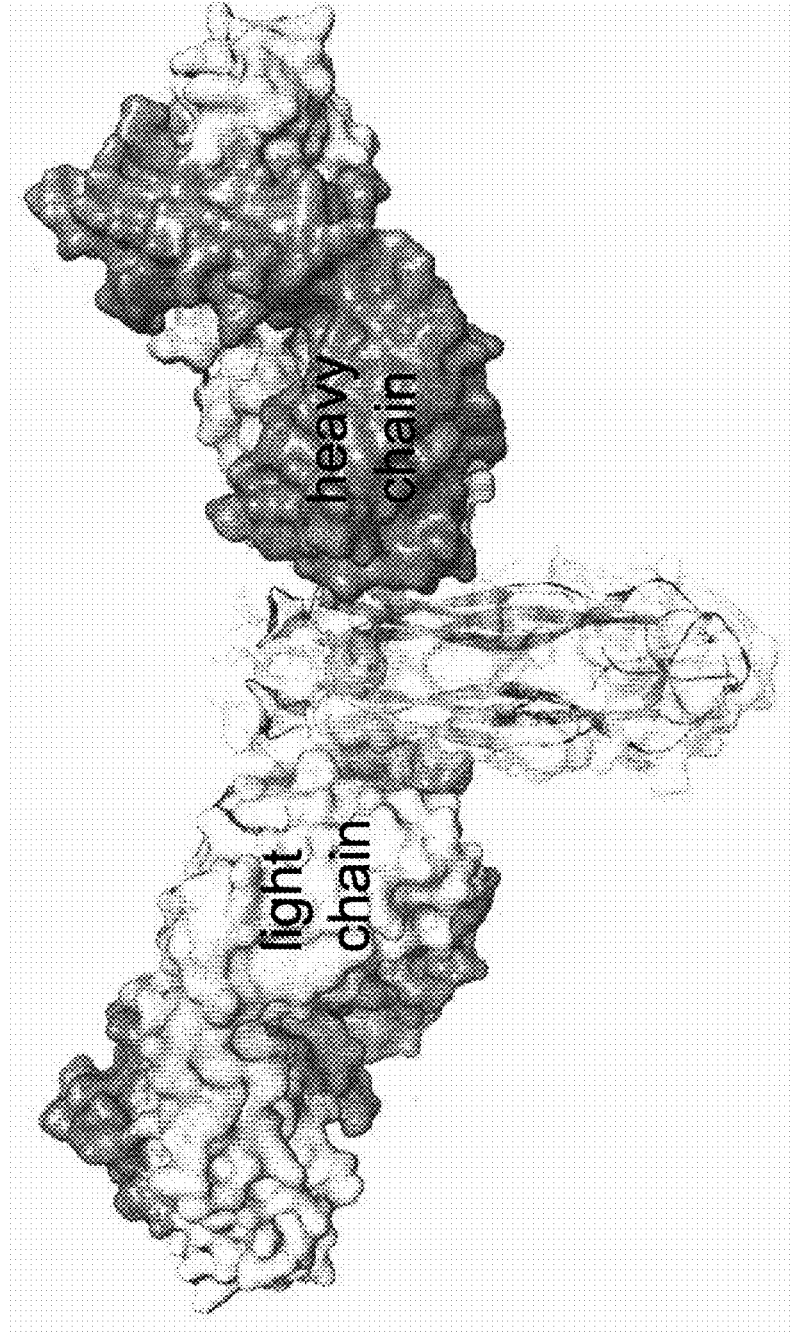
FIG. 18 shows the epitope for Fab on the IL-17F dimer.

FIG. 17 shows the Fab bound to an IL-17F dimer, and FIG. 18 shows the epitope for Fab on the IL-17F dimer. The epitope is centered on a cysteine knot, and is largely conserved between L17A and IL17F (residues in parenthesis are sequence differences between F and A).

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. Indeed, various modifications of the invention in addition to those shown and described herein will become apparent to those skilled in the art from the foregoing description and fall within the scope of the appended claims.

What is claimed is:

1. An isolated antibody or an antigen-binding fragment thereof that specifically binds to IL-17A and IL-17F and inhibits the biological function of both IL-17A and IL-17F, comprising a light chain variable domain comprising CDRL1, CDRL2, and CDRL3 regions, and a heavy chain variable domain comprising CDRH1, CDRH2, and CDRH3 regions, wherein (a) CDRL1 comprises the sequence DVSTAVA (SEQ ID NO:24), CDRL2 comprises the sequence SASFLYS (SEQ ID NO:26), and CDRL3 comprises the sequence SYTTPPT (SEQ ID NO:28), and
CDRH1 comprises the sequence of GFTFTDYDIS (SEQ ID NO:35), CDRH2 comprises the sequence of SDGY-TYYADSVKG (SEQ ID NO:37), and CDRH3 comprises the sequence YLYWSYV (SEQ ID NO:40); or (b) CDRL1 comprises the sequence VISSSLA (SEQ ID NO:33), CDRL2 comprises the sequence GASFFYS (SEQ ID NO:96), and CDRL3 comprises the sequence HNDLPLT (SEQ ID NO:32), and
CDRH1 comprises the sequence of GFTFTDYDIS (SEQ ID NO:35), CDRH2 comprises the sequence SDGY-TYYADSVKG (SEQ ID NO:37), and CDRH3 comprises the sequence YLYWSYV (SEQ ID NO:40).

2. The isolated antibody or antigen-binding fragment of claim 1 comprising the light chain variable region of antibody YW278.15 (SEQ ID NO: 9) and the heavy chain variable region of antibody YW278.15 (SEQ ID NO: 55).

3. The antibody or antigen-binding fragment of claim 1, which binds to IL-17A and IL-17F with substantially the same binding affinity.

4. The antibody or antigen-binding fragment of claim 1, which binds IL-17A and IL-17F with a binding affinity of at least about $10^{-10}$ to $10^{-11}$ M.

5. The antibody or antigen-binding fragment of claim 1, which binds a monomer, a homodimer or a heterodimer of IL-17A and/or IL-17F.

6. The antibody or antigen-binding fragment of claim 1, which is monoclonal.

7. The antibody or antigen-binding fragment of claim 6, which is chimeric, or humanized.

8. The antibody or antigen-binding fragment of claim 7 wherein said antigen-binding fragment is selected from the group consisting of Fab, Fab', F(ab')$_2$, and Fv fragments; diabodies; and single-chain antibody molecules.

9. The antibody or antigen-binding fragment of claim 6, which inhibits the biological function of a heterodimer of IL-17A and IL-17F.

10. A pharmaceutical composition comprising the antibody or antigen-binding fragment according to claim 6 in admixture with a pharmaceutically acceptable excipient.

11. An article of manufacture, comprising: (a) a container; (b) a label on said container; and (c) a composition of matter comprising the antibody or antigen-binding fragment according to claim 6, contained within said container, wherein said label on said container indicates that said composition of matter can be used for treating an inflammatory or an immune related disease.

\* \* \* \* \*

SEQUENCE LISTING

```
<160> NUMBER OF SEQ ID NOS: 96

<210> SEQ ID NO 1
<211> LENGTH: 468
<212> TYPE: DNA
<213> ORGANISM: Homo sapiens

<400> SEQUENCE: 1
atgactcctg ggaagacctc attggtgtca ctgctactgc tgctgagcct ggaggccata      60
gtgaaggcag aatcacaat cccacgaaat ccaggatgcc caaattctga ggacaagaac     120
ttcccccgga ctgtgatggt caacctgaac atccataacc ggaataccaa taccaatccc    180
aaaaggtcct cagattacta caaccgatcc acctcaccttt ggaatctcca ccgcaatgag    240
gaccctgaga gatatccctc tgtgatctgg gaggcaaagt gccgccactt gggctgcatc    300
aacgctgatg gaaacgtgga ctaccacatg aactctgtcc ccatccagca agagatcctg    360
gtcctgcgca gggagcctcc acactgcccc aactccttcc ggctggagaa gatactggtg    420
tccgtgggct gcacctgtgt caccccgatt gtccaccatg tggcctaa                  468

<210> SEQ ID NO 2
<211> LENGTH: 155
<212> TYPE: PRT
<213> ORGANISM: Homo sapiens

<400> SEQUENCE: 2

Met Thr Pro Gly Lys Thr Ser Leu Val Ser Leu Leu Leu Leu Leu Ser
1               5                   10                  15

Leu Glu Ala Ile Val Lys Ala Gly Ile Thr Ile Pro Arg Asn Pro Gly
                20                  25                  30

Cys Pro Asn Ser Glu Asp Lys Asn Phe Pro Arg Thr Val Met Val Asn
            35                  40                  45

Leu Asn Ile His Asn Arg Asn Thr Asn Thr Asn Pro Lys Arg Ser Ser
        50                  55                  60

Asp Tyr Tyr Asn Arg Ser Thr Ser Pro Trp Asn Leu His Arg Asn Glu
65                  70                  75                  80

Asp Pro Glu Arg Tyr Pro Ser Val Ile Trp Glu Ala Lys Cys Arg His
                85                  90                  95

Leu Gly Cys Ile Asn Ala Asp Gly Asn Val Asp Tyr His Met Asn Ser
            100                 105                 110

Val Pro Ile Gln Gln Glu Ile Leu Val Leu Arg Arg Glu Pro Pro His
        115                 120                 125

Cys Pro Asn Ser Phe Arg Leu Glu Lys Ile Leu Val Ser Val Gly Cys
    130                 135                 140

Thr Cys Val Thr Pro Ile Val His His Val Ala
145                 150                 155

<210> SEQ ID NO 3
<211> LENGTH: 492
<212> TYPE: DNA
```

-continued

<213> ORGANISM: Homo sapiens

<400> SEQUENCE: 3

```
atgacagtga agaccctgca tgggcccagcc atggtcaagt acttgctgct gtcgatattg    60
gggcttgcct ttctgagtga ggcggcagct cggaaaatcc ccaaagtagg acatactttt   120
ttccaaaagc ctgagagttg cccgcctgtg ccaggaggta gtatgaagct tgacattggc   180
atcatcaatg aaaaccagcg cgtttccatg tcacgtaaca tcgagagccg ctccaccctcc  240
ccctggaatt acactgtcac ttgggacccc aaccggtacc cctcggaagt tgtacaggcc   300
cagtgtagga acttgggctg catcaatgct caaggaaagg aagacatctc catgaattcc   360
gttcccatcc agcaagagac cctggtcgtc cggaggaagc accaaggctg ctctgtttct   420
ttccagttgg agaaggtgct ggtgactgtt ggctgcacct gcgtcacccc tgtcatccac   480
catgtgcagt aa                                                        492
```

<210> SEQ ID NO 4
<211> LENGTH: 163
<212> TYPE: PRT
<213> ORGANISM: Homo sapiens

<400> SEQUENCE: 4

```
Met Thr Val Lys Thr Leu His Gly Pro Ala Met Val Lys Tyr Leu Leu
1               5                   10                  15

Leu Ser Ile Leu Gly Leu Ala Phe Leu Ser Glu Ala Ala Ala Arg Lys
            20                  25                  30

Ile Pro Lys Val Gly His Thr Phe Phe Gln Lys Pro Glu Ser Cys Pro
        35                  40                  45

Pro Val Pro Gly Gly Ser Met Lys Leu Asp Ile Gly Ile Ile Asn Glu
    50                  55                  60

Asn Gln Arg Val Ser Met Ser Arg Asn Ile Glu Ser Arg Ser Thr Ser
65                  70                  75                  80

Pro Trp Asn Tyr Thr Val Thr Trp Asp Pro Asn Arg Tyr Pro Ser Glu
                85                  90                  95

Val Val Gln Ala Gln Cys Arg Asn Leu Gly Cys Ile Asn Ala Gln Gly
            100                 105                 110

Lys Glu Asp Ile Ser Met Asn Ser Val Pro Ile Gln Gln Glu Thr Leu
        115                 120                 125

Val Val Arg Arg Lys His Gln Gly Cys Ser Val Ser Phe Gln Leu Glu
    130                 135                 140

Lys Val Leu Val Thr Val Gly Cys Thr Cys Val Thr Pro Val Ile His
145                 150                 155                 160

His Val Gln
```

<210> SEQ ID NO 5
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30
```

Leu Ala Trp Tyr Gln Gln Lys Pro Gly Lys Ala Pro Lys Leu Leu Ile
            35                  40                  45

Tyr Gly Ala Ser Ser Arg Ala Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Tyr Val Ala Pro Phe
                85                  90                  95

Thr Phe Gly Gln Gly Thr Lys Val Glu Ile Lys Arg
                100                 105

<210> SEQ ID NO 6
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys Arg
                100                 105

<210> SEQ ID NO 7
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys Arg
            100                 105

<210> SEQ ID NO 8
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys Arg
            100                 105

<210> SEQ ID NO 9
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys Arg
            100                 105

<210> SEQ ID NO 10
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys Arg
            100                 105

<210> SEQ ID NO 11
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys Arg
            100                 105

<210> SEQ ID NO 12
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Pro Pro
                85                  90                  95

Thr Phe Gly Gln Gly Thr Lys Val Glu Ile Lys Arg
            100                 105

<210> SEQ ID NO 13
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Gly Ala Ser Ser Arg Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Tyr Ser Gln Pro Ile
                85                  90                  95

Thr Phe Gly Gln Gly Thr Lys Val Glu Ile Lys Arg
            100                 105

<210> SEQ ID NO 14
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Gly Ala Ser Ser Arg Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Ser Pro Leu
                85                  90                  95

Thr Phe Gly Gln Gly Thr Lys Val Glu Ile Lys Arg
            100                 105

<210> SEQ ID NO 15
<211> LENGTH: 108

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Ala Lys Leu
                85                  90                  95

Thr Phe Gly Gln Gly Thr Lys Val Glu Ile Lys Arg
                100                 105

<210> SEQ ID NO 16
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Ala
                85                  90                  95

Thr Phe Gly Gln Gly Thr Lys Val Glu Ile Lys Arg
                100                 105

<210> SEQ ID NO 17
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Val Ile Ser Ser Ser
```

```
                    20                  25                  30

Leu Ala Trp Tyr Gln Gln Lys Pro Gly Lys Ala Pro Lys Leu Leu Ile
            35                  40                  45

Tyr Gly Ala Ser Phe Phe Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln His Asn Asp Leu Pro Leu
                85                  90                  95

Thr Phe Gly Gln Gly Thr Lys Val Glu Ile Lys Arg
                100                 105

<210> SEQ ID NO 18
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Asp Tyr
            20                  25                  30

Asp Ile Ser Trp Val Arg Gln Ala Pro Gly Lys Gly Leu Glu Trp Val
        35                  40                  45

Ala Ser Ile Ser Pro Pro Asp Ala Tyr Thr Tyr Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                85                  90                  95

Ala Arg Tyr Leu Tyr Trp Ser Tyr Val Met Asp Tyr Trp Gly Gln Gly
                100                 105                 110

Thr Leu Val Thr Val Ser Ser
        115

<210> SEQ ID NO 19
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Asp Tyr
            20                  25                  30

Asp Ile Ser Trp Val Arg Gln Ala Pro Gly Lys Gly Leu Glu Trp Val
        35                  40                  45

Ala Ser Ile Ser Pro Pro Asp Ser Tyr Thr Tyr Tyr Ala Asp Ser Val
 50                  55                  60

Lys Gly Arg Phe Thr Ile Ser Ala Asp Thr Ser Lys Asn Thr Ala Tyr
 65                  70                  75                  80
```

```
Leu Gln Met Asn Ser Leu Arg Ala Glu Asp Thr Ala Val Tyr Tyr Cys
                85                  90                  95

Ala Arg Tyr Leu Tyr Trp Ser Tyr Val Met Asp Tyr Trp Gly Gln Gly
            100                 105                 110

Thr Leu Val Thr Val Ser Ser
        115

<210> SEQ ID NO 20
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Gly Ala Ser Ser Arg Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Ser Pro Leu
                85                  90                  95

Thr Phe Gly Gln Gly Thr Lys Val Glu Ile Lys Arg
            100                 105

<210> SEQ ID NO 21
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Gly Ala Ser Ser Arg Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Ser Pro Leu
                85                  90                  95

Thr Phe Gly Gln Gly Thr Lys Val Glu Ile Lys Arg
            100                 105

<210> SEQ ID NO 22
<211> LENGTH: 110
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Thr Ser Tyr
            20                  25                  30

Glu Ile Ser Trp Val Arg Gln Ala Pro Gly Lys Gly Leu Glu Trp Val
        35                  40                  45

Gly Ser Ile Tyr Leu Trp Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Gly Gln Arg Tyr Ala Met Asp Val Trp Gly Gln
            100                 105                 110

```
<210> SEQ ID NO 23
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Ser Pro
            20                  25                  30

Tyr Ile Ser Trp Val Arg Gln Ala Pro Gly Lys Gly Leu Glu Trp Val
        35                  40                  45

Ala Ser Ile Phe Tyr Tyr Ser Gly Ala Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Gly Tyr Gly Tyr Asn Gln Trp Phe Tyr Ser Ile Tyr Gln
            100                 105                 110

Ser Tyr Phe Asp Tyr Trp Gly Gln
            115                 120

```
<210> SEQ ID NO 24
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24
```

Asp Val Ser Thr Ala Val Ala

<210> SEQ ID NO 25
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Ser Ile Ser Ser Tyr Leu Ala
1               5

<210> SEQ ID NO 26
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Ser Ala Ser Phe Leu Tyr Ser
1               5

<210> SEQ ID NO 27
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Gly Ala Ser Ser Arg Ala Ser
1               5

<210> SEQ ID NO 28
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Ser Tyr Thr Thr Pro Pro Thr
1               5

<210> SEQ ID NO 29
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Arg Tyr Ser Gln Pro Ile Thr
1               5

<210> SEQ ID NO 30

```
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Ser Tyr Thr Ala Lys Leu Thr
1               5

<210> SEQ ID NO 31
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Tyr Tyr Ile Tyr Pro Ala Thr
1               5

<210> SEQ ID NO 32
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

His Asn Asp Leu Pro Leu Thr
1               5

<210> SEQ ID NO 33
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Val Ile Ser Ser Ser Leu Ala
1               5

<210> SEQ ID NO 34
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Gly Ala Ser Phe Leu Tyr Ser
1               5

<210> SEQ ID NO 35
<211> LENGTH: 10
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 35

Gly Phe Thr Phe Thr Asp Tyr Asp Ile Ser
1               5                   10

<210> SEQ ID NO 36
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Gly Phe Ser Phe Ile Asp Tyr Asp Ile Ser
1               5                   10

<210> SEQ ID NO 37
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Ser Asp Gly Tyr Thr Tyr Tyr Ala Asp Ser Val Lys Gly
1               5                   10

<210> SEQ ID NO 38
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Pro Asp Cys Tyr Thr Tyr Tyr Ala Asp Ser Val Lys Gly
1               5                   10

<210> SEQ ID NO 39
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Pro Asp Ala Tyr Thr Tyr Pro Asp Cys Tyr Thr Tyr Tyr Ala Asp Ser
1               5                   10                  15

Val Lys Gly

<210> SEQ ID NO 40
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 40

Tyr Leu Tyr Trp Ser Tyr Val
1               5

<210> SEQ ID NO 41
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Tyr Asp Gly Tyr Thr Tyr Tyr Ala Asp Ser Val Lys Gly
1               5                   10

<210> SEQ ID NO 42
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Pro Asp Ala Tyr Thr Tyr Tyr Ala Asp Ser Val Lys Gly
1               5                   10

<210> SEQ ID NO 43
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Pro Asp Ser Tyr Thr Tyr Tyr Ala Asp Ser Val Lys Gly
1               5                   10

<210> SEQ ID NO 44
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Tyr Glu Gly Tyr Thr Tyr Tyr Ala Asp Ser Val Lys Gly
1               5                   10

<210> SEQ ID NO 45
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

```
Thr Ser Tyr Glu Ile Ser
1               5

<210> SEQ ID NO 46
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Trp Val Gly Ser Ile Tyr Leu Trp Gly Gly
1               5                   10

<210> SEQ ID NO 47
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Ala Arg Phe Gly Gln Arg Tyr Ala
1               5

<210> SEQ ID NO 48
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Thr Ser Pro Tyr Ile Ser
1               5

<210> SEQ ID NO 49
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Trp Val Ala Ser Ile Phe Tyr Tyr Ser Gly
1               5                   10

<210> SEQ ID NO 50
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Ala Arg Gly Gly Tyr Gly Tyr Asn Gln Trp Phe Tyr Ser Ile Tyr Gln
1               5                   10                  15

Ser Tyr
```

<210> SEQ ID NO 51
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 51

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser His Tyr
            20                  25                  30

Ala Ile Ser Trp Val Arg Gln Ala Pro Gly Lys Gly Leu Glu Trp Val
        35                  40                  45

Ser Val Ile Ser Pro Glu Asp Gly Ser Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Asp Tyr Val Thr Ser Phe Met Arg Trp Tyr Phe Tyr Gly
            100                 105                 110

Ser Gly Met Asp Val Trp Gly Gln
        115                 120

<210> SEQ ID NO 52
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 52

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Thr
            20                  25                  30

Ala Ile His Trp Val Arg Gln Ala Pro Gly Lys Gly Leu Glu Trp Val
        35                  40                  45

Gly Trp Ile Tyr Pro Tyr Ser Gly Asn Thr Asn Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gln Val Pro Asp Met Trp Ala Met Asp Tyr Trp Gly Gln
            100                 105                 110

<210> SEQ ID NO 53
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 53

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Asp Ile His Trp Val Arg Gln Ala Ser Ala Asp Thr Ser Lys Asn Thr
        35                  40                  45

Ala Pro Gly Lys Gly Leu Glu Trp Val Ala Gly Ile Ser Pro Asn Asp
    50                  55                  60

Gly Tyr Thr Asp Tyr Ala Asp Ser Val Lys Gly Arg Phe Thr Ile Tyr
65                  70                  75                  80

Leu Gln Met Asn Ser Leu Arg Ala Glu Asp Thr Ala Val Tyr Tyr Cys
                85                  90                  95

Ala Arg Ser Leu Pro Trp Thr Leu Gly Val Met Asp Tyr Trp Gly Gln
            100                 105                 110
```

<210> SEQ ID NO 54
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 54

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Arg Ile Thr Pro Gly Asp Gly Asp Thr Asn Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Trp Tyr Gly Asp Tyr Gly Val Trp Pro Ala His Ile Asp
            100                 105                 110

Val Met Asp Tyr Trp Gly Gln
        115
```

<210> SEQ ID NO 55
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 55

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Asp Ile Ser Trp Val Arg Gln Ala Pro Gly Lys Gly Leu Glu Trp Val
```

```
              35                  40                  45
Ala Ser Ile Ser Pro Ser Asp Gly Tyr Thr Tyr Tyr Ala Asp Ser Val
 50                  55                  60
Lys Gly Arg Phe Thr Ile Ser Ala Asp Thr Ser Lys Asn Thr Ala Tyr
 65                  70                  75                  80
Leu Gln Met Asn Ser Leu Arg Ala Glu Asp Thr Ala Val Tyr Tyr Cys
                 85                  90                  95
Ala Arg Tyr Leu Tyr Trp Ser Tyr Val Met Asp Tyr Trp Gly Gln
            100                 105                 110

<210> SEQ ID NO 56
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 56

Glu Val Gln Leu Val Glu Ser Gly Gly Gly Leu Val Gln Pro Gly Gly
  1               5                  10                  15
Ser Leu Arg Leu Ser Cys Ala Ala Ser Gly Phe Thr Phe Ser Ser Tyr
                 20                  25                  30
Ala Ile Ser Trp Val Arg Gln Ala Pro Gly Lys Gly Leu Glu Trp Val
             35                  40                  45
Ala Ser Ile Ser Pro Tyr Gly Gly Tyr Thr Tyr Tyr Ala Asp Ser Val
 50                  55                  60
Lys Gly Arg Phe Thr Ile Ser Ala Asp Thr Ser Lys Asn Thr Ala Tyr
 65                  70                  75                  80
Leu Gln Met Asn Ser Leu Arg Ala Glu Asp Thr Ala Val Tyr Tyr Cys
                 85                  90                  95
Ala Arg Gly Ser Leu Ile Phe Asp Tyr Trp Gly Gln
            100                 105

<210> SEQ ID NO 57
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 57

Glu Val Gln Leu Val Glu Ser Gly Gly Gly Leu Val Gln Pro Gly Gly
  1               5                  10                  15
Ser Leu Arg Leu Ser Cys Ala Ala Ser Gly Phe Thr Phe Thr Asn Thr
                 20                  25                  30
Gly Ile His Trp Val Arg Gln Ala Pro Gly Lys Gly Leu Glu Trp Val
             35                  40                  45
Gly Ser Ile Asn Pro Asp Gly Gly Ala Thr Asp Tyr Ala Asp Ser Val
 50                  55                  60
Lys Gly Arg Phe Thr Ile Ser Ala Asp Thr Ser Lys Asn Thr Ala Tyr
 65                  70                  75                  80
Leu Gln Met Asn Ser Leu Arg Ala Glu Asp Thr Ala Val Tyr Tyr Cys
                 85                  90                  95
Ala Arg Val Val Leu Phe Trp Ala Ala Gly Val Met Asp Tyr Trp Gly
            100                 105                 110
```

Gln

<210> SEQ ID NO 58
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 58

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Val Tyr
            20                  25                  30

Gly Ile His Trp Val Arg Gln Ala Pro Gly Lys Gly Leu Glu Trp Val
        35                  40                  45

Ala Gly Ile Asn Pro Ser Gly Asn Thr Asn Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg Ala Ala Val Thr Phe Ser Asp Trp Val Tyr Arg Arg Tyr
            100                 105                 110

Tyr Ala Met Asp Tyr Trp Gly Gln
        115                 120

<210> SEQ ID NO 59
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 59

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Thr Ser Tyr
            20                  25                  30

Met Met Ser Trp Val Arg Gln Ala Pro Gly Lys Gly Leu Glu Trp Val
        35                  40                  45

Ser Thr Ile Tyr Pro Glu Ser Gly Ala Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Gly Tyr Tyr Tyr Ser Thr Ser Ile Lys Tyr Tyr Pro Trp
            100                 105                 110

Phe Asp Tyr Trp Gly Gln
        115

<210> SEQ ID NO 60
<211> LENGTH: 116
<212> TYPE: PRT

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 60

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Arg Ile Ser Pro Ser Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Ser His Lys Tyr Tyr Ser Leu Phe Pro Ala Trp Met Asp
            100                 105                 110

Val Trp Gly Gln
        115

<210> SEQ ID NO 61
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 61

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Gly Ala Ser Ser Arg Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ser Pro Leu
                85                  90                  95

Thr Phe Gly Gln Gly Thr Lys Val Glu Ile Lys Arg
            100                 105

<210> SEQ ID NO 62
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 62

Glu Val Gln Leu Val Glu Ser Gly Gly Gly Leu Val Gln Pro Gly Gly
1               5                   10                  15

```
Ser Leu Arg Leu Ser Cys Ala Ala Ser Gly Phe Ser Phe Ser Ser Tyr
         20                  25                  30

Glu Ile Ser Trp Val Arg Gln Ala Pro Gly Lys Gly Leu Glu Trp Val
         35                  40                  45

Ser Ser Ile Tyr Ala Tyr Gly Gly Ser Thr Tyr Tyr Ala Asp Ser Val
 50                  55                  60

Lys Gly Arg Phe Thr Ile Ser Ala Asp Thr Ser Lys Asn Thr Ala Leu
 65                  70                  75                  80

Gln Met Asn Ser Leu Arg Ala Glu Asp Thr Ala Val Tyr Tyr Cys Ala
             85                  90                  95

Arg Phe Gly Met Tyr Ser Arg Trp Lys Thr Gln Pro Ala Met Asp Val
            100                 105                 110

Trp Gly Gln
        115
```

```
<210> SEQ ID NO 63
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 63

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Ser Thr Ala
             20                  25                  30

Val Ala Trp Tyr Gln Gln Lys Pro Gly Lys Ala Pro Lys Leu Leu Ile
         35                  40                  45

Tyr Ser Ala Ser Phe Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Thr Pro Arg Ser
             85                  90                  95

Thr Phe Gly Gln Gly Thr Lys Val Glu Ile Lys Arg
            100                 105
```

```
<210> SEQ ID NO 64
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 64

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Ser Thr Ala
             20                  25                  30

Val Ala Trp Tyr Gln Gln Lys Pro Gly Lys Ala Pro Lys Leu Leu Ile
         35                  40                  45

Tyr Ser Ala Ser Phe Leu Tyr Ser Gly Val Pro Ser Arg Phe Ser Gly
 50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Ser Thr Thr Thr
                 85                  90                  95

Thr Phe Gly Gln Gly Thr Lys Val Glu Ile Lys Arg
                100                 105
```

<210> SEQ ID NO 65
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 65

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Val Ser Thr Ala
                 20                  25                  30

Val Ala Trp Tyr Gln Gln Lys Pro Gly Lys Ala Pro Lys Leu Leu Ile
             35                  40                  45

Tyr Ser Ala Ser Phe Leu Tyr Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Gln Asn Pro Gln Thr
                 85                  90                  95

Thr Phe Gly Gln Gly Thr Lys Val Glu Ile Lys Arg
                100                 105
```

<210> SEQ ID NO 66
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 66

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Arg Ile Lys Arg Tyr
                 20                  25                  30

Leu Ala Trp Tyr Gln Gln Lys Pro Gly Lys Ala Pro Lys Leu Leu Ile
             35                  40                  45

Tyr Gly Ala Ser Ser Arg Ala Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Arg Phe Ser Gln His Ile
                 85                  90                  95

Thr Phe Gly Gln Gly Thr Lys Val Glu Ile Lys Arg
                100                 105
```

<210> SEQ ID NO 67
<211> LENGTH: 108
<212> TYPE: PRT

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 67

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Gly Ala Ser Ser Arg Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Tyr Ser Trp His Thr
                85                  90                  95

Thr Phe Gly Gln Gly Thr Lys Val Glu Ile Lys Arg
            100                 105

<210> SEQ ID NO 68
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 68

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Gly Ala Ser Ser Arg Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Tyr Ser Leu Pro Ile
                85                  90                  95

Thr Phe Gly Gln Gly Thr Lys Val Glu Ile Lys Arg
            100                 105

<210> SEQ ID NO 69
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 69

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

```
Asp Ile Ser Trp Val Arg Gln Ala Pro Gly Lys Gly Leu Glu Trp Val
            35                  40                  45

Ala Ser Ile Ser Pro Tyr Asp Gly Tyr Ala Tyr Tyr Ala Asp Ser Val
        50                  55                  60

Lys Gly Arg Phe Thr Ile Ser Asp Thr Ser Lys Asn Thr Ala Tyr
 65                  70                  75                  80

Leu Gln Met Asn Ser Leu Arg Ala Glu Asp Thr Ala Val Tyr Tyr Cys
                85                  90                  95

Ala Arg Tyr Leu Tyr Trp Ser Tyr Val Met Asp Tyr Trp Gly Gln Gly
            100                 105                 110

Thr Leu Val Thr Val Ser Ser
        115
```

<210> SEQ ID NO 70
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 70

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Tyr Asp Tyr
            20                  25                  30

Asp Ile Ser Trp Val Arg Gln Ala Pro Gly Lys Gly Leu Glu Trp Val
            35                  40                  45

Ala Ser Ile Ser Pro Leu Asp Gly Tyr Ser Tyr Tyr Ala Asp Ser Val
        50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                85                  90                  95

Ala Arg Tyr Leu Tyr Trp Ser Tyr Val Met Asp Tyr Trp Gly Gln Gly
            100                 105                 110

Thr Leu Val Thr Val Ser Ser
        115
```

<210> SEQ ID NO 71
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 71

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Asp Tyr
            20                  25                  30

Asp Ile Ser Trp Val Arg Gln Ala Pro Gly Lys Gly Leu Glu Trp Val
            35                  40                  45

Ala Ser Ile Asp Pro Tyr Glu Gly Tyr Thr Tyr Tyr Ala Asp Ser Val
        50                  55                  60
```

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Leu Tyr Trp Ser Tyr Val Met Asp Tyr Trp Gly Gln Gly
            100                 105                 110

Thr Leu Val Thr Val Ser Ser
        115

<210> SEQ ID NO 72
<211> LENGTH: 126
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 72

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Thr Ser Tyr
            20                  25                  30

Met Met Ser Trp Val Arg Gln Ala Pro Gly Lys Gly Leu Glu Trp Val
        35                  40                  45

Ser Thr Ile Tyr Pro Glu Ser Gly Ala Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Gly Tyr Tyr Tyr Ser Thr Ser Ile Lys Tyr Tyr Pro Trp
            100                 105                 110

Phe Asp Tyr Trp Gly Gln Gly Thr Leu Val Thr Val Ser Ser
        115                 120                 125

<210> SEQ ID NO 73
<211> LENGTH: 126
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 73

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Thr Ser Tyr
            20                  25                  30

Met Met Ser Trp Val Arg Gln Ala Pro Gly Lys Gly Leu Glu Trp Val
        35                  40                  45

Ser Thr Ile Tyr Pro Glu Ser Gly Ala Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Gly Tyr Tyr Tyr Ser Thr Ser Ile Lys Tyr Tyr Pro Trp

```
                  100                 105                 110
Phe Asp Tyr Trp Gly Gln Gly Thr Leu Val Thr Val Ser Ser
            115                 120                 125

<210> SEQ ID NO 74
<211> LENGTH: 126
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 74

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Pro Ser Tyr
            20                  25                  30

Phe Ile Ser Trp Val Arg Gln Ala Pro Gly Lys Gly Leu Glu Trp Val
        35                  40                  45

Ser Met Ile Tyr Pro Val Ser Gly Ala Thr Val Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Gly Tyr Tyr Tyr Ser Thr Ser Ile Lys Tyr Tyr Pro Trp
            100                 105                 110

Phe Asp Tyr Trp Gly Gln Gly Thr Leu Val Thr Val Ser Ser
        115                 120                 125

<210> SEQ ID NO 75
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 75

Ser Tyr Thr Pro Arg Ser Thr
1               5

<210> SEQ ID NO 76
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 76

Gln Tyr Tyr Ser Thr Thr Thr Thr
1               5

<210> SEQ ID NO 77
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 77

Gln Gln Ser Gln Asn Pro Gln Thr Thr
1               5

<210> SEQ ID NO 78
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 78

Arg Phe Ser Gln His Ile Thr
1               5

<210> SEQ ID NO 79
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 79

Arg Tyr Ser Trp His Thr Thr
1               5

<210> SEQ ID NO 80
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 80

Arg Tyr Ser Leu Pro Ile Thr
1               5

<210> SEQ ID NO 81
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 81

Gly Phe Ser Phe Thr Ser Tyr Met Met Ser
1               5                   10

<210> SEQ ID NO 82
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 82

```
Gly Phe Ser Phe Pro Ser Tyr Phe Ile Ser
1               5                   10
```

<210> SEQ ID NO 83
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 83

```
Glu Ser Gly Ala Thr Asp Tyr Ala Asp Ser Val Lys Gly
1               5                   10
```

<210> SEQ ID NO 84
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 84

```
Val Ser Gly Ala Thr Val Tyr Ala Asp Ser Val Lys Gly
1               5                   10
```

<210> SEQ ID NO 85
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 85

```
Tyr Asp Gly Tyr Ala Tyr Tyr Ala Asp Ser Val Lys Gly
1               5                   10
```

<210> SEQ ID NO 86
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 86

```
Leu Asp Gly Tyr Ser Tyr Tyr Ala Asp Ser Val Lys Gly
1               5                   10
```

<210> SEQ ID NO 87
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 87

```
Glu Gly Tyr Tyr Tyr Ser Thr Ser Ile Lys Tyr Tyr Pro Trp
1               5                   10
```

```
<210> SEQ ID NO 88
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 88

Gly Phe Thr Phe Tyr Asp Tyr Asp Ile Ser
1               5                   10

<210> SEQ ID NO 89
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 89

Arg Ile Lys Arg Tyr Leu Ala
1               5

<210> SEQ ID NO 90
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 90

Pro Asp Ser Tyr Thr Thr Tyr Tyr Ala Asp Ser Val Lys Gly
1               5                   10

<210> SEQ ID NO 91
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 91

Ser Phe Ser Gly Ile Asp Tyr Asp Ile Ser
1               5                   10

<210> SEQ ID NO 92
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 92

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Asp Ile Ser Trp Val Arg Gln Ala Pro Gly Lys Gly Leu Glu Trp Val
        35                  40                  45
```

```
Ala Ser Ile Ser Pro Ser Asp Gly Tyr Thr Tyr Tyr Ala Asp Ser Val
            50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Tyr Leu Tyr Trp Ser Tyr Val Met Asp Tyr Trp Gly Gln Gly
                100                 105                 110

Thr Leu Val Thr Val Ser Ser
            115

<210> SEQ ID NO 93
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 93

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Asp Tyr
                 20                  25                  30

Asp Ile Ser Trp Val Arg Gln Ala Pro Gly Lys Gly Leu Glu Trp Val
             35                  40                  45

Ala Ser Ile Ser Pro Pro Asp Cys Tyr Thr Tyr Tyr Ala Asp Ser Val
            50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Tyr Leu Tyr Trp Ser Tyr Val Met Asp Tyr Trp Gly Gln Gly
                100                 105                 110

Thr Leu Val Thr Val Ser Ser
            115

<210> SEQ ID NO 94
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 94

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Ser Phe Ile Asp Tyr
                 20                  25                  30

Asp Ile Ser Trp Val Arg Gln Ala Pro Gly Lys Gly Leu Glu Trp Val
             35                  40                  45

Ala Ser Ile Ser Pro Tyr Asp Gly Tyr Thr Tyr Tyr Ala Asp Ser Val
            50                  55                  60

Lys Gly Arg Phe Thr Ile Ser Ala Asp Thr Ser Lys Asn Thr Ala Tyr
 65                  70                  75                  80
```

```
Leu Gln Met Asn Ser Leu Arg Ala Glu Asp Thr Ala Val Tyr Tyr Cys
                85                  90                  95

Ala Arg Tyr Leu Tyr Trp Ser Tyr Val Met Asp Tyr Trp Gly Gln Gly
            100                 105                 110

Thr Leu Val Thr Val Ser Ser
        115

<210> SEQ ID NO 95
<211> LENGTH: 119
<212> TYPE: PRT
<213> ORGANISM: Artificial <Sequence
<220> FEATURE:
<221> NAME/KEY: source
<223> OTHER INFORMATION: /note="Description of Artificial Sequence:
      Synthetic polypeptide"

<400> SEQUENCE: 95

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ile Asp Tyr
            20                  25                  30

Asp Ile Ser Trp Val Arg Gln Ala Pro Gly Lys Gly Leu Glu Trp Val
        35                  40                  45

Ala Ser Ile Ser Pro Tyr Glu Gly Tyr Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Tyr Leu Tyr Trp Ser Tyr Val Met Asp Tyr Trp Gly Gln Gly
            100                 105                 110

Thr Leu Val Thr Val Ser Ser
        115

<210> SEQ ID NO 96
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 96

Gly Ala Ser Phe Phe Tyr Ser
1               5
```